(12) United States Patent
Liu et al.

(10) Patent No.: US 9,828,373 B2
(45) Date of Patent: Nov. 28, 2017

(54) 2-AMINO-PYRIDO[2,3-D]PYRIMIDIN-7(8H)-ONE DERIVATIVES AS CDK INHIBITORS AND USES THEREOF

(71) Applicant: SUNSHINE LAKE PHARMA CO., LTD., Dongguan, Guangdong (CN)

(72) Inventors: Bing Liu, Dongguan (CN); Yingjun Zhang, Dongguan (CN); Linlin Nie, Dongguan (CN); Shun Bai, Dongguan (CN); Mingyu Guan, Dongguan (CN); Xuke Li, Dongguan (CN); Changchung Cheng, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/318,366

(22) PCT Filed: Jul. 23, 2015

(86) PCT No.: PCT/CN2015/084984
§ 371 (c)(1),
(2) Date: Dec. 13, 2016

(87) PCT Pub. No.: WO2016/015598
PCT Pub. Date: Feb. 4, 2016

(65) Prior Publication Data
US 2017/0121323 A1    May 4, 2017

(30) Foreign Application Priority Data
Jul. 26, 2014   (CN) .......................... 2014 1 0361634
Feb. 12, 2015   (CN) .......................... 2015 1 0076030

(51) Int. Cl.
| C07D 471/04 | (2006.01) |
| C07D 519/00 | (2006.01) |
| A61K 31/5377 | (2006.01) |
| A61K 31/5383 | (2006.01) |
| A61K 31/519 | (2006.01) |
| A61K 45/06 | (2006.01) |

(52) U.S. Cl.
CPC .......... *C07D 471/04* (2013.01); *A61K 31/519* (2013.01); *A61K 31/5377* (2013.01); *A61K 31/5383* (2013.01); *A61K 45/06* (2013.01); *C07D 519/00* (2013.01)

(58) Field of Classification Search
CPC .......................... C07D 519/00; C07D 471/04
See application file for complete search history.

(56) References Cited

U.S. PATENT DOCUMENTS

| 5,620,981 A | 4/1997 | Blankley et al. |
| 6,420,384 B2 | 7/2002 | Weigele et al. |
| 6,498,163 B1 | 12/2002 | Boschelli et al. |
| 6,506,749 B2 | 1/2003 | Chen et al. |
| 6,534,535 B1 | 3/2003 | Zhu et al. |
| 6,683,183 B2 | 1/2004 | Kramer et al. |
| 6,696,566 B2 | 2/2004 | Chen et al. |
| 6,777,413 B2 | 8/2004 | Zhu et al. |
| 6,936,612 B2 | 8/2005 | Barvian et al. |
| 7,022,711 B2 | 4/2006 | Hamby et al. |
| 7,022,849 B2 | 4/2006 | Pitts et al. |
| 7,196,090 B2 | 3/2007 | Connolly et al. |
| 7,449,582 B2 | 11/2008 | Ding et al. |
| 7,645,764 B2 | 1/2010 | Gabriel et al. |
| 7,696,213 B2 | 4/2010 | Cheng et al. |
| 7,842,806 B2 | 11/2010 | Perreaut et al. |
| 7,998,978 B2 | 8/2011 | Huang et al. |
| 8,247,408 B2 | 8/2012 | Baik et al. |
| 8,268,840 B2 | 9/2012 | Brookfield et al. |
| 8,372,970 B2 | 2/2013 | Vollrath et al. |
| 8,518,958 B2 | 8/2013 | Murthi et al. |
| 8,680,099 B2 | 3/2014 | Campbell et al. |
| 8,889,696 B2 | 11/2014 | Reddy et al. |
| 8,912,203 B2 | 12/2014 | Campbell et al. |
| 8,987,267 B2 | 3/2015 | Reddy et al. |
| 9,321,786 B2 | 4/2016 | D'Agostino et al. |
| 9,434,700 B2 | 9/2016 | Bifulco, Jr. et al. |
| 2004/0236084 A1 | 11/2004 | Biwersi et al. |
| 2005/0009849 A1 | 1/2005 | Veach et al. |
| 2005/0182078 A1 | 8/2005 | Barvian et al. |
| 2006/0047118 A1 | 3/2006 | Stadtmueller et al. |
| 2006/0142312 A1 | 6/2006 | Flamme et al. |

(Continued)

FOREIGN PATENT DOCUMENTS

| CN | 101747306 | 6/2010 |
| CN | 104418860 | 3/2015 |

(Continued)

OTHER PUBLICATIONS

Reddy, M. V. Ramana al., Discovery of 8-Cyclopentyl-2-[4-(4-methyl-piperazin-1-yl)-phenylamino]-7-oxo-7,8-dihydro-pyrido[2,3-d]pyrimidine-6-carbonitrile as a Potent Inhibitor of Cyclin-Dependent Kinase 4 (CDK4) and AMPK-Related Kinase 5 (ARK5), Journal of Medicinal Chemistry, 2014, 57(3), 578-599.

Baughn, Linda B. al., A Novel Orally Active Small Molecule Potently Induces G1 Arrest in Primary Myeloma Cells and Prevents Tumor Growth by Specific Inhibition of Cyclin-Dependent Kinase 4/6, Cancer Research, 2006, 66(15), 7661-7667.

Lu, Heshu al., Toward Understanding the Structural Basis of Cyclin-Dependent Kinase 6 Specific Inhibition, Journal of Medicinal Chemistry, 2006, 49(13), 3826-3831.

N Bathini, Yadagiri al., 2-Aminoquinazoline inhibitors of cyclin-dependent kinases, Bioorganic & Medicinal Chemistry Letters, 2005, 15(17), 3881-3885.

(Continued)

*Primary Examiner* — Bruck Kifle
(74) *Attorney, Agent, or Firm* — Kam W. Law; Squire Patton Boggs (US) LLP

(57) ABSTRACT

The invention provides compounds as CDK small-molecule inhibitors and uses thereof, the compounds can be used for treating inflammation and cell proliferation diseases. The novel compound of the invention is a powerful cyclin-dependent kinase 4 (CDK 4) or cyclin-dependent kinase-6 (CDK 6) inhibitor.

15 Claims, No Drawings

(56) References Cited

U.S. PATENT DOCUMENTS

| | | |
|---|---|---|
| 2008/0255162 A1 | 10/2008 | Bruendl et al. |
| 2009/0036472 A1 | 2/2009 | Palle et al. |
| 2009/0131430 A1 | 5/2009 | Palle et al. |
| 2009/0209536 A1 | 8/2009 | Gahman et al. |
| 2009/0312321 A1 | 12/2009 | Ren et al. |
| 2010/0150827 A1 | 6/2010 | Buhr et al. |
| 2013/0116263 A1 | 5/2013 | Campbell et al. |
| 2013/0231348 A1 | 9/2013 | Campbell et al. |
| 2013/0252967 A1 | 9/2013 | Campbell et al. |
| 2014/0163026 A1 | 6/2014 | Campbell et al. |
| 2014/0323477 A1 | 10/2014 | Crawford et al. |
| 2014/0323478 A1 | 10/2014 | Duron et al. |
| 2015/0126508 A1 | 5/2015 | Li et al. |
| 2015/0291531 A1 | 10/2015 | Lavoie et al. |
| 2016/0024084 A1 | 1/2016 | Morgan |
| 2016/0130268 A1 | 5/2016 | Brameld et al. |
| 2016/0176866 A1 | 6/2016 | Borrell Bilbao et al. |
| 2016/0229849 A1 | 8/2016 | Verner et al. |

FOREIGN PATENT DOCUMENTS

| | | |
|---|---|---|
| JP | 2001131152 | 5/2001 |
| WO | 2000018761 | 4/2000 |
| WO | 2001070741 | 9/2001 |
| WO | 2006071095 | 7/2006 |
| WO | 2012028756 | 3/2012 |
| WO | 2014079232 | 5/2014 |
| WO | 2014134308 | 9/2014 |
| WO | 2014174745 | 10/2014 |
| WO | 2014183520 | 11/2014 |
| WO | 2015011252 | 1/2015 |
| WO | 2015084936 | 6/2015 |
| WO | 2015086523 A | 6/2015 |

OTHER PUBLICATIONS

Toogood, Peter L. al., Discovery of a Potent and Selective Inhibitor of Cyclin-Dependent Kinase 4/6, Journal of Medicinal Chemistry, 2005, 48(7), 2388-2406.

VanderWel, Scott N. al., Pyrido[2,3-d]pyrimidin-7-ones as Specific Inhibitors of Cyclin-Dependent Kinase 4, Journal of Medicinal Chemistry, 2005, 48(7), 2371-2387.

Barvian, Mark al., Pyrido[2,3-d]pyrimidin-7-one Inhibitors of Cyclin-Dependent Kinases. [Erratum to document cited in CA134, Journal of Medicinal Chemistry, 2001, 44(6), 1016.

Barvian, Mark al., Pyrido[2,3-d]pyrimidin-7-one Inhibitors of Cyclin-Dependent Kinases, Journal of Medicinal Chemistry 2000, 43(24), 4606-4616.

International Search Report of PCT/CN2015/084984, (dated 2015).

Written Opinion of PCT/CN2015/084984, (dated 2015).

2-AMINO-PYRIDO[2,3-D]PYRIMIDIN-7(8H)-ONE DERIVATIVES AS CDK INHIBITORS AND USES THEREOF

CROSS-REFERENCE TO RELATED APPLICATIONS

This is a U.S. national stage application of the International Patent Application No. PCT/CN2015/084984, filed Jul. 23, 2015, which claims priorities to Chinese Patent Application No. 201410361634.X, filed Jul. 26, 2014 and No. 201510076030.5, filed Feb. 12, 2015, all of which are incorporated herein by reference in their entirety.

FIELD OF THE INVENTION

The present invention relates to novel compounds as CDK small-molecule inhibitors and pharmaceutical compositions thereof, and also to uses of the compounds and the pharmaceutical compositions in the treatment of exceedingly proliferative disorders.

BACKGROUND OF THE INVENTION

In recent years, cancer has surpassed cardiovascular diseases to become the world's leading death disease, antineoplastic research has an important academic and practical significance. The study found that almost all of the tumors are related to uncontrolled cell growth, blocked differentiation and apoptosis abnormalities caused by cell cycle control mechanisms disorder.

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as CDC2, and CDK2), cyclin B1-B3 (CDK1) and cyclin D1-D3 (CDK2, CDK4, CDK5, CDK6), cyclin E (CDK2). Each of these complexes is involved in a particular phase of the cell cycle. The activity of CDKs is regulated post-translationally, by transitory associations with other proteins, and by alterations of their intracellular localization. Tumor development is closely associated with genetic alteration and deregulation of CDKs and their regulators, suggesting that inhibitors of CDKs may be useful anti-cancer therapeutics.

CDKs, and their associated proteins, in co-ordinating and driving the cell cycle in proliferating cells play key roles in some biochemical pathways. Using therapeutics targeted generically at CDKs, or at specific CDKs can be for the treatment of proliferative disorders, such as cancers. CDK inhibitors could conceivably also be used to treat other conditions such as viral infections, autoimmune diseases and neuro-degenerative diseases, amongst others. CDK targeted therapeutics may also provide clinical benefits in the treatment of the previously described diseases when used in combination therapy with existing therapeutic agents. CDK targeted anticancer therapies could potentially have advantages over many current antitumour agents as they would not directly interact with DNA and should therefore reduce the risk of secondary tumour development.

Although a number of CDKs compounds have been disclosed in the art, in view of the number of pathological responses that are mediated by CDK, there remains a continuing need for drugs which can be used in the treatment of a variety of conditions mediated by CDK, especially CDK4/6.

SUMMARY OF THE INVENTION

There remain needs for a large number of new therapies and drugs used for treating disorders related to protein kinases, as well as compounds used for treating, preventing, or improving one or more of cancer, autoimmune diseases and infection diseases. The compounds provided herein can be used in regulating the activities of protein kinases such as CDKs, regulating or inhibiting the activities of CDK1, CDK2, CDK4, CDK6 or CDK9, especially regulating or inhibiting the activities of CDK4 or CDK6, which have good clinical prospects. The compounds provided herein have better characteristics of pharmacodynamics in vivo, pharmacokinetics and/or toxicology than the existing similar compound.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

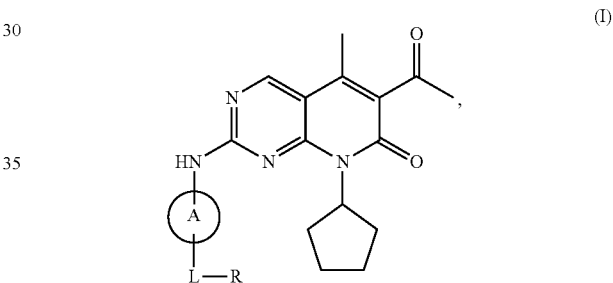

(I)

wherein L is a bond, $-(C(R^{3b})_2)_n-$, $-N(R^1)-(C(R^{3b})_2)_n-$, $-O-(C(R^{3b})_2)_n-$, $-S(=O)_m-$ or $-C(=O)-(C(R^{3b})_2)_n-$;

ring A is

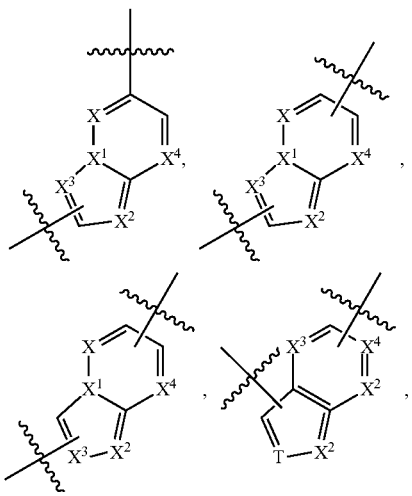

-continued

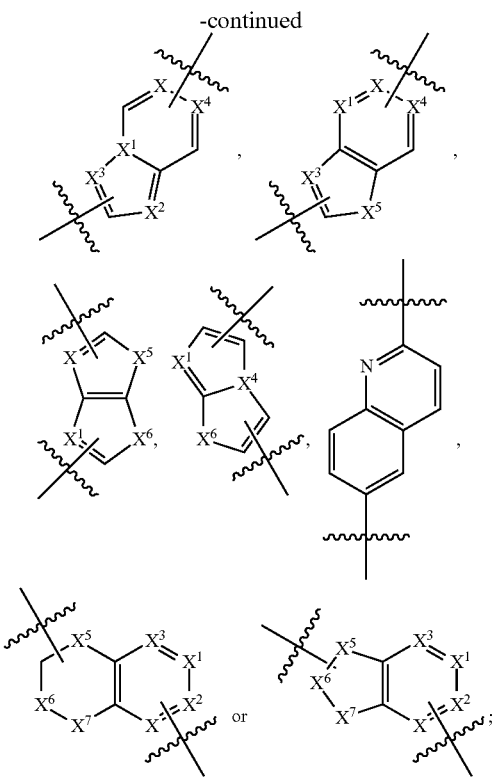

wherein when ═ is a double bond, T is X,

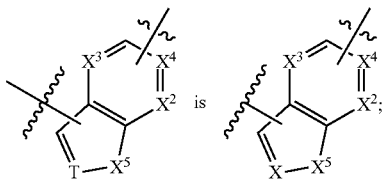

when ═ is a single bond, T is $X^6$,

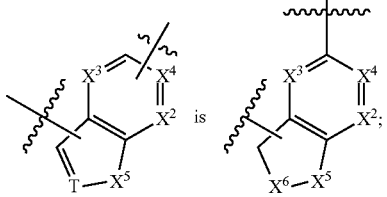

R is H, $R^{13}$, $-(C(R^{3b})_2)_n-N(R^{1a})-C(=O)-(C(R^{3b})_2)_n-R^{13}$ or $-(CH_2)_n-C(=O)-N(R^{1a})-(C(R^{3b})_2)_n-R^{13}$;

$R^{13}$ is H, $C_{3-9}$ cycloalkyl, $C_{1-9}$ heteroaryl, $C_{2-9}$ heterocyclyl, $C_{5-11}$ spiro heterobicyclyl, $C_{5-11}$ bridged heterobicyclyl or $C_{5-11}$ fused heterobicyclyl;

wherein each $X^5$, $X^6$ and $X^7$ is independently $-C(R^{3a})_2-$, $-N(R^2)-$, $-O-$, $-S(=O)_m-$ or $-C(=O)-$;

each X, $X^1$, $X^2$, $X^3$ and $X^4$ is independently $CR^{3a}$ or N;
each n is independently 0, 1, 2, 3, or 4;
each n1 is independently 1, 2, or 3;
each m is independently 0, 1, or 2;

each $R^{1a}$, $R^1$ and $R^2$ is independently H, $C_{1-4}$ haloalkyl, $H-(C(R^3)_2)_n-O-C(=O)-(C(R^3)_2)_n-$, $(R^4)_2N-(C(R^3)_2)_n-$, $HO-(C(R^3)_2)_n-C(=O)-$, $N(R^4)_2-C(=O)-$, $HO-(C(R^3)_2)_n-$, $H-(C(R^3)_2)_n-O-(C(R^3)_2)_n-$, $H-(C(R^3)_2)_n-SO_2-(C(R^3)_2)_n-$, $H-(C(R^3)_2)_n-C(=O)-(C(R^3)_2)_n-$, $CN-(C(R^3)_2)_n-C(=O)-$, $H-(C(R^3)_2)_n-O-C(=O)-C(=O)-(C(R^3)_2)_n-$, $C_{2-9}$ heterocyclyl, $C_{1-9}$ heteroaryl, $C_{3-9}$ cycloalkyl or $C_{1-4}$ alkyl;

each $R^{3a}$, $R^{3b}$ and $R^3$ is independently H, F, Cl, Br, $C_{1-4}$ alkyl, hydroxy, carboxy, amino, $C_{2-9}$ heterocyclyl, $C_{1-9}$ heteroaryl, $C_{3-9}$ cycloalkyl, $C_{1-4}$ haloalkyl, $H-(CH_2)_n-O-(CH_2)_n-$, $N(R^4)_2-C(=O)-$, $H-(CH_2)_n-SO_2-(CH_2)_n-$, $H-O-(CH_2)_n-C(=O)-(CH_2)_n-$, $H-(CH_2)_n-C(=O)-(CH_2)_n-$ or $N(R^4)_2-(CH_2)_n-$;

each $R^4$ is independently H, $C_{1-4}$ alkyl, hydroxy, carboxy, amino, $C_{1-4}$ alkoxy, amino-$C_{1-4}$-alkyl, $NH_2-C(=O)-$, $C_{2-9}$ heterocyclyl, $C_{1-9}$ heteroaryl, $C_{3-9}$ cycloalkyl, $C_{1-4}$ haloalkyl or $C_{1-4}$ alkylamino;

each moiety represented by A is independently and optionally substituted with one, two, three or four substituents independently selected from H, $C_{1-4}$ alkyl, F, Cl, Br, amino, hydroxy, carboxy, $C_{1-4}$ alkoxy, $C_{1-4}$ haloalkyl, $C_{1-4}$ alkylamino, amino-$C_{1-4}$-alkyl, $H-(C(R^3)_2)_n-O-C(=O)-(C(R^3)_2)_n-$, $(R^4)_2N-(C(R^3)_2)_n-$, $HO-(C(R^3)_2)_n-C(=O)-$, $N(R^4)_2-C(=O)-$, $HO-(C(R^3)_2)_n-$, $H-(C(R^3)_2)_n-O-(C(R^3)_2)_n-$, $H-(C(R^3)_2)_n-SO_2-(C(R^3)_2)_n-$, $H-(C(R^3)_2)_n-C(=O)-(C(R^3)_2)_n-$, $CN-(C(R^3)_2)_n-C(=O)-$, $H-(C(R^3)_2)_n-O-C(=O)-C(=O)-(C(R^3)_2)_n-$, cyano and nitro;

each alkyl, haloalkyl, $H-(C(R^3)_2)_n-O-C(=O)-(C(R^3)_2)_n-$, $N(R^4)_2-C(=O)-$, $H-(C(R^3)_2)_n-SO_2-(C(R^3)_2)_n-$, $-(C(R^3)_2)_n-N(R^4)_2$, $HO-(C(R^3)_2)_n-C(=O)-$, $HO-(C(R^3)_2)_n-$, $H-(C(R^3)_2)_n-O-(C(R^3)_2)_n-$, $H-(C(R^3)_2)_n-C(=O)-(C(R^3)_2)_n-$, $CN-(C(R^3)_2)_n-C(=O)-$, spiro heterobicyclyl, bridged heterobicyclyl, fused heterobicyclyl, heterocyclyl, cycloalkyl, heteroaryl and $H-(C(R^3)_2)_n-O-C(=O)-C(=O)-(C(R^3)_2)_n-$ described in R, $R^1$, $R^{1a}$, $R^2$ and/or $R^{13}$ is optionally and independently substituted with one, two, three or four independent $R^5$;

each $R^5$ is independently H, oxo(=O), $C_{1-6}$ alkyl, F, Cl, Br, amino, hydroxy, carboxy, $C_{1-4}$ alkoxy, $C_{1-4}$ alkylamino, amino-$C_{1-4}$-alkyl, $N(R^4)_2-C(=O)-$, $CN-(C(R^3)_2)_n-C(=O)-$, $C_{1-6}$ haloalkyl, $H-(C(R^3)_2)_n-O-C(=O)-(C(R^3)_2)_n-$, $H-(C(R^3)_2)_n-C(=O)-(C(R^3)_2)_n-$, $H-(C(R^3)_2)_n-SO_2-(C(R^3)_2)_n-$, $H-(C(R^3)_2)_n-O-(C(R^3)_2)_{n1}-C(=O)-(C(R^3)_2)_n-$, $H-(C(R^3)_2)_n-O-C(=O)-(C(R^3)_2)_n-$, $H-(C(R^3)_2)_n-O-(C(R^3)_2)_n-$, cyano, $C_{2-9}$ heterocyclyl, $C_{3-9}$ cycloalkyl, $C_{1-9}$ heteroaryl or nitro;

each alkyl, alkoxy, alkylamino, aminoalkyl, $N(R^4)_2-C(=O)-$, $CN-(C(R^3)_2)_n-C(=O)-$, haloalkyl, $H-(C(R^3)_2)_n-O-C(=O)-(C(R^3)_2)_n-$, $H-(C(R^3)_2)_n-O-C(=O)-C(=O)-(C(R^3)_2)_n-$, $H-(C(R^3)_2)_n-C(=O)-(C(R^3)_2)_n-$, $H-(C(R^3)_2)_n-SO_2-(C(R^3)_2)_n-$, $H-(C(R^3)_2)_n-O-(C(R^3)_2)_{n1}-C(=O)-(C(=O)-(C(R^3)_2)_n-$, $H-(C(R^3)_2)_n-O-(C(R^3)_2)_n-$, heterocyclyl, cycloalkyl and heteroaryl described in $R^5$ is independently and optionally substituted with one, two, three or four independent $R^6$; and each $R^6$ is independently H, oxo(=O), $C_{1-4}$ alkyl, F, Cl, Br, amino, hydroxy, carboxy, $C_{1-4}$ alkoxy, $C_{1-4}$ alkylamino, amino-$C_{1-4}$-alkyl, $N(R^4)_2-C(=O)-$, $CN-(C(R^3)_2)_n-C(=O)-$, $C_{1-4}$ haloalkyl, $H-(C(R^3)_2)_n-O-C(=O)-(C(R^3)_2)_n-$, $H-(C(R^3)_2)_n-O-C(=O)-C(=O)-$ $(C(R^3)_2)_n$—, H—$(C(R^3)_2)_n$—C(=O)—$(C(R^3)_2)_{n1}$—, H—$(C(R^3)_2)_n$—SO$_2$—$(C(R^3)_2)_n$—, H—$(C(R^3)_2)_n$—O—$(C(R^3)_2)_{m1}$—C(=O)—$(C(R^3)_2)_n$—, H—$(C(R^3)_2)_n$—O—$(C(R^3)_2)_n$—, cyano, $C_{2-9}$ heterocyclyl, $C_{3-9}$ cycloalkyl, $C_{1-9}$ heteroaryl or nitro.

In some embodiments, provided herein is a compound having Formula (II) or Formula (III), or a stereoisomer, a geometric isomer, a tautomer, an N-oxide, a hydrate, a solvate, a metabolite, an ester, a pharmaceutically acceptable salt or a prodrug thereof,

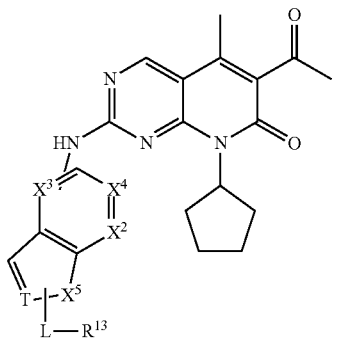

(II)

or

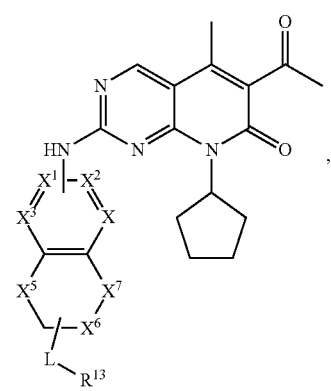

(III)

wherein L is a bond, —(CH$_2$)$_n$—, —N(R$^1$)—, —O—, —S— or —C(=O)—;

when ═ is a double bond, T is X;

when ═ is a single bond, T is X$^6$; and wherein n, R$^1$, X, X$^1$, X$^2$, X$^3$, X$^4$, X$^5$, X$^6$, X$^7$ and R$^{13}$ are as defined herein.

In some embodiments,

R$^{13}$ is H,

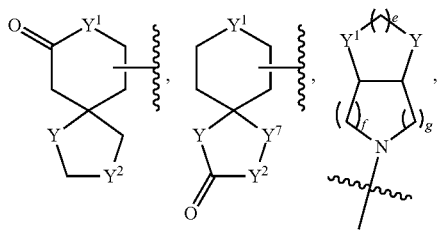

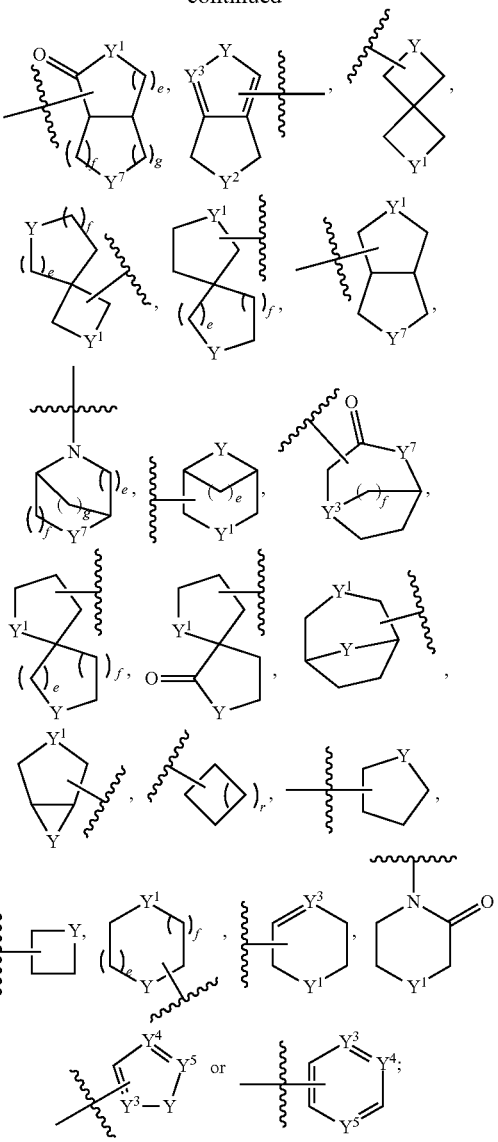

wherein each Y, Y$^1$, Y$^7$ and Y$^2$ is independently —C(R$^{3c}$)$_2$—, —N(R$^{2b}$)—, —O—, —S(=O)$_m$— or —C(=O)—;

each Y$^3$, Y$^4$ and Y$^5$ is independently CR$^{3c}$ or N;

each e, r, g and f is independently 0, 1, 2, or 3; and each R$^{2b}$ is independently H, C$_{1-4}$ haloalkyl, H—$(C(R^3)_2)_n$—O—C(=O)—$(C(R^3)_2)_n$—, $(R^4)_2$N—$(C(R^3)_2)_n$—, HO—$(C(R^3)_2)_n$—C(=O)—, N(R$^4$)$_2$—C(=O)—, HO—$(C(R^3)_2)_n$—, H—$(C(R^3)_2)_n$—O—$(C(R^3)_2)_n$—, H—$(C(R^3)_2)_n$—SO$_2$—$(C(R^3)_2)_n$—, H—$(C(R^3)_2)_n$—C(=O)—$(C(R^3)_2)_n$—, CN—$(C(R^3)_2)_n$—C(=O)—, H—$(C(R^3)_2)_n$—O—C(=O)—C(=O)—$(C(R^3)_2)_n$— or C$_{1-4}$ alkyl;

each R$^{3c}$ is independently H, F, Cl, Br, C$_{1-4}$ alkyl, hydroxy, carboxy, amino, C$_{1-4}$ haloalkyl, H—(CH$_2$)$_n$—O—(CH$_2$)$_n$—, N(R$^4$)$_2$—C(=O)—, H—(CH$_2$)$_n$—SO$_2$—(CH$_2$)$_n$—, H—O—(CH$_2$)$_n$—C(=O)—(CH$_2$)$_n$—, H—(CH$_2$)$_n$—C(=O)—(CH$_2$)$_n$— or N(R$^4$)$_2$—(CH$_2$)$_n$—;

wherein R$^3$, n, R$^4$ and m are as defined herein.

In some embodiments,

R$^{13}$ is cyclopropyl, cyclohexyl, cyclopentyl, cyclobutyl, H,

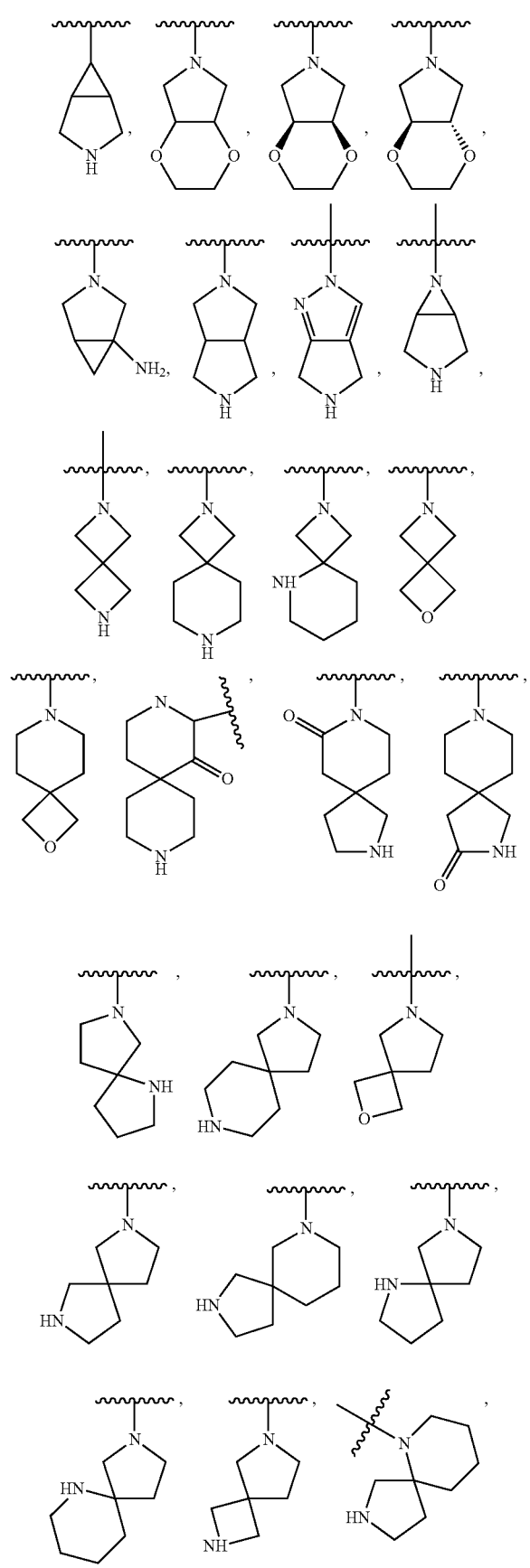
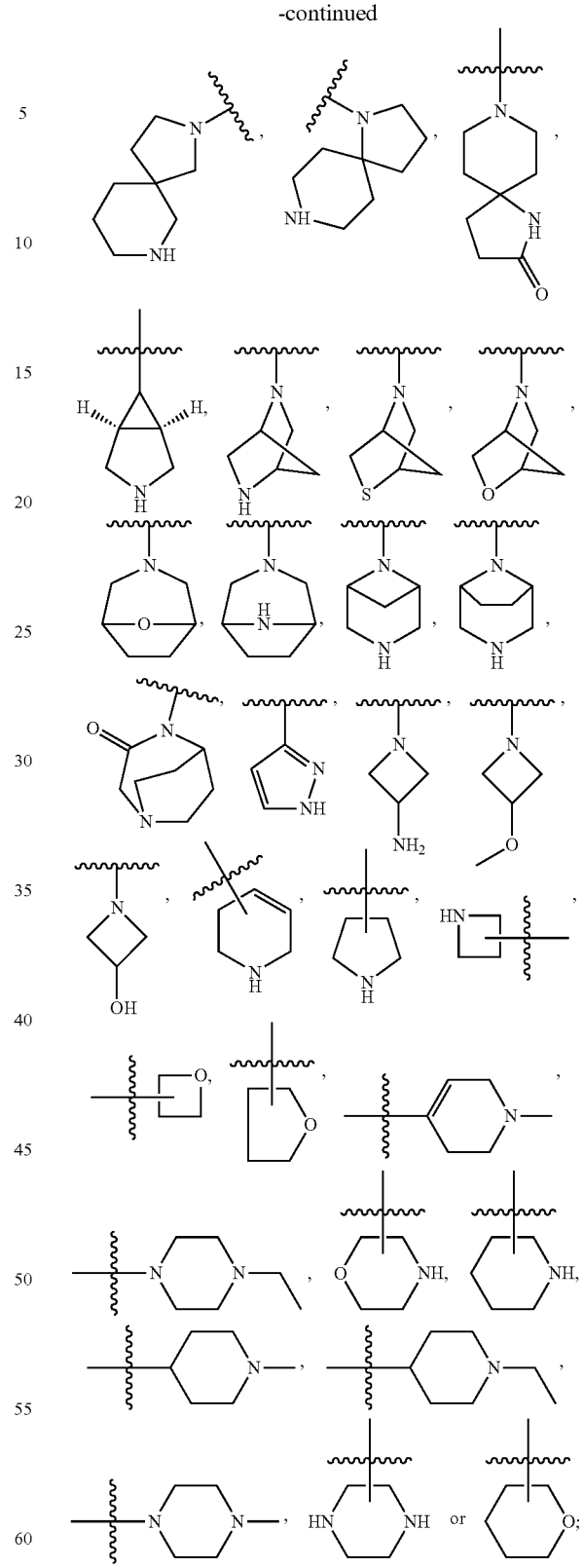
each moiety represented by $R^{13}$ is independently and optionally substituted with one, two, three or four independent $R^5$; and
wherein $R^5$ is as defined herein.

In some embodiments, ring A is
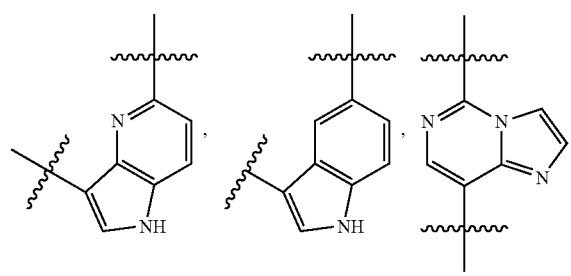
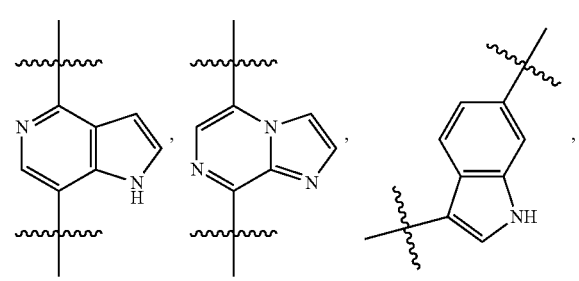
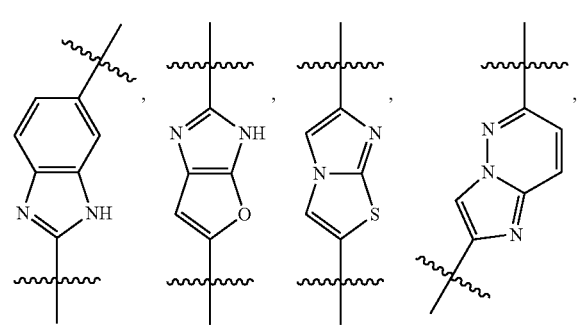
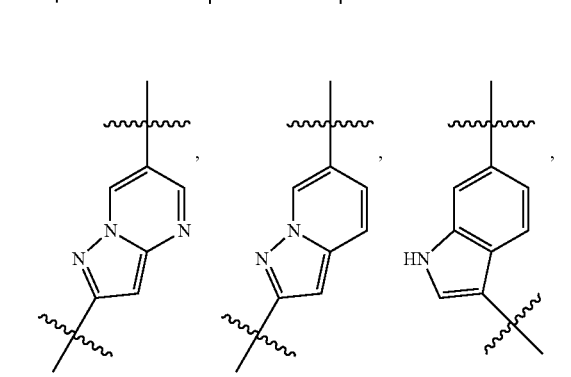
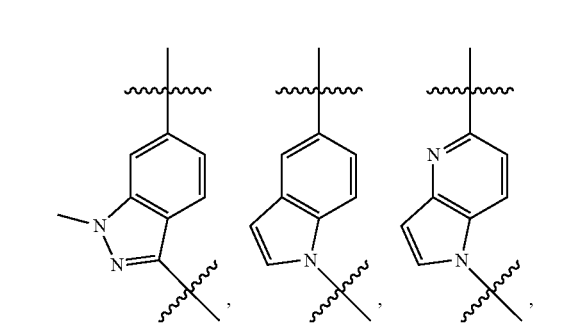
-continued
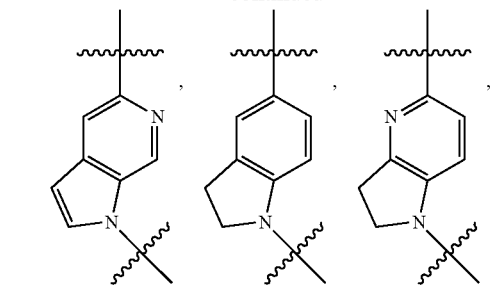
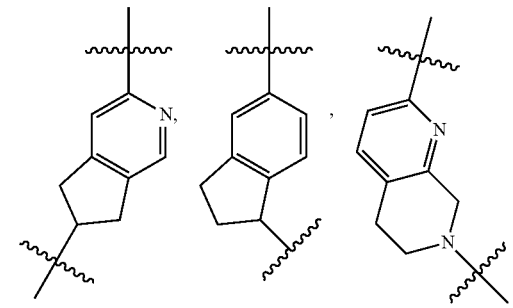
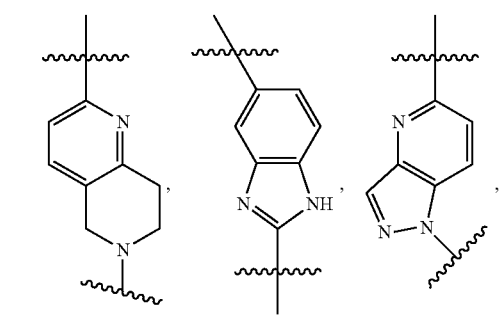
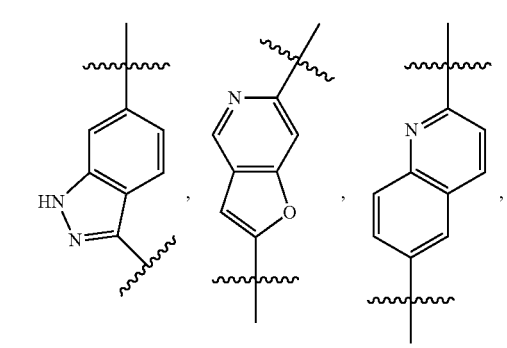
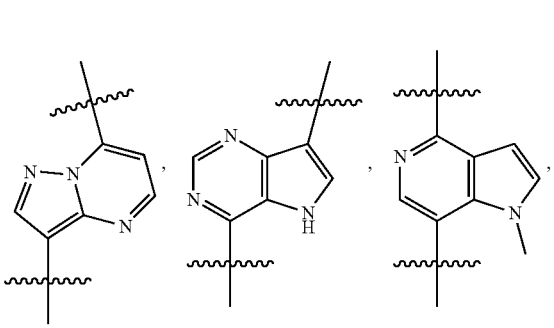

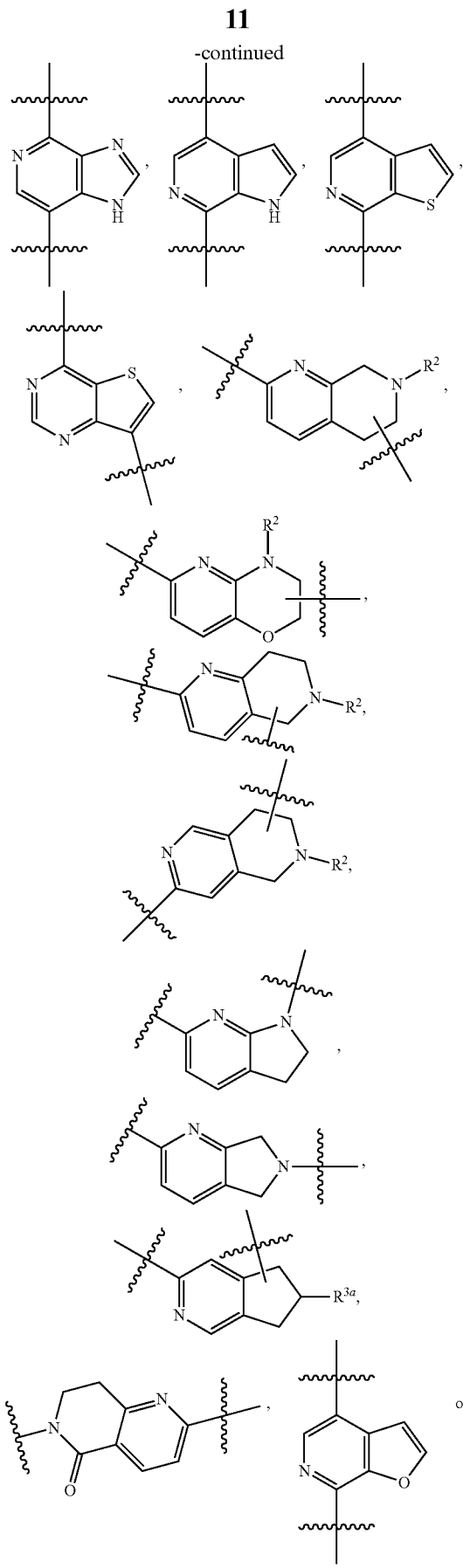

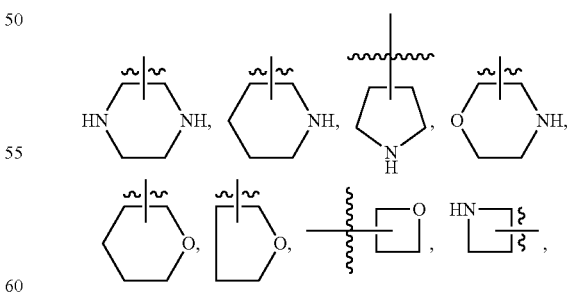

each moiety represented by A is independently and optionally substituted with one, two, three or four substituents independently selected from H, $C_{1-4}$ alkyl, F, Cl, Br, amino, hydroxy, carboxy, $C_{1-4}$ alkoxy, $C_{1-4}$ haloalkyl, $C_{1-4}$ alkylamino, amino-$C_{1-4}$-alkyl, $H-(C(R^3)_2)_n-O-C(=O)-(C(R^3)_2)_n-$, $(R^4)_2N-(C(R^3)_2)_n-$, $HO-(C(R^3)_2)_n-C(=O)-$, $N(R^4)_2-C(=O)-$, $HO-(C(R^3)_2)_n-$, $H-(C(R^3)_2)_n-O-(C(R^3)_2)_n-$, $H-(C(R^3)_2)_n-SO_2-(C(R^3)_2)_n-$, $H-(C(R^3)_2)_n-C(=O)-(C(R^3)_2)_n-$, $CN-(C(R^3)_2)_n-C(=O)-$, $H-(C(R^3)_2)_n-O-C(=O)-C(=O)-(C(R^3)_2)_n-$, cyano and nitro; and wherein $R^3$, $R^4$, $R^{3a}$, $R^2$ and n are as defined herein.

In some embodiments, each $R^{3a}$, $R^{3b}$ and $R^3$ is independently H, F, Cl, Br, hydroxy, carboxy, amino, trifluoromethyl, methyl, ethyl, propyl, butyl, cyclopropyl, cyclohexyl, cyclopentyl, $H-(CH_2)_n-O-(CH_2)_n-$, $N(R^4)_2-C(=O)-$, $H-(CH_2)_n-SO_2-(CH_2)_n-$, $H-O-(CH_2)_n-C(=O)-(CH_2)_n-$ or $N(R^4)_2-(CH_2)_n-$;

each $R^4$ is independently H, hydroxy, carboxy, amino, methoxy, aminomethyl, aminoethyl, $NH_2-C(=O)-$, trifluoromethyl, 2,2-difluoroethyl, methyl, ethyl, propyl or butyl; and wherein n is as defined herein.

In some embodiments, each $R^{1a}$, $R^1$ and $R^2$ is independently H, 3,3,3-trifluoropropyl, trifluoromethyl, 1,1-difluoroethyl, cyclopropyl, cyclohexyl, cyclopentyl, cyclobutyl, $H-(C(R^3)_2)_n-O-C(=O)-(C(R^3)_2)_n-$, $(R^4)_2N-(C(R^3)_2)_n-$, $HO-(C(R^3)_2)_n-C(=O)-$, $N(R^4)_2-C(=O)-$, $HO-(C(R^3)_2)_n-$, $H-(C(R^3)_2)_n-O-(C(R^3)_2)_n-$, $H-(C(R^3)_2)_n-SO_2-(C(R^3)_2)_n-$, $H-(C(R^3)_2)_n-C(=O)-(C(R^3)_2)_n-$, $CN-(C(R^3)_2)_n-C(=O)-$, $H-(C(R^3)_2)_n-O-C(=O)-C(=O)-(C(R^3)_2)_n-$, methyl, ethyl, propyl or butyl;

each $R^5$ is independently H, oxo(=O), methyl, ethyl, propyl, butyl, F, Cl, Br, amino, hydroxy, carboxy, methoxy, $C_{1-4}$ alkylamino, amino-$C_{1-4}$-alkyl, $N(R^4)_2-C(=O)-$, $CN-(C(R^3)_2)_n-C(=O)-$, trifluoromethyl, $H-(C(R^3)_2)_n-O-C(=O)-(C(R^3)_2)_n-$,

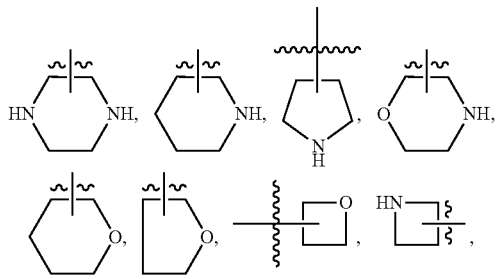

$C_{1-4}$ haloalkyl, $H-(C(R^3)_2)_n-O-C(=O)-C(=O)-(C(R^3)_2)_n-$, $H-(C(R^3)_2)_n-C(=O)-(C(R^3)_2)_n-$, $H-(C(R^3)_2)_n-O-(C(R^3)_2)_n-$, $H-(C(R^3)_2)_n-SO_2-(C(R^3)_2)_n-$, $H-(C(R^3)_2)_n-O-(C(R^3)_2)_{n1}-C(=O)-(C(R^3)_2)_n-$, cyano, cyclopropyl, cyclohexyl, cyclopentyl or nitro;

each $R^6$ is independently H, oxo(=O), methyl, ethyl, propyl, butyl, F, Cl, Br, amino, hydroxy, carboxy, methoxy, $C_{1-4}$ alkylamino, amino-$C_{1-4}$-alkyl, $N(R^4)_2-C(=O)-$, $CN-(C(R^3)_2)_n-C(=O)-$, $C_{1-4}$ haloalkyl, $H-(C(R^3)_2)_n-O-C(=O)-(C(R^3)_2)_n-$, $H-(C(R^3)_2)_n-O-C(=O)-C(=O)-(C(R^3)_2)_n-$, $H-(C(R^3)_2)_n-C(=O)-(C(R^3)_2)_n-$, $H-(C(R^3)_2)_n-SO_2-(C(R^3)_2)_n-$, $H-(C(R^3)_2)_n-O-(C(R^3)_2)_{n1}-C(=O)-C((R^3)_2)_n-$, $H-(C(R^3)_2)_n-O-(C(R^3)_2)_n-$, cyano, $C_{3-6}$ heterocyclyl, $C_{3-6}$ cycloalkyl or nitro; and wherein n1, $R^4$, $R^3$ and n are as defined herein.

In other aspect, provided herein is a pharmaceutical composition comprising the compound disclosed herein.

In some embodiments, the pharmaceutical composition disclosed herein further comprises at least one of pharmaceutically acceptable carriers, excipients, diluents, adjuvants, vehicles.

In some embodiments, the pharmaceutical composition disclosed herein further comprising an additional therapeutic agent, wherein the additional therapeutic agent is a chemotherapeutic drug, an antiproliferative agent, an immunosuppressor, an immunologic stimulant, an anti-inflammatory reagent, an agent for treating atherosclerosis, an agent for treating pulmonary fibrosis, a CDK4/6 inhibitor, an ABL inhibitor, an ABL/Scr inhibitor, an aurora kinase inhibitor, a non-ATP competitive inhibitor of BCR-ABL, a c-KIT mutation inhibitor, an RET inhibitor, a PDGFR inhibitor, a VEGFR inhibitor, a CSF1R inhibitor, an FLT3 inhibitor, an FLT3-ITD inhibitor or a combination thereof.

In some embodiments, the additional therapeutic agent of the pharmaceutical composition disclosed herein is chlorambucil, melphalan, cyclophosphamide, ifosfamide, busulfan, carmustine, lomustine, streptozotocin, cis-platinum, carboplatin, oxaliplatin, dacarbazine, temozolomide, procarbozine, methotrexate, fluorouracil, cytosine arabinoside, gemcitabine, purinethol, fludarabine, vinblastine, vincristine, vinorelbine, paclitaxel, docetaxel, topotecan, irinotecan, etoposide, trabectedin, dactinomycin, doxorubicin, pharmorubicin, daunomycin, mitoxantrone, bleomycin, mitomycin C, ixabepilone, tamoxifen, flutamide, gonadorelin analogue, megestrol acetate, prednisone, dexamethasone, methylprednisolone, thalidomide, interferon α, calcium folinate, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, zelboraf, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, cabozantinib, ponatinib, midostaurin, pacritinib, quizartinib, gilteritinib, AKN-028, AT-9283, crenolanib, ENMD-2076, famitinib, dovitinib, PLX-3397, palbociclib, abemaciclib, ribociclib, rigosertib sodium, selinexor, roniciclib, AT-7519, seliciclib, alvocidib or a combination thereof.

In other aspect, provided herein is use of the compound or the pharmaceutical composition disclosed herein in the manufacture of a medicament for preventing, managing, treating or lessening disorders or diseases caused by abnormal cell proliferation, autoimmunity, inflammation or infection.

In other aspect, provided herein is a method of preparing a medicament for preventing, managing, treating or lessening disorders or diseases caused by abnormal cell proliferation, autoimmunity, inflammation or infection by using the compound or the pharmaceutical composition disclosed herein.

In other aspect, provided herein is the compound or the pharmaceutical composition for use in preventing, managing, treating or lessening a disorder or disease caused by abnormal cell proliferation, autoimmunity, inflammation or infection.

In some embodiments of the use of the invention, the abnormal cell proliferation disorder or disease is ovarian cancer, cervical cancer, testiculoma, esophagus cancer, gastric cancer, skin cancer, lung cancer, osteocarcinoma, acute myeloid leukemia, chronic myelogenous leukemia, gastrointestinal stromal tumor, acute myelocytic leukemia (AML), chronic myeloid leukemia (CML) with mutation, acute lymphoblastic leukemia (ALL), colorectal cancer, gastric cancer, breast cancer, lung cancer, cancer of the liver, prostate cancer, pancreatic cancer, thyroid cancer, kidney cancer, brain tumor, cervical cancer, cancer of the central nervous system, spongioblastoma or myelodysplastic syndrome, atherosclerosis, pulmonary fibrosis, leukemia, lymph cancer, rheumatic disease, cryoglobulinemia, non-lymphoreticular system tumor, papular mucinosis, familial splenic anemia, multiple myeloma, amyloidosis, solitary plasmacytoma, heavy chain disease, light chain disease, malignant lymphoma, chronic lymphocytic leukemia, primary macroglobulinemia, semi-molecular disease, monocytic leukemia, primary macroglobulinemia purpura, secondary benign monoclonal gammopathy, osteolytic lesion, myeloma, lymphoblastoma, part of the non-Hodgkin's lymphoma, Sezary syndrome, infectious mononucleosis, acute histiocytosis, Hodgkin's lymphoma, hairy cell leukemia, colon cancer, rectal cancer, intestinal polyp, small cell lung cancer, neuroblastoma, neuroendocrine cell tumor, islet cell tumor, medullary thyroid carcinoma, melanoma, retinoblastoma, uterine cancer, head and neck squamous cell carcinoma, alimentary canal malignancy, non-small cell lung cancer, spongioblastoma, mantle cell lymphoma, chronic granulocytic leukemia, acute granulocytic leukemia, bladder cancer or myeloma.

In some embodiments of the use of the invention, the autoimmune disease is rheumatic arthritis, lupus, multiple sclerosis, thyroiditis, type I diabetes, sarcoidosis, inflammatory bowel disease, Crohn's disease or systemic lupus.

In some embodiments of the use of the invention, the inflammatory disease is diverticulitis, colitis, pancreatitis, hepatitis, chronic hepatitis, cirrhosis, cholecystitis or chronic inflammation.

In some embodiments of the use of the invention, the infection disease is virus infection or fungal infection.

In some embodiments of the use of the invention, the disorder or disease is a disease caused by a change in cyclin-dependent kinase.

In other embodiments of the use of the invention, the cyclin-dependent kinase is CDK1, CDK2, CDK4, CDK6 or CDK9.

In some embodiments of the method of the invention, the abnormal cell proliferation disorder or disease is ovarian cancer, cervical cancer, testiculoma, esophagus cancer, gastric cancer, skin cancer, lung cancer, osteocarcinoma, acute myeloid leukemia, chronic myelogenous leukemia, gastrointestinal stromal tumor, acute myelocytic leukemia (AML), chronic myeloid leukemia (CML) with mutation, acute lymphoblastic leukemia (ALL), colorectal cancer, gastric cancer, breast cancer, lung cancer, cancer of the liver, prostate cancer, pancreatic cancer, thyroid cancer, kidney cancer, brain tumor, cervical cancer, cancer of the central nervous system, spongioblastoma or myelodysplastic syndrome, atherosclerosis, pulmonary fibrosis, leukemia, lymph cancer, rheumatic disease, cryoglobulinemia, non-lymphoreticular system tumor, papular mucinosis, familial splenic anemia, multiple myeloma, amyloidosis, solitary plasmacytoma, heavy chain disease, light chain disease, malignant lymphoma, chronic lymphocytic leukemia, primary macroglobulinemia, semi-molecular disease, monocytic leukemia, primary macroglobulinemia purpura, secondary benign monoclonal gammopathy, osteolytic lesion, myeloma, lymphoblastoma, part of the non-Hodgkin's lymphoma, Sezary syndrome, infectious mononucleosis, acute histiocytosis, Hodgkin's lymphoma, hairy cell leukemia, colon cancer, rectal cancer, intestinal polyp, small cell lung cancer, neuroblastoma, neuroendocrine cell tumor, islet cell tumor, medullary thyroid carcinoma, melanoma, retinoblastoma, uterine cancer, head and neck squamous cell carcinoma, alimentary canal malignancy, non-small cell lung cancer, spongioblastoma, mantle cell lymphoma, chronic granulocytic leukemia, acute granulocytic leukemia, bladder cancer or myeloma.

In some embodiments of the method of the invention, the autoimmune disease is rheumatic arthritis, lupus, multiple sclerosis, thyroiditis, type I diabetes, sarcoidosis, inflammatory bowel disease, Crohn's disease or systemic lupus.

In some embodiments of the method of the invention, the inflammatory disease is diverticulitis, colitis, pancreatitis, hepatitis, chronic hepatitis, cirrhosis, cholecystitis or chronic inflammation.

In some embodiments of the method of the invention, the infection disease is virus infection or fungal infection.

In some embodiments of the method of the invention, the disorder or disease is a disease caused by changes in cyclin-dependent kinase.

In other embodiments of the method of the invention, the cyclin-dependent kinase is CDK1, CDK2, CDK4, CDK6 or CDK9.

In some embodiments of the compound or the pharmaceutical composition of the invention, the abnormal cell proliferation disorder or disease is ovarian cancer, cervical cancer, testiculoma, esophagus cancer, gastric cancer, skin cancer, lung cancer, osteocarcinoma, acute myeloid leukemia, chronic myelogenous leukemia, gastrointestinal stromal tumor, acute myelocytic leukemia (AML), chronic myeloid leukemia (CML) with mutation, acute lymphoblastic leukemia (ALL), colorectal cancer, gastric cancer, breast cancer, lung cancer, cancer of the liver, prostate cancer, pancreatic cancer, thyroid cancer, kidney cancer, brain tumor, cervical cancer, cancer of the central nervous system, spongioblastoma or myelodysplastic syndrome, atherosclerosis, pulmonary fibrosis, leukemia, lymph cancer, rheumatic disease, cryoglobulinemia, non-lymphoreticular system tumor, papular mucinosis, familial splenic anemia, multiple myeloma, amyloidosis, solitary plasmacytoma, heavy chain disease, light chain disease, malignant lymphoma, chronic lymphocytic leukemia, primary macroglobulinemia, semi-molecular disease, monocytic leukemia, primary macroglobulinemia purpura, secondary benign monoclonal gammopathy, osteolytic lesion, myeloma, lymphoblastoma, part of the non-Hodgkin's lymphoma, Sezary syndrome, infectious mononucleosis, acute histiocytosis, Hodgkin's lymphoma, hairy cell leukemia, colon cancer, rectal cancer, intestinal polyp, small cell lung cancer, neuroblastoma, neuroendocrine cell tumor, islet cell tumor, medullary thyroid carcinoma, melanoma, retinoblastoma, uterine cancer, head and neck squamous cell carcinoma, alimentary canal malignancy, non-small cell lung cancer, spongioblastoma, mantle cell lymphoma, chronic granulocytic leukemia, acute granulocytic leukemia, bladder cancer or myeloma.

In some embodiments of the compound or the pharmaceutical composition of the invention, the autoimmune disease is rheumatic arthritis, lupus, multiple sclerosis, thyroiditis, type I diabetes, sarcoidosis, inflammatory bowel disease, Crohn's disease or systemic lupus.

In some embodiments of the compound or the pharmaceutical composition of the invention, the inflammatory disease is diverticulitis, colitis, pancreatitis, hepatitis, chronic hepatitis, cirrhosis, cholecystitis or chronic inflammation.

In some embodiments of the compound or the pharmaceutical composition of the invention, the infection disease is virus infection or fungal infection.

In some embodiments of the compound or the pharmaceutical composition of the invention, the disorder or disease is a disease caused by changes in cyclin-dependent kinase.

In other embodiments of the compound or the pharmaceutical composition of the invention, the cyclin-dependent kinase is CDK1, CDK2, CDK4, CDK6 or CDK9.

In one aspect, provided herein is a drug combination comprising the compound or the pharmaceutical composition disclosed herein and one or more other activity agents used for treating proliferative diseases, autoimmune diseases or inflammatory diseases.

In some embodiments of the drug combination disclosed herein, the other activity agent is a chemotherapeutic drug, an antiproliferative agent, an immunosuppressor, an immunologic stimulant, an anti-inflammatory agent, a CDK4/6 kinase inhibitor, an ABL inhibitor, an ABL/Scr inhibitor, an aurora kinase inhibitor, a non-ATP competitive inhibitor of BCR-ABL, a c-KIT mutation inhibitor, an RET inhibitor, a PDGFR inhibitor, a VEGFR inhibitor, CSF1R inhibitor, an FLT3 inhibitor, an FLT3-ITD inhibitor or a combination thereof.

The compound of the invention is suitable as an active agent in a pharmaceutical composition, the pharmaceutical composition can be used in effectively treating especially diseases related to protein kinases, such as cancer, graft rejection and autoimmune disease. The pharmaceutical composition of each embodiment has a pharmaceutically effective active agent of the invention and other pharmaceutically acceptable excipient, carrier, filler, diluents, and the like. The term "pharmaceutically effective amount" as used herein indicates an amount necessary to administer to a host, or to a cell, issue, or organ of a host, to achieve a therapeutic result, especially the regulating, modulating, or inhibiting protein kinase activity, e.g., inhibition of the activity of a protein kinase, or treatment of cancer, graft rejection and autoimmune disease.

In addition, the present invention provides a method for inhibiting the activity of a protein kinase. The method includes contacting a cell with any of the compounds of the present invention. In a related embodiment, the method further provides that the compound is present in an amount effective to selectively inhibit the activity of a protein kinase.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entireties.

As used herein, the following definitions shall apply unless otherwise indicated. For purposes of this invention, the chemical elements are identified in accordance with the Periodic Table of the Elements, CAS version, and *the Handbook of Chemistry and Physics*, 75$^{th}$ Ed. 1994. Additionally, general principles of organic chemistry are described in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" is meant to be open ended, including the indicated component but not excluding other elements.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer is referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* (2nd Ed. Robert E. Gawley, Jeffrey Aubé, Elsevier, Oxford, UK, 2012); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972); *Chiral Separation Techniques: A Practical Approach* (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. If tautomerism could happen (such as in a solvent), the chemical balance between tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. The specific example of keto-enol tautomerisms is hexane-2,4-dione and 4-hydroxyhex-3-en-2-one tautomerism. Another example of tautomerisms is phenol-keto tautomerism. The specific example of phenol-keto tautomerisms is pyridin-4-ol and pyridin-4(1H)-one tautomerism. Unless otherwise stated, all tautomers of the present compounds are within the scope disclosed herein.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a give an structure can be substituted with more than one substituent selected from a specified group, the substituent may be either the same or different at each position. Substituent 1 may be, but not limited to oxo(=O), F, Cl, Br, I, hydroxy, amino, carboxy, alkyl, alkyl-S(=O)$_t$—, haloalkyl, hydroxyalkyl, aminoalkyl, formyl, aminoacyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkyl-(C=O)—, benzyl, cyclopropyl, phenyl, N(R$^4$)$_2$—C(=O)—, CN—(C(R$^3$)$_2$)$_n$—C(=O)—, H—(C(R$^3$)$_2$)$_n$—O—C(=O)—(C(R$^3$)$_2$)$_n$—, or alkoxyalkyl, and the like. In the case of reasonable, substituent 1 may be further substituted with one or more, same or different substituent 2. Substituent 2 may be, but not limited to oxo(=O), F, Cl, Br, I, hydroxy, amino, carboxy, alkyl, alkyl-S(=O)$_t$—, haloalkyl, hydroxyalkyl, aminoalkyl, formyl, aminoacyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkyl-(C=O)—, benzyl, cyclopropyl, phenyl, N(R$^4$)$_2$—C(=O)—, CN—(C(R$^3$)$_2$)$_n$—C(=O)—, H—(C(R$^3$)$_2$)$_n$—O—C(=O)—(C(R$^3$)$_2$)$_n$—, or alkoxyalkyl, and the like. wherein t is 0, 1 or 2; n, R$^3$ and R$^4$ are as defined herein.

The term "alkyl" or "alkyl group" refers to a saturated linear or branched-chain monovalent hydrocarbon radical of 1 to 20 carbon atoms, wherein the alkyl radical may be optionally and independently substituted with one or more substituents described herein. In some embodiments, the alkyl group contains 1-10 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms. Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), 2-methyl-propyl or isobutyl (i-Bu, —CH$_2$CH(CH$_3$)$_2$), 1-methyl-propyl or sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, n-heptyl and n-octyl, etc. The term "alkyl" or the prefix "alk-" is inclusive of both straight chain and branched saturated carbon chain. The alkyl group can be substituted by a substituent disclosed herein.

The term "haloalkyl" refers to an alkyl group substituted with one or more identical or different halogen atoms.

Wherein the alkyl group is as defined herein. Some non-limiting examples of the haloalkyl group include trifluoromethyl, 2,2-difluoroethyl, 3,3,3-trifluoropropyl, and the like. The haloalkyl group can be substituted by a substituent disclosed herein.

The term "amino" refers to —$NH_2$.

The term "aminoalkyl" refers to a group having R'R" N-alkyl, wherein each of R' and R" is independently H, alkyl or haloalkyl. Which refers to an alkyl group substituted with one or more identical or different amino groups. Wherein the alkyl group is as defined herein. The aminoalkyl group can be substituted by a substituent disclosed herein.

The term "aminoacyl" refers to a group having R'R" N—C(=O)—, wherein each of R' and R" is independently H, alkyl or haloalkyl.

The term "alkamino" or "alkylamino" refers to "N-alkylamino" and "N,N-dialkylamino", wherein the amino groups are independently substituted with one or two alkyl groups, respectively, and wherein the alkyl group is as defined herein. In some embodiments, the alkylamino radical is "lower alkylamino" radical having one or two $C_{1-6}$ alkyl groups attached to a nitrogen atom. In other embodiments, the alkylamino radical is "lower alkylamino" radical having one or two $C_{1-3}$ alkyl groups attached to a nitrogen atom. Some non-limiting examples of suitable alkylamino radical include mono or dialkylamino. Some examples include, but not limited to, N-methylamino, N-ethylamino, N,N-dimethylamino and N,N-diethylamino, and the like. The alkylamino group can be substituted by a substituent disclosed herein.

The term "alkoxy" refers to an alkyl group, as defined herein, attached to the principal carbon chain through an oxygen atom. Some non-limiting examples of the alkoxy group include methoxy, ethoxy, propoxy, and the like. The alkoxy group can be substituted by a substituent disclosed herein.

The term "cycloalkyl" or "carbocycle" refers to a monovalent or multivalent, non-aromatic, saturated or partially unsaturated ring consisting solely of carbon and hydrogen atoms and including 3-12 carbon atoms as a monocyclic ring or 7-12 carbon atoms as a bicyclic ring or tricyclic ring. Bicyclic carbocycles having 7-12 ring atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of the cycloaliphatic group include cycloalkyl, cycloalkenyl and cycloalkynyl. Further examples of the cycloaliphatic group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantly, and the like. Depending on the structure, the cycloalkyl group can be a monoradical or a diradical, i.e., cycloalkylene. $C_4$ cycloalkyl refers to cyclobutyl, $C_5$ cycloalkyl refers to cyclopentyl, $C_7$ cycloalkyl refers to cycloheptyl. The cycloalkyl group can be substituted by a substituent disclosed herein.

The term "aryl" refers to monocyclic, bicyclic and tricyclic carbocyclic ring systems, wherein at least one ring in the system is aromatic, and wherein each ring in the system contains 3 to 7 ring members, and just have one attachment connected with the rest of the molecular. The term "aryl" may be used interchangeably with the term "aryl ring" or "aromatic ring". Some non-limiting examples of the aryl group include phenyl, naphthyl and anthracene. Depending on the structure, the aryl group can be a monoradical or a diradical such as an arylene group. The aryl group can be substituted by a substituent disclosed herein.

The term "heteroaryl" or "heteroaryl ring" as used interchangeably herein, refers to a monocyclic, bicyclic, tricyclic or tetracyclic ring system, wherein the bicyclic heteroaryl, tricyclic heteroaryl or tetracyclic heteroaryl ring system is fused to form a ring. Wherein at least one ring of the heteroaryl ring system is aromatic, in which one or more ring members are an independently selected heteroatom (heteroatoms selected from N, O, P and S, wherein the S or P is optionally substituted with one or more oxo to provide the group SO or $SO_2$, PO or $PO_2$). The heteroaryl system may be attached to the main structure at any heteroatom or carbon atom which results in the creation of a stable compound. The heteroaryl system group may be 3-7 membered monocyclic ring, 7-10 membered bicyclic ring or 10-15 membered tricyclic ring. Bicyclic heteroaryl ring having 7-10 ring atoms can be arranged as a bicyclo[4,5], [5,5], [5,6] or [6,6] system, and tricyclic heteroaryl ring having 10 or 15 ring atoms can be arranged as a tricyclo[5,5,6], [5,7,6] or [6,5,6] system.

Some non-limiting examples of the heteroaryl system (including heteroaryl and heteroaromatic ring) include furan-2-yl, furan-3-yl, imidazol-N-yl, imidazol-2-yl, imidazol-4-yl, imidazol-5-yl, isoxazol-3-yl, isoxazol-4-yl, isoxazol-5-yl, oxazol-2-yl, oxazol-4-yl, oxazol-5-yl, 4-methylisoxazol-5-yl, pyrrol-N-yl, pyrrol-2-yl, pyrrol-3-yl, pyrid-2-yl, pyrid-3-yl, pyrid-4-yl, pyrimidin-2-yl, pyrimidin-4-yl, pyrimidin-5-yl, pyridazinyl (e.g., pyridazin-3-yl), thiazol-2-yl, thiazol-4-yl, thiazol-5-yl, tetrazolyl (e.g., tetrazol-5-yl), triazolyl (e.g., triazol-2-yl and triazol-5-yl), thien-2-yl, thien-3-yl, pyrazolyl (e.g., pyrazol-2-yl), isothiazolyl, oxazolopyridinyl, oxiranyl, perimidinyl, phenanthridinyl, phenanthrolinyl, phenarsazinyl, phenazinyl, phenothiazinyl, phenoxazinyl, phthalazinyl, pteridinyl, pyridopyridyl, quinazolinyl, thiophenyl, triazinyl, imidazo[2',1':2,3]thiazolo [4,5-b]pyrazinyl, imidazo[2',1':2,3]thiazolo[4,5-c]pyrazinyl, 1H-benzo[f]imidazo[4,5-b][1,4]thiazepinyl, and the like. The heteroaryl group can be substituted by a substituent disclosed herein.

The term "heterocyclyl", "heterocycle", "heterocycloaliphatic" or "heterocyclic" as used interchangeably herein refers to a monocyclic, bicyclic, tricyclic or tetracyclic ring system in which one or more ring members are an independently selected heteroatom and that is completely saturated or that contains one or more units of unsaturation, but which is not aromatic. The heterocyclyl system may be attached to the main structure at any heteroatom or carbon atom which results in the creation of a stable compound. One or more hydrogen atoms on the heterocyclic ring are optionally substituted with one or more substituents described herein. In some embodiments, the heterocyclyl, heterocycle, heterocycloaliphatic or heterocyclic group is a monocyclic ring having 3-7 ring members (e.g., 1 to 6 carbon atoms and 1 to 3 heteroatoms selected from N, O, P and S, wherein the S or P is optionally substituted with one or more oxo to provide the group SO or $SO_2$, PO or $PO_2$, and the —$CH_2$— can also be optionally replaced by the group —C=O—, with the proviso that when the ring is a 3-membered ring, there is only one heteroatom) or a bicyclic ring having 7-10 ring members (e.g., 4 to 9 carbon atoms and 1 to 3 heteroatoms selected from N, O, P and S, wherein the N, S or P is optionally substituted with one or more oxo to provide the group NO, $NO_2$, SO or $SO_2$, PO or $PO_2$, and the —$CH_2$— can also be optionally replaced by the group —C=O—).

The "heterocyclyl" may be a carbon radical or heteroatom radical. The heterocyclyl group also includes a group in which the heterocyclyl group is fused with a saturated or partially unsaturated carbon ring or a heterocyclic ring. Some non-limiting examples of the heterocyclyl group include pyrrolidinyl, tetrahydrofuranyl, dihydrofuranyl, tetrahydrothienyl, tetrahydropyranyl, dihydropyranyl, tetrahydrothiopyranyl, piperidyl, thioxayl, azetidinyl, oxetanyl, thietanyl, piperidinyl, homopiperidinyl, epoxypropyl, azepanyl, oxepanyl, thiepanyl, morpholin-N-yl, morpholin-2-yl, morpholin-3-yl, thiomorpholinyl, piperazin-N-yl, piperazin-2-yl, piperazin-3-yl, homopiperazinyl, 1,2,3,6-tetrahydropyrid-1-yl, oxazepinyl, diazepinyl, thiazepinyl, pyrrolin-1-yl, pyrrolin-2-yl, pyrrolin-3-yl, dihydroindolyl, 2-indolinyl, 2H-pyranyl, 4H-pyranyl, dioxanyl, 1,3-dioxolanyl, dithianyl, dithiolanyl, dihydrothienyl, imidazolidinyl, 1,2,3,4-tetrahydroisoquinolinyl, 1,2,6-thiadiazine-1,1-dioxo-2-yl, hexahydro-2H-[1,4]dioxin[2,3-c]pyrrolyl, quinolizinyl, 1,1-dioxothiomorpholinyl, 2,3,3a,7a-tetrahydro-1H-isoindolyl, isoindolinyl, 1,2,3,4-tetrahydroquinolyl, dihydrobenzisothiazinyl, dihydrobenzisoxazinyl, dioxolanyl, dihydropyrazinyl, dihydropyridyl, dihydropyrazolyl, dihydropyrimidinyl, dihydropyrrolyl, 1,4-dithianyl, furanone-yl, furyl, imidazolidinyl, imidazolinyl, imidazolyl, imidazopyridyl, imidazothiazolyl, indazolyl, dihydroindolyl, indolizinyl, indolyl, isobenzotetrahydrofuryl, isobenzotetrahydrothianthrenyl, isobenzodihydropyranyl, isocoumarinyl, isoindolinyl, isothiazolidinyl, isooxazolidinyl, morpholinyl, decahydroindolyl, decahydroisoindolyl, oxazolidenedione-yl, oxazolidinyl, epoxyethyl, piperazinyl, piperidinyl, 4-oxopiperidin-1-yl, pyrazolidinyl, quinuclidinyl, tetrahydroisoquinolinyl, tetrahydrothianthrenyl, thiomorpholinyl, thiazolidinyl, 1,3,5-trithianyl, 2-oxopyrrolidyl, oxo-1,3-thiazolidinyl, 2-(4-oxopiperidin-1-yl), 3,5-dioxopiperidyl, indolinyl, 1,2,3,4-tetrahydroisoquinolyl, 1,3-benzodioxlyl, 2-oxa-5-azabicyclo[2.2.1]hept-5-yl, 4-oxomorpholinyl and pyrimidinedione-yl, and the like.

In one embodiment, heterocyclyl may be 4-7 membered heterocyclyl, which refers to a saturated or partially unsaturated monocyclic ring containing 4-7 ring atoms, of which at least one ring atom is selected from nitrogen, sulfur and oxygen. Examples of the heterocyclyl group containing 4-7 ring atoms include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl and thiazepinyl, and the like. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limited examples of heterocyclyl wherein the ring sulfur atom is oxidized is sulfolanyl, 1,1-dioxo-thiomorpholinyl. The heterocyclyl group containing 4-7 ring atoms may be optionally substituted with one or more substituents disclosed herein.

The term "spirocyclyl", "spirocyclic", "spiro bicyclyl" or "spiro bicyclic" refers to a ring originating from a particular annular carbon of another ring. For example, as depicted below, a saturated bridged ring system (ring D and B') is termed as "fused bicyclic", whereas ring A and ring D share an atom between the two saturated ring system, which terms as a "spirocyclyl" or "spiro bicyclyl". Each cyclic ring in a spirocyclyl can be either a carbocyclic or a heteroalicyclic. Some non-limiting examples of the spiro bicyclyl group include spiro[2.4]heptyl, spiro[4.4]nonyl, and the like.

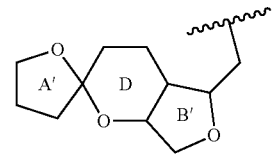

The term "spiro heterobicyclyl" refers to a ring originating from a particular annular carbon of another ring. For example, as depicted above, a saturated bridged ring system (ring D and B') is termed as "fused bicyclic", whereas ring A and ring D share an atom between the two saturated ring system, which terms as a "spirocyclyl". And at least one ring in the system contains one or more heteroatoms, wherein each ring in the system contains 3 to 7 ring members and that contains 1 to 6 carbon atoms and 1 to 3 heteroatoms selected from N, O, P and S, wherein the N, S or P is optionally substituted with one or more oxo to provide the group NO, NO$_2$, SO, SO$_2$, PO, PO$_2$, and the —CH$_2$— can also be optionally replaced by the group —C=O—. Some non-limiting examples of the spiro heterobicyclyl group include 4-azaspiro[2.4]heptyl, 4-oxaspiro[2.4]heptyl, 5-azaspiro[2.4]heptyl, 2-azaspiro[4.5]decyl, 2-azaspiro[3.3]heptyl, 2-azaspiro[4.4]nonyl, 3-azaspiro[5.4]decyl, 2-oxa-6-azaspiro[3.3]heptyl, 2,6-diazaspiro[3.3]heptyl, 2-thia-6-azaspiro[3.3]heptyl 2-oxide, 2-thia-6-azaspiro[3.3]heptyl 2,2-dioxide, 2,8-diazaspiro[4.5]decyl, 2,7-diazaspiro[4.4]octyl, 2,7-diazaspiro[4.5]decyl, 2,6-diazaspiro[4.5]decyl, 2,8-diazaspiro[4.5]dec-3-one-yl, 1,8-diazaspiro[4.5]decyl, 1,7-diazaspiro[4.4]nonyl, 1,7-diazaspiro[4.4]non-6-one-yl, 2,9-diazaspiro[5.5]hendec-1-one-yl, 1-oxa-3,8-diazaspiro[4.5]dec-2-one-yl, 1-oxa-3,7-diazaspiro[4.5]dec-2-one-yl, 2,6-diazaspiro[3.4]octyl, 2,5-diazaspiro[3.5]nonyl, 2,6-diazaspiro[3.3]heptyl, 2-oxa-7-azaspiro[3.5]nonyl, 2-oxa-6-azaspiro[3.4]octyl, and the like. Depending on the structure, the spiro heterobicyclyl group can be a monoradical or a diradical, i.e., spiro heterobicyclylene. The spiro heterocyclyl group can be substituted by a substituent disclosed herein.

The term "fused bicyclic", "fused cyclic", "fused bicyclyl" or "fused cyclyl" refers to a saturated or unsaturated fused ring system, which refers to a bicyclic ring system that is not aromatic and includes at least one non-aromatic ring. Such a system may contain isolated or conjugated unsaturation, but not aromatic or heteroaromatic rings in its core structure (but may have aromatic substitution thereon). Each cyclic ring in the fused bicyclyl can be either a carbocyclic ring or a heteroalicyclic ring. Some non-limiting examples of the fused bicyclic ring system include hexahydro-furo[3,2-b]furanyl, 2,3,3a,4,7,7a-hexahydro-1H-indenyl, 7-azabicyclo[2.2.1]heptyl, fused bicyclo[3.3.0]octyl, fused bicyclo[3.1.0]hexyl, 1,2,3,4,4a,5,8,8a-octahydronaphthyl, and the like.

The term "fused heterobicyclic" refers to a saturated or unsaturated fused ring system, which refers to a bicyclic ring system that is not aromatic and includes at least one non-aromatic ring. Such a system may contain isolated or conjugated unsaturation, but not aromatic or heteroaromatic rings in its core structure (but may have aromatic substitution thereon). And at least one ring in the fused ring system contains one or more heteroatoms. Each ring in the fused ring system contains 3 to 7 ring members and that contains 1 to 6 carbon atoms and 1 to 3 heteroatoms selected from N, O, P and S, wherein the N, S or P is optionally substituted with one or more oxo to provide the group NO, NO$_2$, SO or SO$_2$, PO or PO$_2$, and the —CH$_2$— can also be optionally replaced by the group —C=O—. Some non-limiting examples of the fused heterobicyclyl group include hexahydro-2H-[1,4]dioxin[2,3-c]pyrrolyl, 3-azabicyclo[3.3.0]octyl, 3-methyl-3,7-diazabicyclo[3.3.0]octyl, 8-azabicyclo[4.3.0]nonyl, 8-azabicyclo[4.3.0]non-3-yl, 3-azabicyclo[4.3.0]non-3-yl, 1,5-dioxa-8-azabicyclo[4.3.0]nonyl, (1R,6S)-2,5-dioxa-8-azabicyclo[4.3.0]nonyl, (1R,6R)-2,5-dioxa-8-azabicyclo[4.3.0]nonyl, isoindolinyl, 1,2,3,4-tetrahydroquinolyl, (1S,5S)-1-hydroxy-3-azabicyclo[3.1.0]hexyl, (1R,5S)-1-hydroxy-3-azabicyclo[3.1.0]hexyl, 3-aza-7-oxabicyclo[3.3.0]octyl, 3,7-diazabicyclo[3.3.0]octyl, 2,6-diazabicyclo[3.3.0]octyl, 2,7-diazabicyclo[3.3.0]octyl, 2,8-diazabicyclo[4.3.0]nonyl, 3,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 2-oxo-3-oxa-8-azabicyclo[4.3.0]nonyl, 3-oxo-2,4,8-triazabicyclo[4.3.0]nonyl, 3-oxo-4-oxa-2,8-diazabicyclo[4.3.0]nonyl, 3-oxo-2,8-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, 5,6-dihydro-4H-pyrrolo[3,4-c]isoxazolyl, [1,2,4]triazolo[4,3-a]piperidyl, isoxazolo[4,3-c]piperidinyl, 4,5,6,7-tetrahydroisoxazolo[3,4-c]pyridinyl, [1,2,4]triazolo[4,3-a]piperazinyl, 2-oxo-3-oxa-8-azabicyclo[4.3.0]nonyl, 2-oxa-7-azabicyclo[4.4.0]decyl, 1,5-dioxa-9-azabicyclo[4.4.0]decyl, 3-azabicyclo[4.4.0]decyl, 2,7-diazadecahydronaphthyl, 2-oxa-8-azabicyclo[4.4.0]decyl, hexahydropyrrolo[1,2-a]pyrazin-1(2H)-one-yl, decahydro-1H-pyridino[1,2-a]pyrazin-1-one-yl, 3-azabicyclo[3,1,0]hex-1-amino-yl, and the like. The fused heterobicyclyl group can be substituted by a substituent disclosed herein.

The term "bridged bicyclyl" refers to a saturated or unsaturated bridged ring system, which refers to a bicyclic ring system that is not aromatic. Such a system may contain isolated or conjugated unsaturation, but not aromatic rings in its core structure (but may have aromatic substitution thereon). In which each ring contains 3 to 7 ring members. Some non-limiting examples of the bridged bicyclyl group include bicyclo[2.2.1]heptyl, 2-methyl-heterobicyclo[2.2.1] heptyl, and the like.

The term "bridged bicyclyl" refers to a saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon). And at least one ring in the system contains one or more heteroatoms, wherein each ring in the system contains 3 to 7 ring members and that contains 1 to 6 carbon atoms and 1 to 3 heteroatoms selected from N, O, P and S, wherein the N, S or P is optionally substituted with one or more oxo to provide the group NO, NO$_2$, SO or SO$_2$, PO or PO$_2$, the —CH$_2$— group is optionally replaced by —C(=O)—. Some non-limiting examples of the such group include 2-oxa-5-azabicyclo[2.2.1]heptyl, 2-thia-5-azabicyclo[2.2.1]heptyl, 2-oxo-5-azabicyclo[2.2.1]heptyl, 2,5-diazabicyclo[2.2.1]heptyl, (1S,4S)-diazabicyclo[2.2.1]heptyl, 3,8-diazabicyclo[3.2.1]octyl, (1S,5S)-3,8-diazabicyclo[3.2.1]octyl, 1,4-diazabicyclo[3.2.2]nonan-3-one-yl, 8-oxa-3-azabicyclo[3.2.1]octyl, and the like. The bridged heterobicyclyl group can be substituted by a substituent disclosed herein.

The terms "spiro heterobicyclyl-NH—", "bridged heterobicyclyl-NH—", "fused heterobicyclyl-NH—", respectively refer to spiro heterobicyclyl, bridged heterobicyclyl and fused heterobicyclyl, wherein spiro heterobicyclyl, bridged heterobicyclyl and fused heterobicyclyl are as defined herein. Some non-limiting examples include N-3-azabicylclo[3.1.0]hexylamino, N-3-azabicylclo[4.4.0]decylamino, and the like.

"Anti-proliferation agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Bevacizumab) or any other cytotoxic agents, (estramustine phosphate, prednimustine), hormones or hormone agonists, antagonists, partial agonists or partial antagonists, kinase inhibitors, and radiation treatment.

As described herein, a bond drawn from a substituent R' to the center of one ring within a ring system represents substitution of the substituent R' at any substitutable position on the ring. For example, Formula a represents possible substitution of the substituent R' in any of the position on ring A' or ring B', as shown in Formula b, Formula c, Formula d, Formula e, Formula f, Formula g and Formula h.

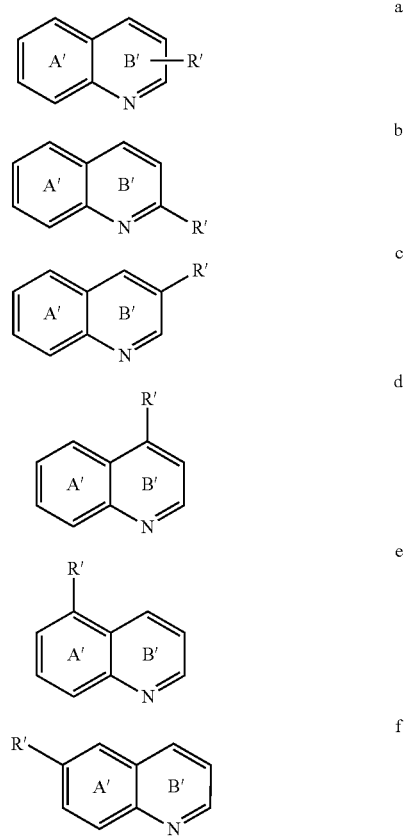

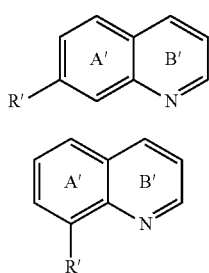

g h

As described herein, the attachment point can attach to the rest of the molecule at any attachable position on the rings. For example, Formula i represents attaching at any attachable position on ring A' or ring B'.

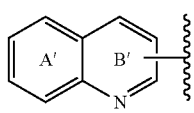

(i)

As described herein, two attachment points within a ring system. For example, either E or E' on ring C as shown in Formula j, can attach to the rest of the molecule and can be used interchangeably with each other.

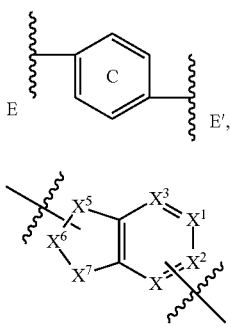

(j)

(y)

As described herein, the attachment point can attach to the rest of the molecule at any attachable position on the rings; the two attachment points can be interchanged. For example, Formula y represents attaching at any attachable position on the rings, and the two attachment points can be used interchangeably with each other.

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals. For example, the specific options of $R^3$ of "H—$(C(R^3)_2)_n$—O—$(C(R^3)_2)_{n1}$—C(=O)—$(C(R^3)_2)_n$—" are independent of each other; meanwhile, the specific options of multiple n are independent of each other, The sign "=" refers to a single bond "—" or a double bond "=" disclosed herein.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Stereochemical definitions and conventions used herein generally follow Parker et al., *McGraw-Hill Dictionary of Chemical Terms* (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

"Isomers" refers to different compounds having same molecular formula. "Stereisomer" refers to isomers differ in just spatial arrangement of atoms. The term isomers as used herein embrace any and all geometric isomers and stereoisomers. For example, "isomers" include cis- and trans-isomer, E- and Z-isomer, R- and S-enantiomer, diastereoisomer, (d)-isomer, (l)-isomer, racemic mixture thereof, as well as other mixtures fall in the scope of the invention.

A "hydrate" refers to a compound disclosed herein or a salt thereof, which further includes a stoichiometric or non-stoichiometric amount of water bound by non-covalent intermolecular forces, and also refers to the complex where the solvent molecule is water.

A "solvate" refers to an association or complex of one or more solvent molecules and a compound disclosed herein. Some non-limiting examples of the solvent that form solvates include water, isopropanol, ethanol, methanol, DMSO, ethyl acetate, acetic acid and ethanolamine.

An "ester" refers to an in vivo hydrolysable ester of a compound of the Formula (I)-(III) containing hydroxy group. For example, a pharmaceutically acceptable ester which is hydrolysed in the human or animal body to produce the parent alcohol. Some non-limiting examples of in vivo hydrolysable ester forming groups for hydroxy include phosphate, acetoxymethoxy, 2,2-dimethylpropionyloxymethoxy, alkanoyl, benzoyl, phenylacetyl, alkoxycarbonyl, dialkylcarbamoyl, N-(dialkylaminoethyl)-N-alkylcarbamoyl, and the like.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistry, by Jerry March, $4^{th}$ Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane Compounds of may exist in a number of different geometric isomeric, and tautomeric forms and references to compounds of the Formula (I) to (III) include all such forms. For the avoidance of doubt, where a compound can exist in one of several geometric isomeric or tautomeric forms and only one is specifically described or shown, all others are nevertheless embraced by Formula (I) to (III).

The term "prodrug" refers to a compound that is transformed in vivo into a compound of Formula (I)-(III). Such a transformation can be affected, for example, by hydrolysis of the prodrug form in blood or enzymatic transformation to the parent form in blood or tissue. Prodrugs of the compounds disclosed herein may be, for example, esters. Esters that may be utilized as prodrugs in the present invention are phenyl esters, aliphatic ($C_{1-24}$) esters, acyloxymethyl esters, carbonates, carbamates, and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in Higuchi et al., Pro-drugs as Novel Delivery Systems, Vol. 14 of the A.C.S. Symposium Series, Edward B. Roche, et al. ed., Bioreversible Carriers in Drug Design, American Pharmaceutical Association and Pergamon Press, 1987; Rautio et al., Prodrugs: Design and Clinical Applications, *Nature Review Drug Discovery*, 2008, 7, 255-270, and Hecker et al., Prodrugs of Phosphates and Phosphonates, *J. Med. Chem.*, 2008, 51, 2328-2345, all of which are incorporated herein by reference in their entireties.

Unless otherwise stated, all tautomers of the present compounds within the scope disclosed herein.

Additionally, unless otherwise stated, structures depicted herein are also meant to include compounds that differ only in the presence of one or more isotopically enriched atoms. The present invention includes isotopically-labeled compounds, which are identical to those recited in Formula (I)-(III), but that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, and chlorine, such as $^2H$, $^3H$, $^{13}C$, $^{11}C$, $^{14}C$, $^{15}N$, $^{31}P$, $^{32}P$, $^{35}S$, $^{18}F$ and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ or $^{14}C$ are incorporated, are useful in drug and/or substrate tissue distribution assays. Isotopically labeled compounds of Formula (I)-(III) of this invention and prodrugs thereof can generally be prepared by carrying out the procedures disclosed in the Schemes and/or in the Examples below, by substituting a readily available isotopically labeled reagent for a non-isotopically labeled reagent.

The term "metabolite" refers to a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

The compounds disclosed herein are useful in various pharmaceutically acceptable salt forms. The term "pharmaceutically acceptable salt" refers to those salt forms which would be apparent to the pharmaceutical chemist, i.e., those which are substantially nontoxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The term "pharmaceutically acceptable salt" disclosed herein refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences*, 1977, 66: 1-19, which is incorporated herein by reference. Examples of pharmaceutically acceptable, nontoxic salts include, but are not limited to, salts of an amino group formed with inorganic acids such as hydrochloric acid, hydrobromic acid, phosphoric acid, sulfuric acid, perchloric acid and nitric acid or with organic acids such as acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid or salts obtained by using other methods used in the art such as ion exchange.

Other pharmaceutically acceptable salts include adipate, malate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4}$ alkyl$)_4$ salts.

This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, ferric salt, zinc salt, copper salt, manganese salt, aluminium salt, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate. Amine salts include, but are not limited to, N,N'-dibenzylethylenediamine, chloroprocaine, choline, ammonia, diethanolamine and other hydroxyalkylamine, ethylenediamine, N-methylglucamine, procaine, N-benzylphenethylamine, 1-para-chlorobenzyl-2-pyrrolidin-1'-ylmethylbenzimidazole, diethylamine and other alkylamine, piperazine and tris(hydroxymethyl)aminomethane. Alkali earth metal salts include, but are not limited to, barium, calcium and magnesium. Transition metal salts include, but are not limited to, zinc.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl) ethoxy-methy-1, 2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991; and P. J. Kocienski, *Protecting Groups*, Thieme, Stuttgart, 2005.

In the present invention, if the chemical name of the compound doesn't match the corresponding structure, the compound is characterized by the corresponding structure.

As used herein, the abbreviations for any protective groups, amino acids and other compounds are, unless otherwise indicated, in accord with their common usage, recognized abbreviations, or the IUPAC-IUB Commission on Biochemical Nomenclature (See, *Biochem.* 1972, 11: 942-944).

Description of Compounds of the Invention

There remain needs for a large number of new therapies and drugs used for treating or preventing or improving disorders related to protein kinases, as well as compounds used for treating, preventing, or improving one or more of cancer, autoimmune diseases and infection diseases. The compounds provided herein can be used in regulating the activities of protein kinases such as CDKs, especially regulating or inhibiting the activities of CDK4 or CDK6.

In one aspect, provided herein is a compound having Formula (I) or a stereoisomer, a geometric isomer, a tautomer, an N-oxide, a hydrate, a solvate, an ester, a metabolite, a pharmaceutically acceptable salt or a prodrug thereof,

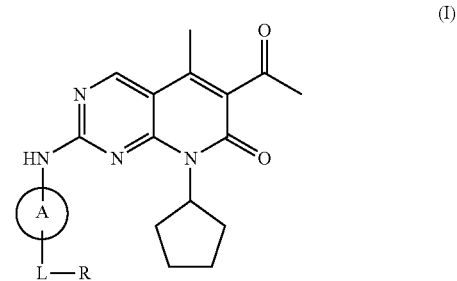

(I)

wherein L is a bond, —$(C(R^{3b})_2)_n$—, —$N(R^1)$—$(C(R^{3b})_2)_n$—, —O—$(C(R^{3b})_2)_n$—, —C(=O)—$(C(R^{3b})_2)_n$—, —$(CH_2)_n$—, —$N(R^1)$—$(CH_2)_n$—, —C(=O)—$N(R^1)$—$(CH_2)_n$—, —O—$(CH_2)_n$—, —$S(=O)_m$— or —C(=O)—$(CH_2)_n$—;

1) ring A is

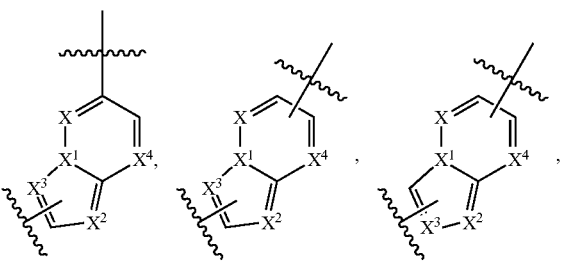

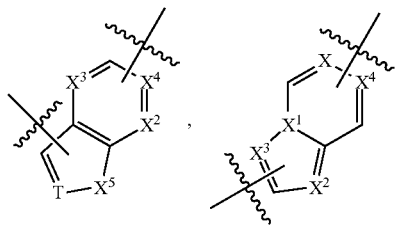

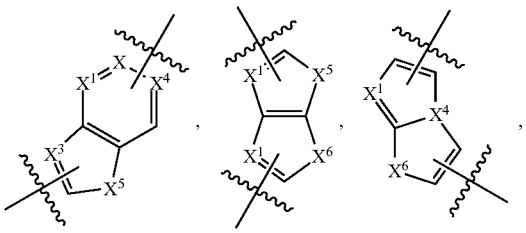

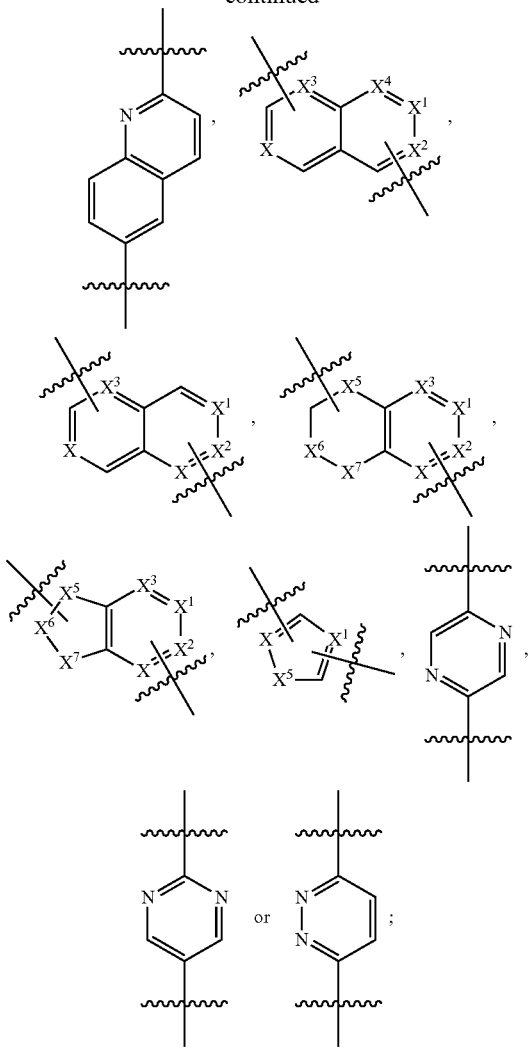

wherein when ═ is a double bond, T is X,

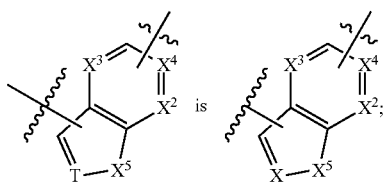  is 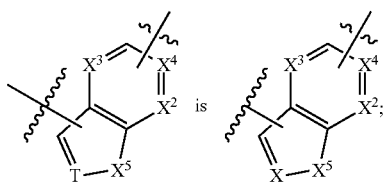

when ═ is a single bond, T is $X^6$,

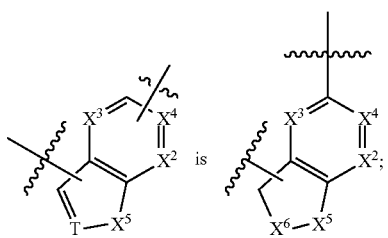  is 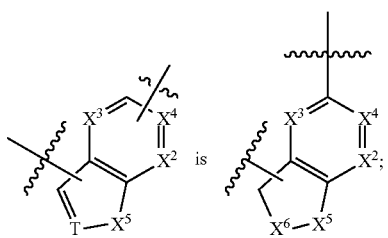

R is $C_{5-11}$ spiro heterobicyclyl, $C_{5-11}$ bridged heterobicyclyl, $C_{5-11}$ fused heterobicyclyl, $C_{3-9}$ cycloalkyl, $C_{2-9}$ heterocyclyl or $C_{1-9}$ heteroaryl;

or 2)

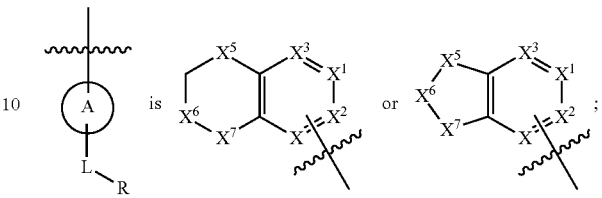

wherein each $X^7$, $X^5$ and $X^6$ is independently —$C(R^{3a})_2$—, —$N(R^2)$—, —O—, —S(═O)$_m$— or —C(═O)—;

each X, $X^1$, $X^2$, $X^3$ and $X^4$ is independently $CR^{3a}$ or N;

each n is independently 0, 1, 2, 3, or 4;

each n1 is independently 1, 2, or 3;

each m is independently 0, 1, or 2;

each $R^{1a}$, $R^1$ and $R^2$ is independently H, $C_{1-4}$ haloalkyl, H—$(C(R^3)_2)_n$—O—C(═O)—$(C(R^3)_2)_n$—, $(R^4)_2$N—$(C(R^3)_2)_n$—, HO—$(C(R^3)_2)_n$—C(═O)—, $N(R^4)_2$—C(═O)—, HO—$(C(R^3)_2)_n$—, H—$(C(R^3)_2)_n$—O—$(C(R^3)_2)_n$—, H—$(C(R^3)_2)_n$—SO$_2$—$(C(R^3)_2)_n$—, H—$(C(R^3)_2)_n$—C(═O)—$(C(R^3)_2)_n$—, CN—$(C(R^3)_2)_n$—C(═O)—, H—$(C(R^3)_2)_n$—O—C(═O)—C(═O)—$(C(R^3)_2)_n$—, $C_{3-9}$ cycloalkyl, $C_{2-9}$ heterocyclyl, $C_{1-9}$ heteroaryl or $C_{1-4}$ alkyl;

each $R^{3a}$, $R^{3b}$ and $R^3$ is independently H, F, Cl, Br, $C_{1-4}$ alkyl, hydroxy, carboxy, amino, $C_{3-9}$ cycloalkyl, $C_{2-9}$ heterocyclyl, $C_{1-9}$ heteroaryl, $C_{1-4}$ haloalkyl, H—$(CH_2)_n$—O—$(CH_2)_n$—, $N(R^4)_2$—C(═O)—, H—$(CH_2)_n$—SO$_2$—$(CH_2)_n$—, H—O—$(CH_2)_n$—C(═O)—$(CH_2)_n$—, H—$(CH_2)_n$—C(═O)—$(CH_2)_n$— or $N(R^4)_2$—$(CH_2)_n$—;

each $R^4$ is independently H, $C_{1-4}$ alkyl, hydroxy, carboxy, amino, $C_{1-4}$ alkoxy, amino-$C_{1-4}$-alkyl, $NH_2$—C(═O)—, $C_{3-9}$ cycloalkyl, $C_{2-9}$ heterocyclyl, $C_{1-9}$ heteroaryl, $C_{1-4}$ haloalkyl or $C_{1-4}$ alkylamino;

each moiety represented by A is independently and optionally substituted with one, two, three or four substituents independently selected from H, $C_{1-4}$ alkyl, F, Cl, Br, amino, hydroxy, carboxy, $C_{1-4}$ alkoxy, $C_{1-4}$ haloalkyl, $C_{1-4}$ alkylamino, amino-$C_{1-4}$-alkyl, H—$(C(R^3)_2)_n$—O—C(═O)—$(C(R^3)_2)_n$—, $(R^4R^4)$N—$(C(R^3)_2)_n$—, HO—$(C(R^3)_2)_n$—C(═O)—, $NR^4R^4$—C(═O)—, HO—$(C(R^3)_2)_n$—, H—$(C(R^3)_2)_n$—O—$(C(R^3)_2)_n$—, H—$(C(R^3)_2)_n$—SO$_2$—$(C(R^3)_2)_n$—, H—$(C(R^3)_2)_n$—C(═O)—$(C(R^3)_2)_n$—, CN—$(C(R^3)_2)_n$—C(═O)—, H—$(C(R^3)_2)_n$—O—C(═O)—C(═O)—$(C(R^3)_2)_n$—, cyano and nitro.

each alkyl, haloalkyl, H—$(C(R^3)_2)_n$—O—C(═O)—$(C(R^3)_2)_n$—, $N(R^4)_2$—C(═O)—, H—$(C(R^3)_2)_n$—SO$_2$—$(C(R^3)_2)_n$—, —$(C(R^3)_2)_n$—$N(R^4)_2$, HO—$(C(R^3)_2)_n$—C(═O)—, HO—$(C(R^3)_2)_n$—, H—$(C(R^3)_2)_n$—O—$(C(R^3)_2)_n$—, H—$(C(R^3)_2)_n$—C(═O)—$(C(R^3)_2)_n$—, CN—$(C(R^3)_2)_n$—C(═O)—, spiro heterobicyclyl, bridged heterobicyclyl, fused heterobicyclyl, heterocyclyl, cycloalkyl, heteroaryl and H—$(C(R^3)_2)_n$—O—C(═O)—C(═O)—$(C(R^3)_2)_n$—, aryl, 4-membered heterocyclyl, 5-membered heterocyclyl, 6-membered heterocyclyl and 7-membered heterocyclyl described in R, $R^{1a}$, $R^1$ and/or $R^2$ is optionally and independently substituted with one, two, three or four independent $R^5$;

each $R^5$ is independently H, oxo(═O), $C_{1-6}$ alkyl, F, Cl, Br, amino, hydroxy, carboxy, $C_{1-4}$ alkoxy, $C_{1-4}$ alkylamino, amino-$C_{1-4}$-alkyl, $N(R^4)_2$—C(═O)—, CN—$(C(R^3)_2)_n$—C(═O)—, $C_{1-6}$ haloalkyl, H—$(C(R^3)_2)_n$—O—C(═O)—(C (R³)₂)ₙ—, H—(C(R³)₂)ₙ—SO₂—(C(R³)₂)ₙ—, —(C(R³)₂)ₙ—N(R⁴)₂, HO—(C(R³)₂)ₙ—C(=O)—, HO—(C(R³)₂)ₙ—, H—(C(R³)₂)ₙ—O—(C(R³)₂)ₙ—, N(R⁴)₂—C(=O)—(C(R³)₂)ₙ—, H—(C(R³)₂)ₙ—O—(C(R³)₂)ₙ₁—C(=O)—(C(R³)₂)ₙ—, H—(C(R³)₂)ₙ—C(=O)—(C(R³)₂)ₙ—, spiro heterobicyclyl, bridged heterobicyclyl, fused heterobicyclyl, H—(C(R³)₂)ₙ—O—C(=O)—C(=O)—(C(R³)₂)ₙ—, cyano, $C_{2-9}$ heterocyclyl, $C_{3-9}$ cycloalkyl, $C_{1-9}$ heteroaryl or nitro;

each alkyl, haloalkyl, alkoxy, alkylamino, aminoalkyl, spiro heterobicyclyl, bridged heterobicyclyl, fused heterobicyclyl, N(R⁴)₂—C(=O)—, CN—(C(R³)₂)ₙ—C(=O)—, H—(C(R³)₂)ₙ—O—C(=O)—(C(R³)₂)ₙ—, H—(C(R³)₂)ₙ—SO₂—(C(R³)₂)ₙ—, —(C(R³)₂)ₙ—N(R⁴)₂, HO—(C(R³)₂)ₙ—C(=O)—, HO—(C(R³)₂)ₙ—, H—(C(R³)₂)ₙ—O—(C(R³)₂)ₙ—, N(R⁴)₂—C(=O)—(C(R³)₂)ₙ—, H—(C(R³)₂)ₙ—O—(C(R³)₂)ₙ₁—C(=O)—(C(R³)₂)ₙ—, H—(C(R³)₂)ₙ—C(=O)—(C(R³)₂)ₙ—, H—(C(R³)₂)ₙ—O—C(=O)—C(=O)—(C(R³)₂)ₙ—, heterocyclyl, cycloalkyl and heteroaryl described in R⁵ is optionally and independently substituted with one, two, three or four independent R⁶; and each R⁶ is independently H, oxo(=O), $C_{1-4}$ alkyl, F, Cl, Br, amino, hydroxy, carboxy, $C_{1-4}$ alkoxy, $C_{1-4}$ alkylamino, amino-$C_{1-4}$-alkyl, N(R⁴)₂—C(=O)—, CN—(C(R³)₂)ₙ—C(=O)—, $C_{1-4}$ haloalkyl, H—(C(R³)₂)ₙ—O—C(=O)—(C(R³)₂)ₙ—, H—(C(R³)₂)ₙ—SO₂—(C(R³)₂)ₙ—, —(C(R³)₂)ₙ—N(R⁴)₂, HO—(C(R³)₂)ₙ—C(=O)—, HO—(C(R³)₂)ₙ—, H—(C(R³)₂)ₙ—O—(C(R³)₂)ₙ—, N(R⁴)₂—C(=O)—(C(R³)₂)ₙ—, H—(C(R³)₂)ₙ—O—(C(R³)₂)ₙ—C(=O)—(C(R³)₂)ₙ—, H—(C(R³)₂)ₙ—C(=O)—(C(R³)₂)ₙ—, spiro heterobicyclyl, bridged heterobicyclyl, fused heterobicyclyl, H—(C(R³)₂)ₙ—O—C(=O)—C(=O)—(C(R³)₂)ₙ—, cyano, $C_{2-9}$ heterocyclyl, $C_{3-9}$ cycloalkyl, $C_{1-9}$ heteroaryl or nitro.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

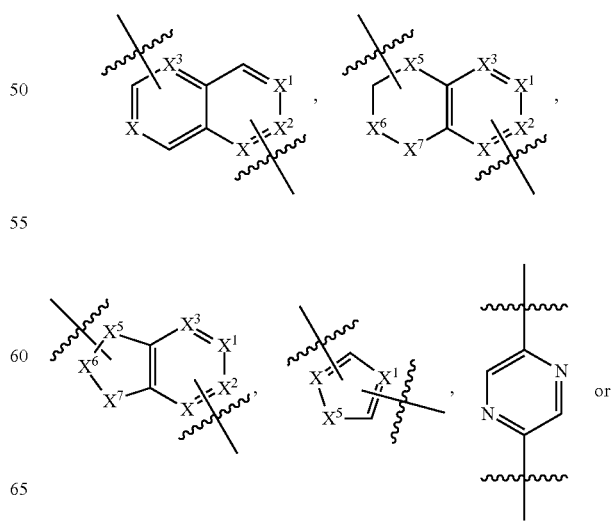

(I)

wherein ring A, L and R are as defined herein.

In some embodiments, L is a bond, —(C(R^{3b})₂)ₙ—, —N(R¹)—(C(R^{3b})₂)ₙ—, —O—(C(R^{3b})₂)ₙ—, —S(=O)ₘ— or —C(=O)—(C(R^{3b})₂)ₙ—; and wherein n, m, R¹ and R^{3b} are as defined herein.

In some embodiments, ring A is

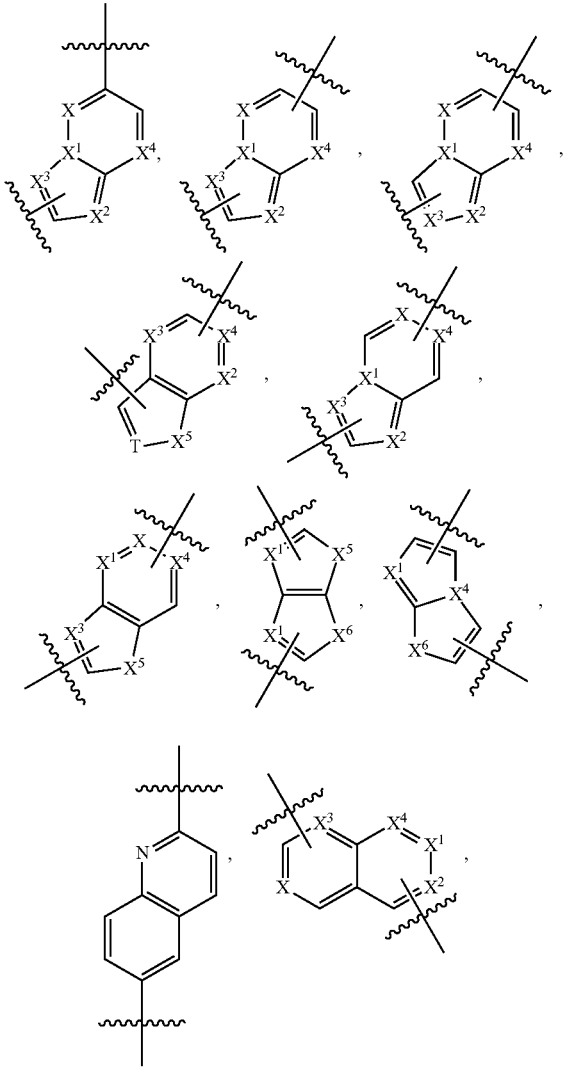

-continued

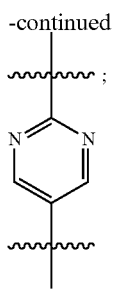

wherein when ═ is a double bond, T is X,

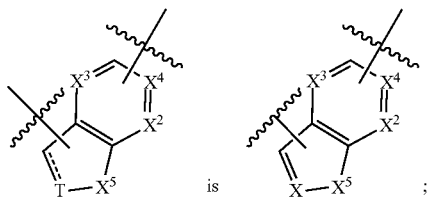

when ═ is a double bond, T is $X^6$,

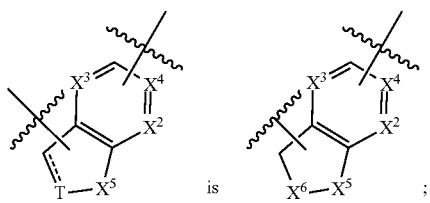

wherein each $X^7$, $X^5$ and $X^6$ is independently —$C(R^{3a})_2$—, —$N(R^2)$—, —O—, —$S(=O)_m$—, or —C(=O)—;

each X, $X^1$, $X^2$, $X^3$ and $X^4$ is independently $CR^{3a}$ or N; and wherein m, $R^2$ and $R^{3a}$ are as defined herein.

In some embodiments, R is H, $R^{13}$, —$(C(R^{3b})_2)_n$—N($R^{1a}$)—C(=O)—$(C(R^{3b})_2)_n$—$R^{13}$ or —$(CH_2)_n$—C(=O)—N($R^{1a}$)—$(C(R^{3b})_2)_n$—$R^{13}$;

$R^{13}$ is H, $C_{3-9}$ cycloalkyl, $C_{1-9}$ heteroaryl, $C_{2-9}$ heterocyclyl or $R^0$;

each $R^0$, R and $R^{13}$ is optionally and independently substituted with one, two, three or four independent $R^5$; and wherein $R^5$, n, $R^0$, $R^1$ and $R^3$ are as defined herein.

In some embodiments, each n is independently 0, 1, 2, 3 or 4.

In some embodiments, each n1 is independently 1, 2 or 3.

In some embodiments, each m is independently 0, 1 or 2.

In some embodiments, $R^0$ is $C_{5-11}$ spiro heterobicyclyl, $C_{5-11}$ bridged heterobicyclyl or $C_{5-11}$ fused heterobicyclyl, which is substituted optionally with one, two, three or four independent $R^5$; and wherein $R^5$ is as defined herein.

In some embodiments, each $R^{01}$ is independently $C_{2-9}$ heterocyclyl, $C_{1-9}$ heteroaryl or $C_{3-9}$ cycloalkyl, which is substituted optionally with one, two, three or four independent $R^5$; and wherein $R^5$ is as defined herein.

In some embodiments, each $R^{00}$ is independently $C_{2-9}$ heterocyclyl, $C_{1-9}$ heteroaryl or $C_{3-9}$ cycloalkyl, which is substituted optionally with one, two, three or four independent $R^5$; and wherein $R^5$ is as defined herein.

In some embodiments, each $R^1$ is independently H, $C_{1-4}$ haloalkyl, H—$(C(R^3)_2)_n$—O—C(=O)—$(C(R^3)_2)_n$—, $(R^4)_2N$—$(C(R^3)_2)_n$—, HO—$(C(R^3)_2)_n$—C(=O)—, $N(R^4)_2$—C(=O)—, HO—$(C(R^3)_2)_n$—, H—$(C(R^3)_2)_n$—O—$(C(R^3)_2)_n$—, H—$(C(R^3)_2)_n$—$SO_2$—$(C(R^3)_2)_n$—, H—$(C(R^3)_2)_n$—C(=O)—$(C(R^3)_2)_n$—, CN—$(C(R^3)_2)_n$—C(=O)—, H—$(C(R^3)_2)_n$—O—C(=O)—C(=O)—$(C(R^3)_2)_n$—, $R^{00}$ or $C_{1-4}$ alkyl, which is substituted optionally with one, two, three or four independent $R^5$; and wherein $R^5$, n, $R^{00}$, $R^4$ and $R^3$ are as defined herein.

In some embodiments, each $R^{1a}$ is independently H, $C_{1-4}$ haloalkyl, H—$(C(R^3)_2)_n$—O—C(=O)—$(C(R^3)_2)_n$—, $(R^4)_2N$—$(C(R^3)_2)_n$—, HO—$(C(R^3)_2)_n$—C(=O)—, $N(R^4)_2$—C(=O)—, HO—$(C(R^3)_2)_n$—, H—$(C(R^3)_2)_n$—O—$(C(R^3)_2)_n$—, H—$(C(R^3)_2)_n$—$SO_2$—$(C(R^3)_2)_n$—, H—$(C(R^3)_2)_n$—C(=O)—$(C(R^3)_2)_n$—, CN—$(C(R^3)_2)_n$—C(=O)—, H—$(C(R^3)_2)_n$—O—C(=O)—C(=O)—$(C(R^3)_2)_n$—, $R^{00}$ or $C_{1-4}$ alkyl, which is substituted optionally with one, two, three or four independent $R^5$; and wherein $R^5$, n, $R^{00}$, $R^4$ and $R^3$ are as defined herein.

In some embodiments, each $R^2$ is independently H, $C_{1-4}$ haloalkyl, H—$(C(R^3)_2)_n$—O—C(=O)—$(C(R^3)_2)_n$—, $(R^4)_2N$—$(C(R^3)_2)_n$—, HO—$(C(R^3)_2)_n$—C(=O)—, $N(R^4)_2$—C(=O)—, HO—$(C(R^3)_2)_n$—, H—$(C(R^3)_2)_n$—O—$(C(R^3)_2)_n$—, H—$(C(R^3)_2)_n$—$SO_2$—$(C(R^3)_2)_n$—, H—$(C(R^3)_2)_n$—C(=O)—$(C(R^3)_2)_n$—, CN—$(C(R^3)_2)_n$—C(=O)—, H—$(C(R^3)_2)_n$—O—C(=O)—C(=O)—$(C(R^3)_2)_n$—, $R^{00}$ or $C_{1-4}$ alkyl, which is substituted optionally with one, two, three or four independent $R^5$; and wherein $R^5$, n, $R^{00}$, $R^4$ and $R^3$ are as defined herein.

In some embodiments, each $R^3$ is independently H, F, Cl, Br, $C_{1-4}$ alkyl, hydroxy, carboxy, amino, $R^{01}$, $C_{1-4}$ haloalkyl, H—$(CH_2)_n$—O—$(CH_2)_n$—, $N(R^4)_2$—C(=O)—, H—$(CH_2)_n$—$SO_2$—$(CH_2)_n$—, H—O—$(CH_2)_n$—C(=O)—$(CH_2)_n$—, H—$(CH_2)_n$—C(=O)—$(CH_2)_n$— or $N(R^4)_2$—$(CH_2)_n$—; and wherein n, $R^{01}$ and $R^4$ are as defined herein.

In some embodiments, each $R^{3a}$ is independently H, F, Cl, Br, $C_{1-4}$ alkyl, hydroxy, carboxy, amino, $R^{01}$, $C_{1-4}$ haloalkyl, H—$(CH_2)_n$—O—$(CH_2)_n$—, $N(R^4)_2$—C(=O)—, H—$(CH_2)_n$—$SO_2$—$(CH_2)_n$—, H—O—$(CH_2)_n$—C(=O)—$(CH_2)_n$—, H—$(CH_2)_n$—C(=O)—$(CH_2)_n$— or $N(R^4)_2$—$(CH_2)_n$—; and wherein n, $R^{01}$ and $R^4$ are as defined herein.

In some embodiments, each $R^{3b}$ is independently H, F, Cl, Br, $C_{1-4}$ alkyl, hydroxy, carboxy, amino, $R^{01}$, $C_{1-4}$ haloalkyl, H—$(CH_2)_n$—O—$(CH_2)_n$—, $N(R^4)_2$—C(=O)—, H—$(CH_2)_n$—$SO_2$—$(CH_2)_n$—, H—O—$(CH_2)_n$—C(=O)—$(CH_2)_n$—, H—$(CH_2)_n$—C(=O)—$(CH_2)_n$— or $N(R^4)_2$—$(CH_2)_n$—; and wherein n, $R^{01}$ and $R^4$ are as defined herein.

In some embodiments, each $R^4$ is independently H, $C_{1-4}$ alkyl, hydroxy, carboxy, amino, $C_{1-4}$ alkoxy, amino-$C_{1-4}$-alkyl, $NH_2$—C(=O)—, $R^{01}$, $C_{1-4}$ haloalkyl or $C_{1-4}$ alkylamino; and wherein $R^{01}$ is as defined herein.

In some embodiments, each moiety represented by A is independently and optionally substituted with one, two, three or four substituents independently selected from H, $C_{1-4}$ alkyl, F, Cl, Br, amino, hydroxy, carboxy, $C_{1-4}$ alkoxy, $C_{1-4}$ haloalkyl, $C_{1-4}$ alkylamino, amino-$C_{1-4}$-alkyl, H—$(C(R^3)_2)_n$—O—C(=O)—$(C(R^3)_2)_n$—, $(R^4)_2N$—$(C(R^3)_2)_n$—, HO—$(C(R^3)_2)_n$—C(=O)—, $N(R^4)_2$—C(=O)—, HO—(C $(R^3)_2)_n$—, H—$(C(R^3)_2)_n$—O—$(C(R^3)_2)_n$—, H—$(C(R^3)_2)_n$—SO$_2$—$(C(R^3)_2)_n$—, H—$(C(R^3)_2)_n$—C(=O)—$(C(R^3)_2)_n$—, CN—$(C(R^3)_2)_n$—C(=O)—, H—$(C(R^3)_2)_n$—O—C(=O)—C(=O)—$(C(R^3)_2)_n$—, cyano and nitro; and wherein n, $R^4$ and $R^3$ are as defined herein.

In some embodiments, each $R^5$ is independently H, oxo (=O), $C_{1-6}$ alkyl, F, Cl, Br, amino, hydroxy, carboxy, $C_{1-4}$ alkoxy, $C_{1-4}$ alkylamino, amino-$C_{1-4}$-alkyl, $N(R^4)_2$—C(=O)—, CN—$(C(R^3)_2)_n$—C(=O)—, $C_{1-6}$ haloalkyl, H—$(C(R^3)_2)_n$—O—C(=O)—C(=O)—$(C(R^3)_2)_n$—, H—$(C(R^3)_2)_n$—C(=O)—$(C(R^3)_2)_n$—, H—$(C(R^3)_2)_n$—SO$_2$—$(C(R^3)_2)_n$—, H—$(C(R^3)_2)_n$—O—$(C(R^3)_2)_{n1}$—C(=O)—$(C(R^3)_2)_n$—, H—$(C(R^3)_2)_n$—O—C(=O)—$(C(R^3)_2)_n$—, H—$(C(R^3)_2)_n$—O—$(C(R^3)_2)_n$—, cyano, $C_{2-9}$ heterocyclyl, $C_{3-9}$ cycloalkyl, $C_{1-9}$ heteroaryl or nitro;

each alkyl, alkoxy, alkylamino, aminoalkyl, $N(R^4)_2$—C(=O)—, CN—$(C(R^3)_2)_n$—C(=O)—, haloalkyl, H—$(C(R^3)_2)_n$—O—C(=O)—$(C(R^3)_2)_n$—, H—$(C(R^3)_2)_n$—O—C(=O)—C(=O)—$(C(R^3)_2)_n$—, H—$(C(R^3)_2)_n$—C(=O)—$(C(R^3)_2)_n$—, H—$(C(R^3)_2)_n$—SO$_2$—$(C(R^3)_2)_n$—, H—$(C(R^3)_2)_n$—O—$(C(R^3)_2)_{n1}$—C(=O)—$(C(R^3)_2)_n$—, H—$(C(R^3)_2)_n$—O—$(C(R^3)_2)_n$—, heterocyclyl, cycloalkyl and heteroaryl described in $R^5$ is independently and optionally substituted with one, two, three or four independent $R^6$; and wherein $R^6$, n1, n, $R^4$ and $R^3$ are as defined herein.

In some embodiments, each $R^6$ is independently H, oxo(=O), $C_{1-4}$alkyl, F, Cl, Br, amino, hydroxy, carboxy, $C_{1-4}$ alkoxy, $C_{1-4}$ alkylamino, amino-$C_{1-4}$-alkyl, $N(R^4)_2$—C(=O)—, CN—$(C(R^3)_2)_n$—C(=O)—, $C_{1-4}$ haloalkyl, H—$(C(R^3)_2)_n$—O—C(=O)—$(C(R^3)_2)_n$—, H—$(C(R^3)_2)_n$—O—C(=O)—C(=O)—$(C(R^3)_2)_n$—, H—$(C(R^3)_2)_n$—C(=O)—$(C(R^3)_2)_n$—, H—$(C(R^3)_2)_n$—SO$_2$—$(C(R^3)_2)_n$—, H—$(C(R^3)_2)_n$—O—$(C(R^3)_2)_{n1}$—C(=O)—$(C(R^3)_2)_n$—, H—$(C(R^3)_2)_n$—O—$(C(R^3)_2)_n$—, cyano, $C_{2-9}$ heterocyclyl, $C_{3-9}$ cycloalkyl, $C_{1-9}$ heteroaryl or nitro; and wherein n1, n, $R^4$ and $R^3$ are as defined herein.

In some embodiments, provided herein is a compound having Formula (II) or a stereoisomer, a geometric isomer, a tautomer, an N-oxide, a hydrate, a solvate, a metabolite, an ester, a pharmaceutically acceptable salt or a prodrug thereof,

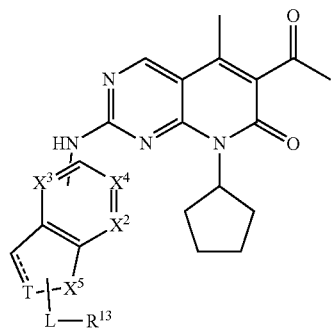

(II)

wherein

L is a bond, —(CH$_2$)$_n$—, —N(R$^1$)—, —O—, —S— or —C(=O)—;

when ═ is a double bond, T is X;

when ═ is a single bond, T is $X^6$; and wherein n, $R^1$, X, $X^2$, $X^3$, $X^4$, $X^5$, $X^6$ and $R^{13}$ are as defined herein.

In some embodiments, provided herein is a compound having Formula (III), or a stereoisomer, a geometric isomer, a tautomer, an N-oxide, a hydrate, a solvate, a metabolite, an ester, a pharmaceutically acceptable salt or a prodrug thereof,

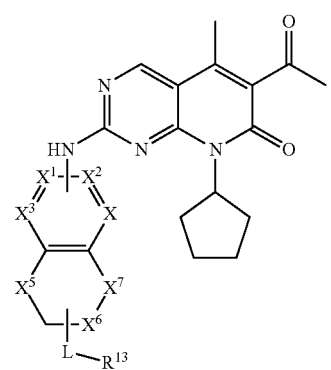

(III)

wherein L, X, $X^1$, $X^2$, $X^3$, $X^5$, $X^6$, $X^7$ and $R^{13}$ are as defined herein.

In some embodiments, $R^O$ is

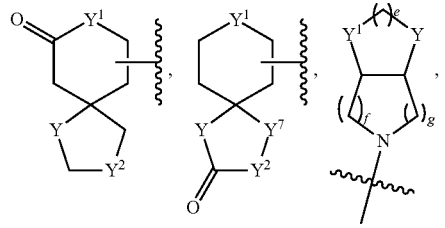

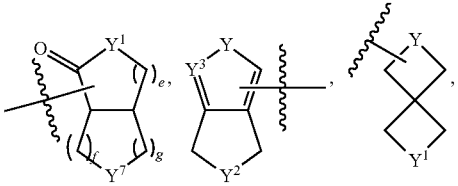

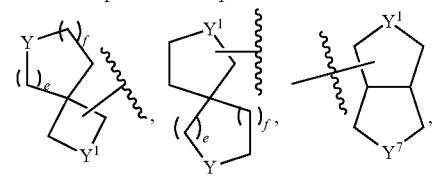

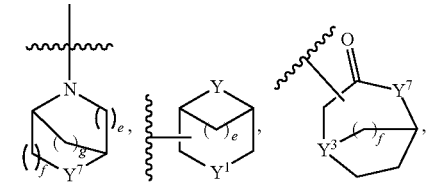

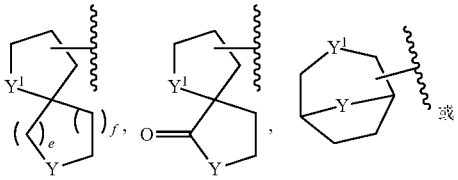

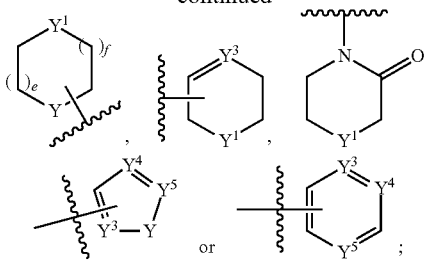

wherein each Y, Y¹, Y⁷ and Y² is independently —C(R³ᶜ)₂—, —N(R²ᵇ)—, —O—, —S(=O)ₘ— or —C(=O)—;
Y⁹ is CR³ᶜ or N;
Each e, r, g and f is independently 0, 1, 2, or 3;
R⁰ is optionally and independently substituted with one, two, three or four independent R⁵; and
wherein R⁵, R³ᶜ, R²ᵇ and m are as defined herein.

In some embodiments,
each R²ᵇ is independently H, C₁₋₄ haloalkyl, H—(C(R³)₂)ₙ—O—C(=O)—(C(R³)₂)ₙ—, (R⁴)₂N—(C(R³)₂)ₙ—, HO—(C(R³)₂)ₙ—C(=O)—, N(R⁴)₂—C(=O)—, HO—(C(R³)₂)ₙ—O—(C(R³)₂)ₙ—, H—(C(R³)₂)ₙ—O—(C(R³)₂)ₙ—, H—(C(R³)₂)ₙ—SO₂—(C(R³)₂)ₙ—, H—(C(R³)₂)ₙ—C(=O)—(C(R³)₂)ₙ—, CN—(C(R³)₂)ₙ—C(=O)—, H—(C(R³)₂)ₙ—O—C(=O)—C(=O)—(C(R³)₂)ₙ— or C₁₋₄ alkyl, which is substituted optionally with one, two, three or four independent R⁵; and
wherein R⁵, n, R⁴ and R³ are as defined herein.

In some embodiments,
each R³ᶜ is independently H, F, Cl, Br, C₁₋₄ alkyl, hydroxy, carboxy, amino, C₁₋₄ haloalkyl, H—(CH₂)ₙ—(CH₂)ₙ—, N(R⁴)₂—C(=O)—, H—(CH₂)ₙ—SO₂—(CH₂)ₙ—, H—O—(CH₂)ₙ—C(=O)—(CH₂)ₙ—, H—(CH₂)ₙ—C(=O)—(CH₂)ₙ— or N(R⁴)₂—(CH₂)ₙ—; and
wherein n and R⁴ are as defined herein.

In some embodiments,
each R⁰¹ is independently

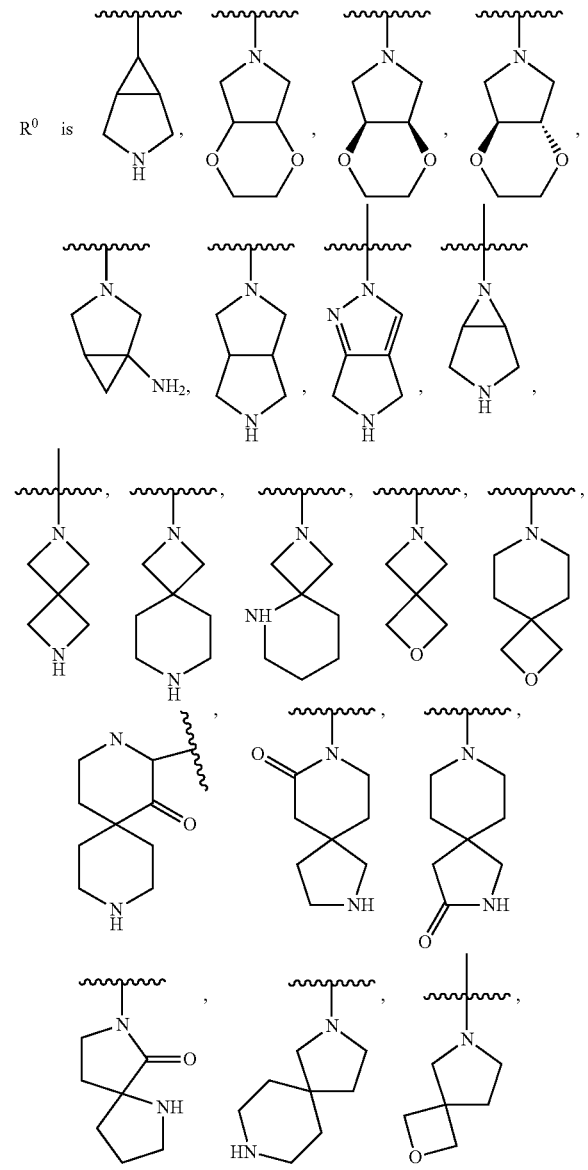

wherein each Y and Y¹ is independently —C(R³ᶜ)₂—, —N(R²ᵇ)—, —O—, —S(=O)ₘ— or —C(=O)—;
each Y³, Y⁴ and Y⁵ is independently CR³ᶜ or N; and
each e, r, f and g is independently 0, 1, 2, or 3;
each R⁰¹ is optionally and independently substituted with one, two, three or four independent R⁵; and
wherein R⁵, R³ᶜ, R²ᵇ and m are as defined herein.

In some embodiments,
each R⁰⁰ is independently wherein each Y and Y¹ is independently —C(R³ᶜ)₂—, —N(R²ᵇ)—, —O—, —S(=O)ₘ— or —C(=O)—;
each Y³, Y⁴ and Y⁵ is independently CR³ᶜ or N; and
each e, r, f and g is independently 0, 1, 2, or 3;
each R⁰⁰ is optionally and independently substituted with one, two, three or four independent R⁵; and
wherein R⁵, R³ᶜ, R²ᵇ and m are as defined herein.

In some embodiments,

-continued
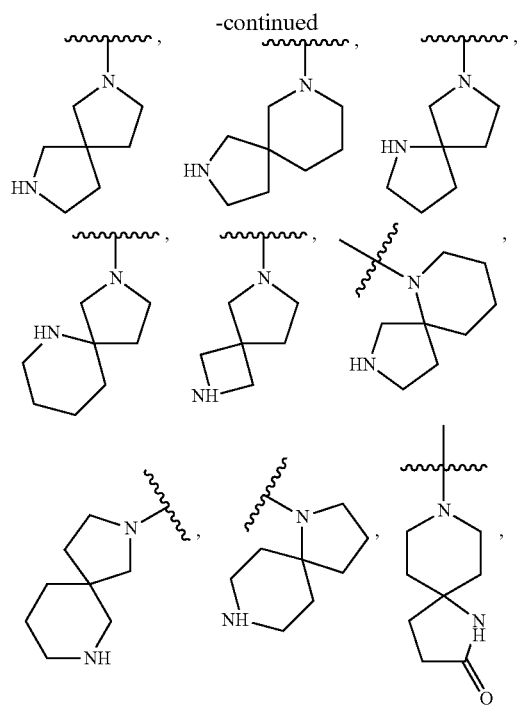
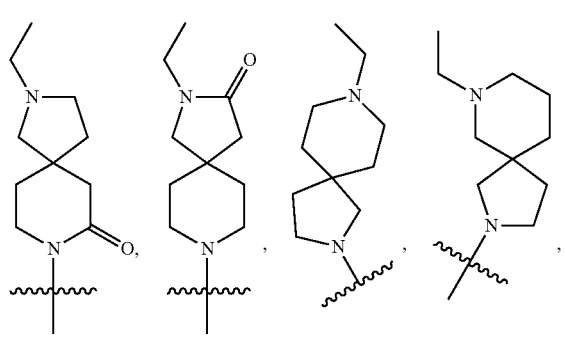
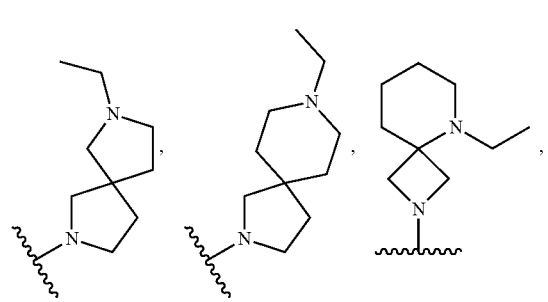
-continued
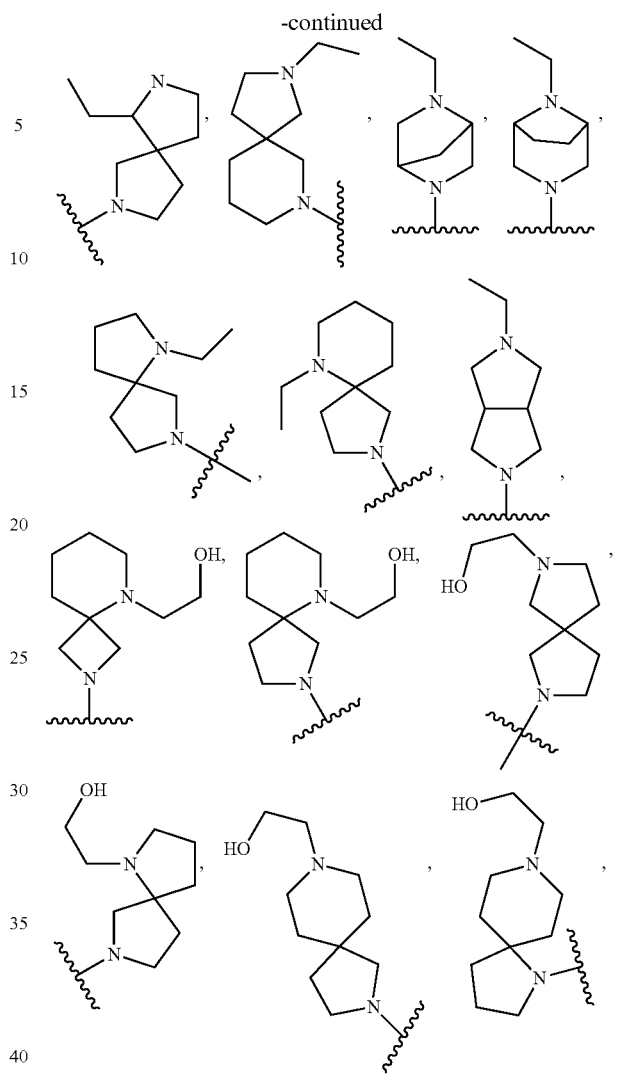
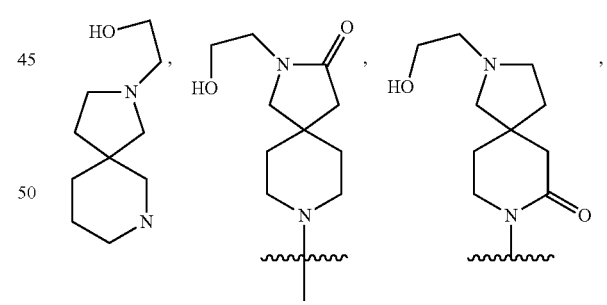
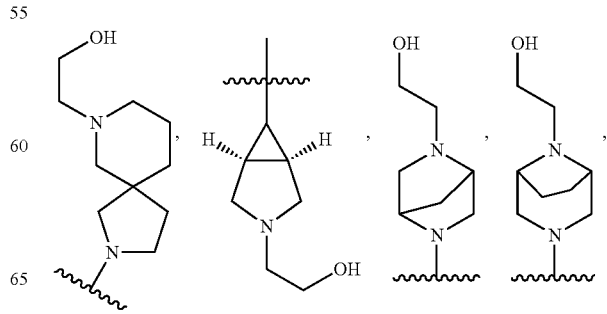

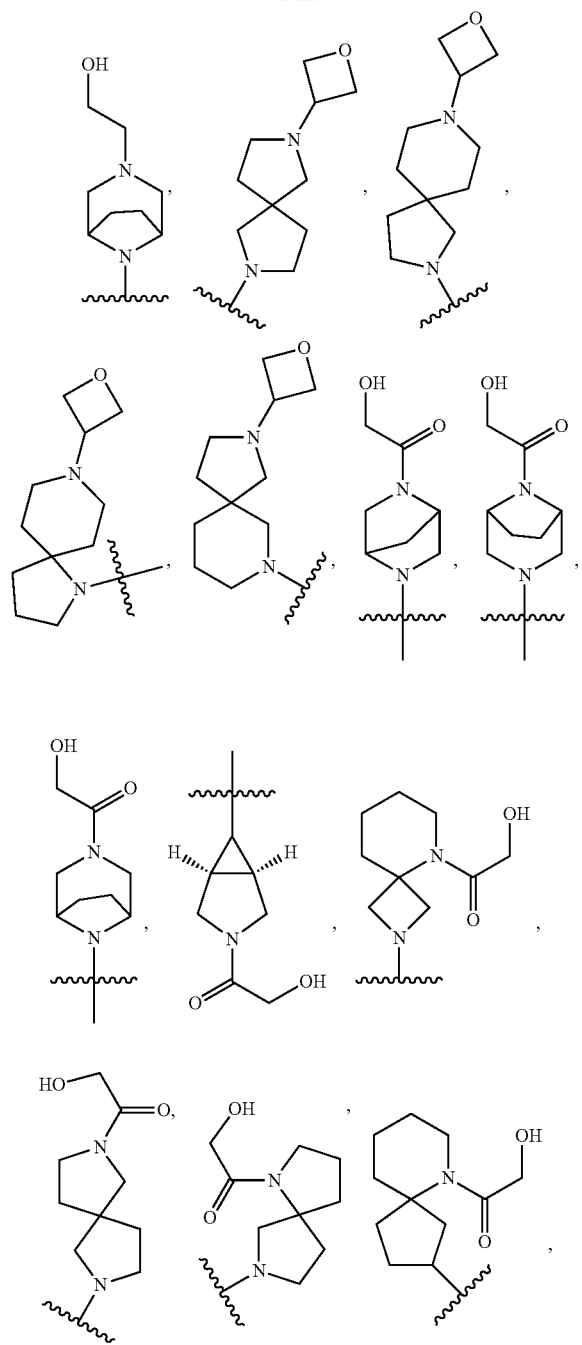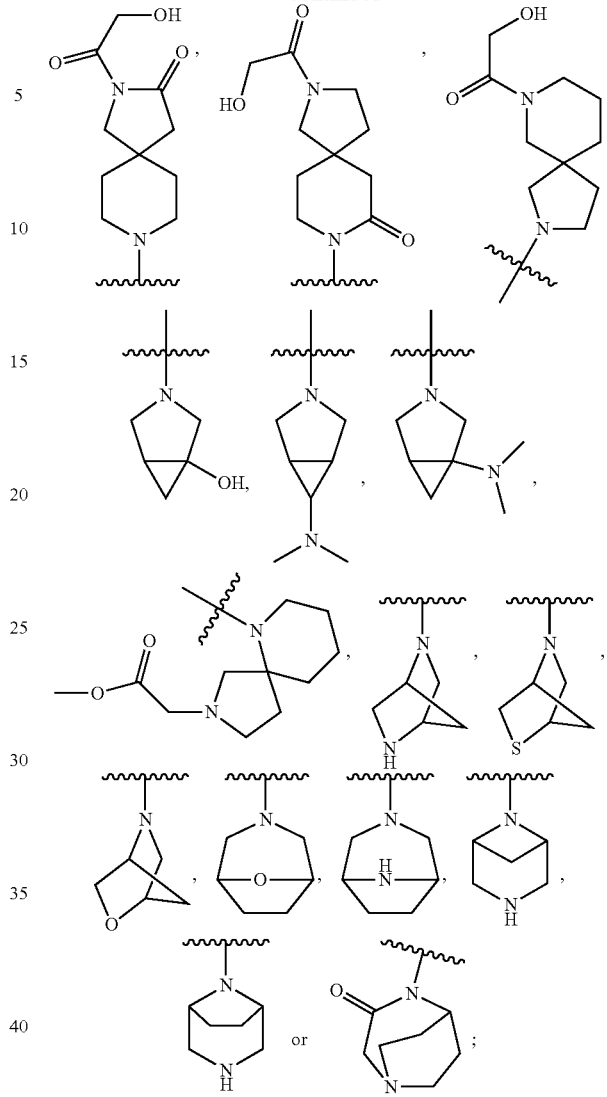
each moiety represented by $R^0$ is independently and optionally substituted with one, two, three or four independent $R^5$; and
wherein $R^5$ is as defined herein.
In some embodiments,
each $R^{00}$ is independently cyclopropyl, cyclohexyl, cyclopentyl, cyclobutyl,
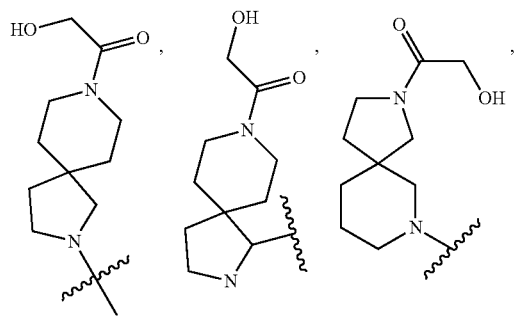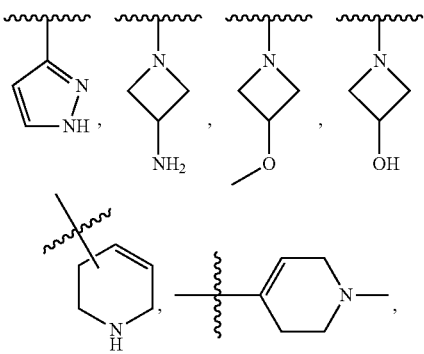

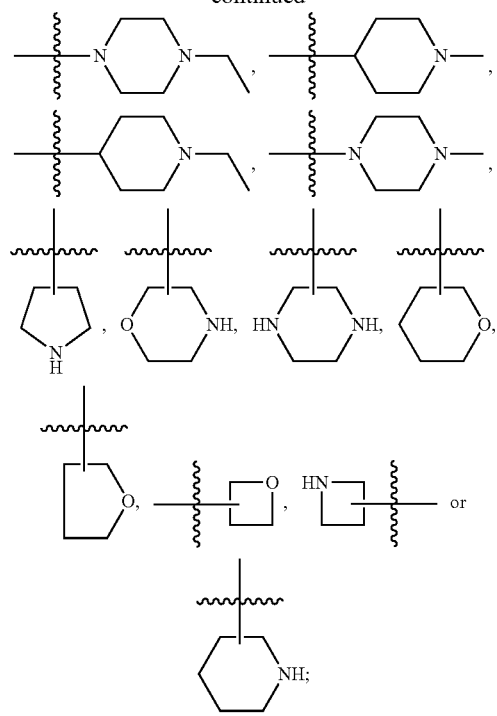

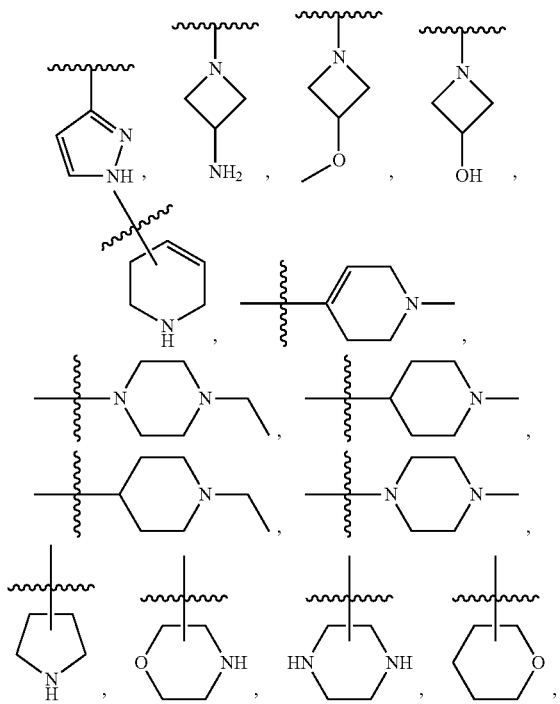

each moiety represented by $R^{00}$ is independently and optionally substituted with one, two, three or four independent $R^5$; and wherein $R^5$ is as defined herein.

In some embodiments, each $R^{01}$ is independently cyclopropyl, cyclohexyl, cyclopentyl, cyclobutyl,

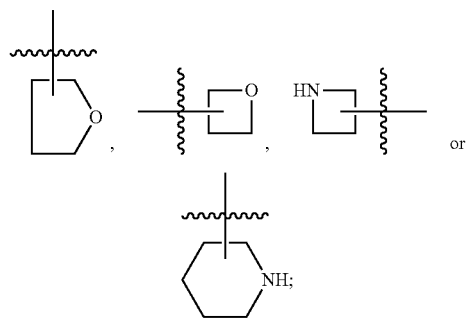

each moiety represented by $R^{01}$ is independently and optionally substituted with one, two, three or four independent $R^5$; and wherein $R^5$ is as defined herein.

In some embodiments, ring A is

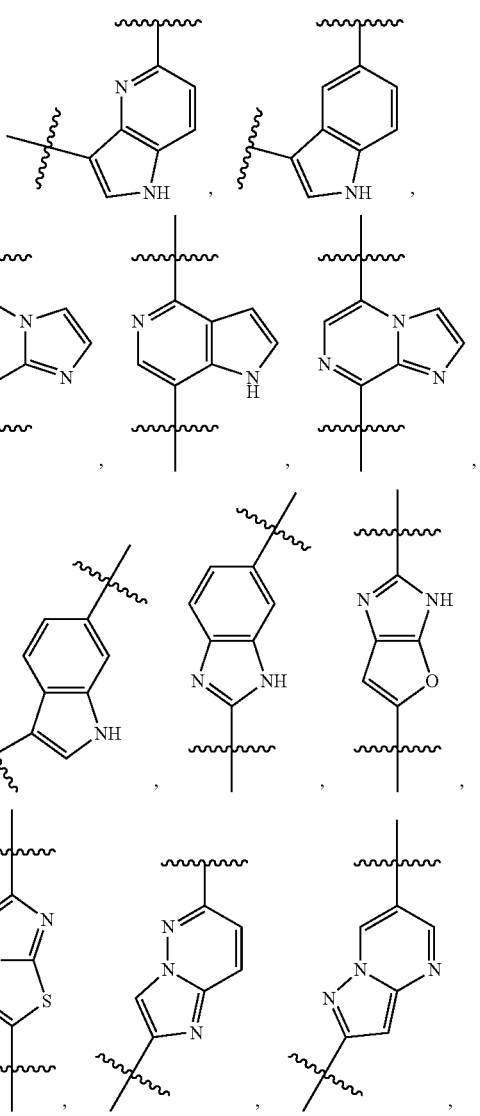

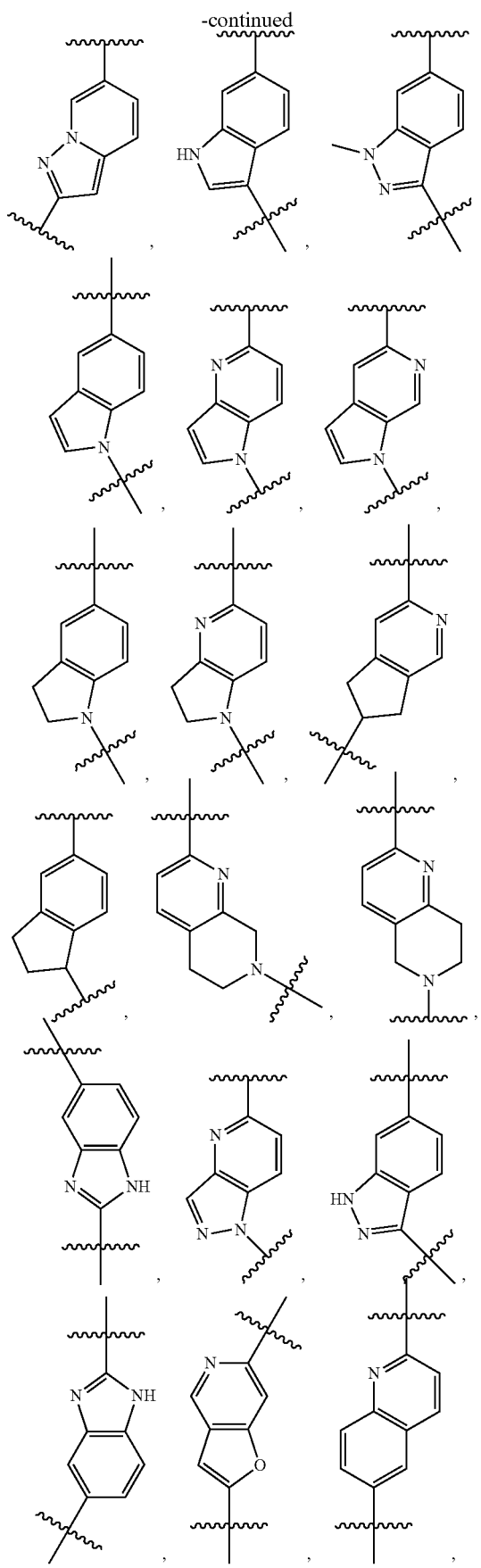
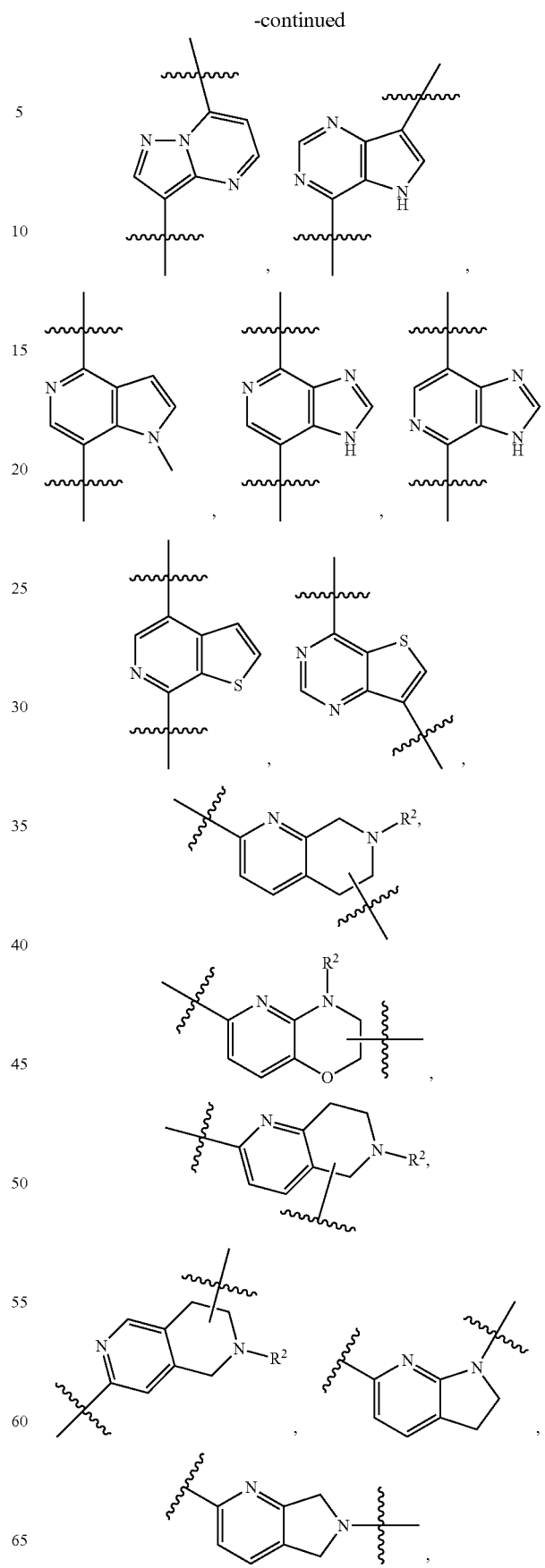

-continued

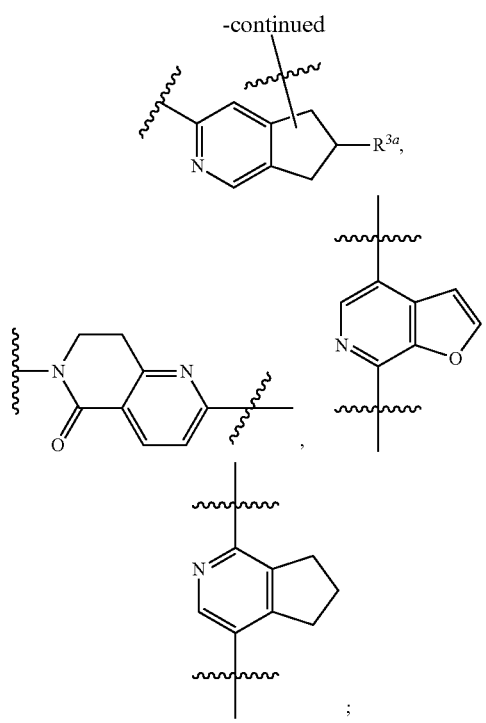

each moiety represented by A is independently and optionally substituted with one, two, three or four substituents independently selected from H, $C_{1-4}$ alkyl, F, Cl, Br, amino, hydroxy, carboxy, $C_{1-4}$ alkoxy, $C_{1-4}$ haloalkyl, $C_{1-4}$ alkylamino, amino-$C_{1-4}$-alkyl, H—$(C(R^3)_2)_n$—O—C(=O)—$(C(R^3)_2)_n$—, $(R^4)_2$N—$(C(R^3)_2)_n$—, HO—$(C(R^3)_2)_n$—C(=O)—, $N(R^4)_2$—C(=O)—, HO—$(C(R^3)_2)_n$—, H—$(C(R^3)_2)_n$—O—$(C(R^3)_2)_n$—, H—$(C(R^3)_2)_n$—SO$_2$—$(C(R^3)_2)_n$—, H—$(C(R^3)_2)_n$—C(=O)—$(C(R^3)_2)_n$—, CN—$(C(R^3)_2)_n$—C(=O)—, H—$(C(R^3)_2)_n$—O—C(=O)—C(=O)—$(C(R^3)_2)_n$—, cyano and nitro; and wherein $R^3$, $R^{3a}$, $R^4$, $R^2$ and n are as defined herein.

In some embodiments, $R^{13}$ is H, $R^0$,

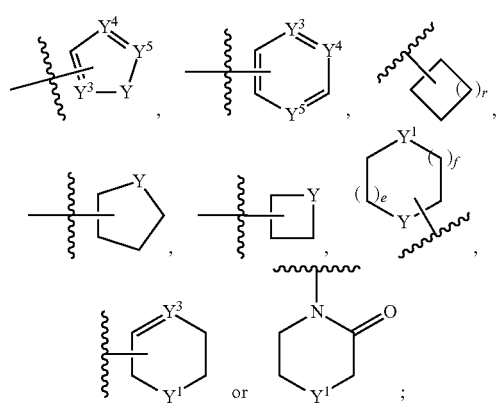

wherein each Y, $Y^7$, $Y^1$ and $Y^2$ is independently —$C(R^{3c})_2$—, —$N(R^{2b})$—, —O—, —S(=O)$_m$— or —C(=O)—;

each $Y^3$, $Y^4$ and $Y^5$ is independently $CR^{3c}$ or N; and each e, r and f is independently 0, 1, 2, or 3; and wherein $R^{3c}$, $R^0$, $R^{2b}$ and m are as defined herein.

In some embodiments, $R^{13}$ is H, $R^0$,

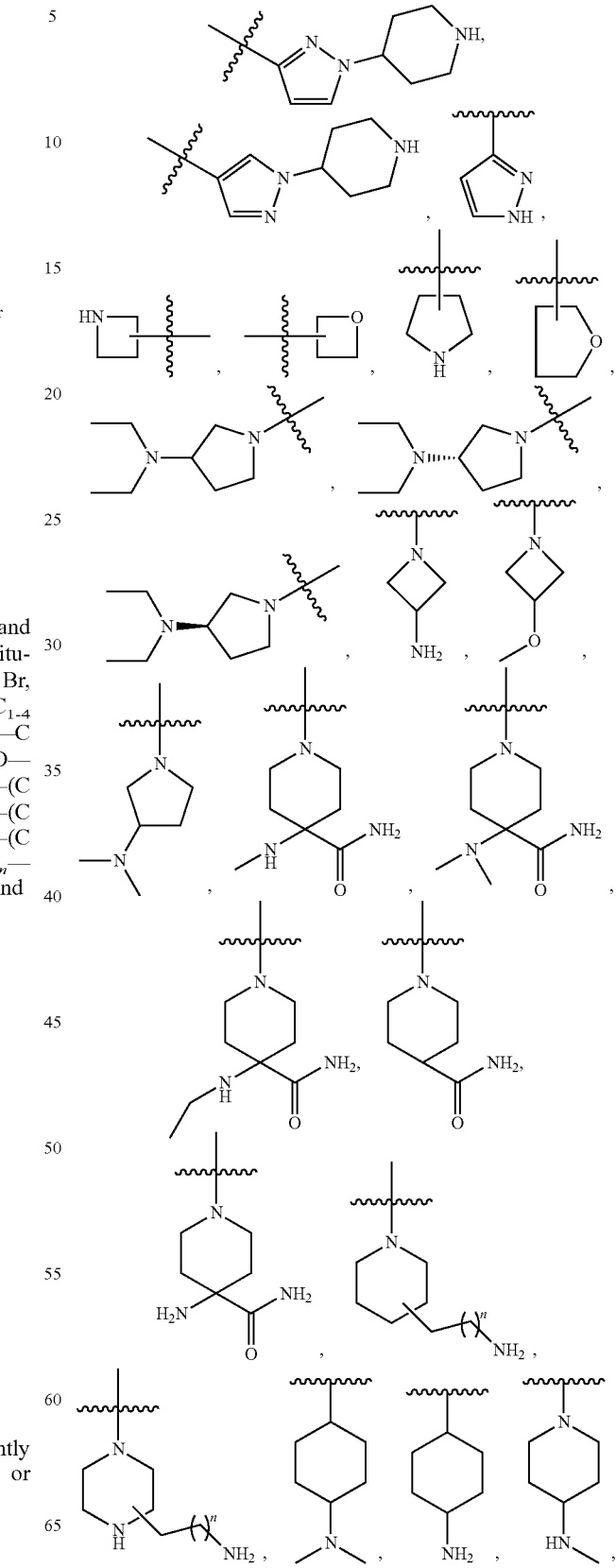

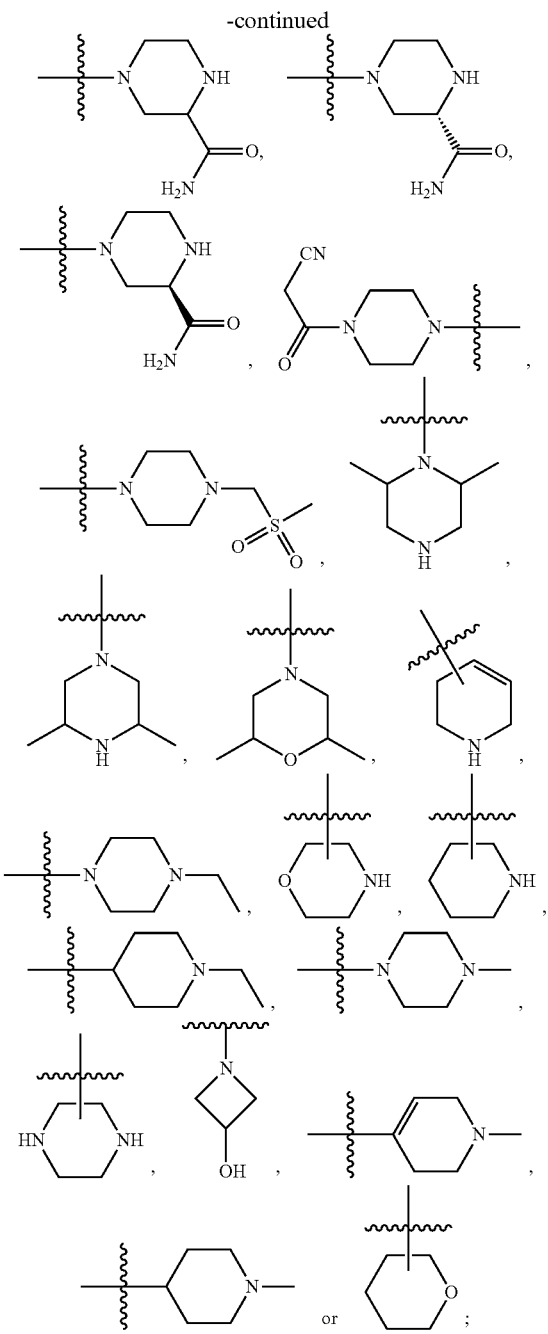

each moiety represented by R$^{13}$ is independently and optionally substituted with one, two, three or four independent R$^5$; and wherein R$^5$, R$^0$ and n are as defined herein.

In some embodiments, each R$^3$ is independently H, F, Cl, Br, hydroxy, carboxy, amino, trifluoromethyl, methyl, ethyl, propyl, butyl, cyclopropyl, cyclohexyl, cyclopentyl, H—(CH$_2$)$_n$—O—(CH$_2$)$_n$—, N(R$^4$)$_2$—C(=O)—, H—(CH$_2$)$_n$—SO$_2$—(CH$_2$)$_n$—, H—O—(CH$_2$)$_n$—C(=O)—(CH$_2$)$_n$— or N(R$^4$)$_2$—(CH$_2$)$_n$—; and wherein n and R$^4$ are as defined herein.

In some embodiments, each R$^{3a}$ is independently H, F, Cl, Br, hydroxy, carboxy, amino, trifluoromethyl, methyl, ethyl, propyl, butyl, cyclopropyl, cyclohexyl, cyclopentyl, H—(CH$_2$)$_n$—O—(CH$_2$)$_n$—, N(R$^4$)$_2$—C(=O)—, H—(CH$_2$)$_n$—SO$_2$—(CH$_2$)$_n$—, H—O—(CH$_2$)$_n$—C(=O)—(CH$_2$)$_n$— or N(R$^4$)$_2$—(CH$_2$)$_n$—; and wherein n and R$^4$ are as defined herein.

In some embodiments, each R$^{3b}$ is independently H, F, Cl, Br, hydroxy, carboxy, amino, trifluoromethyl, methyl, ethyl, propyl, butyl, cyclopropyl, cyclohexyl, cyclopentyl, H—(CH$_2$)$_n$—O—(CH$_2$)$_n$—, N(R$^4$)$_2$—C(=O)—, H—(CH$_2$)$_n$—SO$_2$—(CH$_2$)$_n$—, H—O—(CH$_2$)$_n$—C(=O)—(CH$_2$)$_n$— or N(R$^4$)$_2$—(CH$_2$)$_n$—; and wherein n and R$^4$ are as defined herein.

In some embodiments, each R$^{3c}$ is independently H, F, Cl, Br, hydroxy, carboxy, amino, trifluoromethyl, methyl, ethyl, propyl, butyl, H—(CH$_2$)$_n$—O—(CH$_2$)$_n$—, N(R$^4$)$_2$—C(=O)—, H—(CH$_2$)$_n$—SO$_2$—(CH$_2$)$_n$—, H—O—(CH$_2$)$_n$—C(=O)—(CH$_2$)$_n$— or N(R$^4$)$_2$—(CH$_2$)$_n$—; and wherein n and R$^4$ are as defined herein.

In some embodiments, each R$^4$ is independently H, hydroxy, carboxy, amino, methoxy, aminomethyl, aminoethyl, NH$_2$—C(=O)—, trifluoromethyl, 2,2-difluoroethyl, methyl, ethyl, propyl or butyl.

In some embodiments, each R$^1$ is independently H, 3,3,3-trifluoropropyl, trifluoromethyl, 1,1-difluoroethyl, H—(C(R$^3$)$_2$)$_n$—O—C(=O)—(C(R$^3$)$_2$)$_n$—, (R$^4$)$_2$N—(C(R$^3$)$_2$)$_n$—, HO—(C(R$^3$)$_2$)$_n$—C(=O)—, N(R$^4$)$_2$—C(=O)—, HO—(C(R$^3$)$_2$)$_n$—, H—(C(R$^3$)$_2$)$_n$—O—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—C(=O)—(C(R$^3$)$_2$)$_n$—, CN—(C(R$^3$)$_2$)$_n$—C(=O)—, H—(C(R$^3$)$_2$)$_n$—O—C(=O)—C(=O)—(C(R$^3$)$_2$)$_n$—, R$^{00}$, methyl, ethyl, propyl or butyl; and wherein R$^{00}$, R$^4$, R$^3$ and n are as defined herein.

In some embodiments, each R$^{1a}$ is independently H, 3,3,3-trifluoropropyl, trifluoromethyl, 1,1-difluoroethyl, H—(C(R$^3$)$_2$)$_n$—O—C(=O)—(C(R$^3$)$_2$)$_n$—, (R$^4$)$_2$N—(C(R$^3$)$_2$)$_n$—, HO—(C(R$^3$)$_2$)$_n$—C(=O)—, N(R$^4$)$_2$—C(=O)—, HO—(C(R$^3$)$_2$)$_n$—, H—(C(R$^3$)$_2$)$_n$—O—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—C(=O)—(C(R$^3$)$_2$)$_n$—, CN—(C(R$^3$)$_2$)$_n$—C(=O)—, H—(C(R$^3$)$_2$)$_n$—O—C(=O)—C(=O)—(C(R$^3$)$_2$)$_n$—, R$^{00}$, methyl, ethyl, propyl or butyl; and wherein R$^{00}$, R$^4$, R$^3$ and n are as defined herein.

In some embodiments, each R$^{1b}$ is independently H, 3,3,3-trifluoropropyl, trifluoromethyl, 1,1-difluoroethyl, H—(C(R$^3$)$_2$)$_n$—O—C(=O)—(C(R$^3$)$_2$)$_n$—, (R$^4$)$_2$N—(C(R$^3$)$_2$)$_n$—, HO—(C(R$^3$)$_2$)$_n$—C(=O)—, N(R$^4$)$_2$—C(=O)—, HO—(C(R$^3$)$_2$)$_n$—, H—(C(R$^3$)$_2$)$_n$—O—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—C(=O)—(C(R$^3$)$_2$)$_n$—, CN—(C(R$^3$)$_2$)$_n$—C(=O)—, H—(C(R$^3$)$_2$)$_n$—O—C(=O)—C(=O)—(C(R$^3$)$_2$)$_n$—, R$^{00}$, methyl, ethyl, propyl or butyl; and wherein R$^{00}$, R$^4$, R$^3$ and n are as defined herein.

In some embodiments, each R$^2$ is independently H, 3,3,3-trifluoropropyl, trifluoromethyl, 1,1-difluoroethyl, H—(C(R$^3$)$_2$)$_n$—O—C(=O)—(C(R$^3$)$_2$)$_n$—, (R$^4$)$_2$N—(C(R$^3$)$_2$)$_n$—, HO—(C(R$^3$)$_2$)$_n$—C(=O)—, N(R$^4$)$_2$—C(=O)—, HO—(C(R$^3$)$_2$)$_n$—, H—(C(R$^3$)$_2$)$_n$—O—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—C(=O)—(C(R$^3$)$_2$)$_n$—, CN—(C(R$^3$)$_2$)$_n$—C(=O)—, H—(C(R$^3$)$_2$)$_n$—O—C(=O)—C(=O)—(C(R$^3$)$_2$)$_n$—, R$^{00}$, methyl, ethyl, propyl or butyl; and wherein R$^{00}$, R$^4$, R$^3$ and n are as defined herein.

In some embodiments, each R$^{2b}$ is independently H, 3,3,3-trifluoropropyl, trifluoromethyl, 1,1-difluoroethyl, H—(C(R$^3$)$_2$)$_n$—O—C(=O)—(C(R$^3$)$_2$)$_n$—, (R$^4$)$_2$N—(C(R$^3$)$_2$)$_n$—, HO—(C(R$^3$)$_2$)$_n$—C(=O)—, N(R$^4$)$_2$—C(=O)—, HO—(C(R$^3$)$_2$)$_n$—, H—(C(R$^3$)$_2$)$_n$—O—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—C(=O)—(C(R$^3$)$_2$)$_n$—, CN—(C(R$^3$)$_2$)$_n$—C (=O)—, H—(C(R³)₂)ₙ—O—C(=O)—C(=O)—(C(R³)₂)ₙ—, methyl, ethyl, propyl or butyl; and wherein R⁴, R³ and n are as defined herein.

In some embodiments, each R⁵ is independently H, oxo (=O), methyl, ethyl, propyl, butyl, F, Cl, Br, amino, hydroxy, carboxy, methoxy, C₁₋₄ alkylamino, amino-C₁₋₄-alkyl, N(R⁴)₂—C(=O)—, CN—(C(R³)₂)ₙ—C(=O)—, trifluoromethyl, H—(C(R³)₂)ₙ—O—C(=O)—(C(R³)₂)ₙ—,

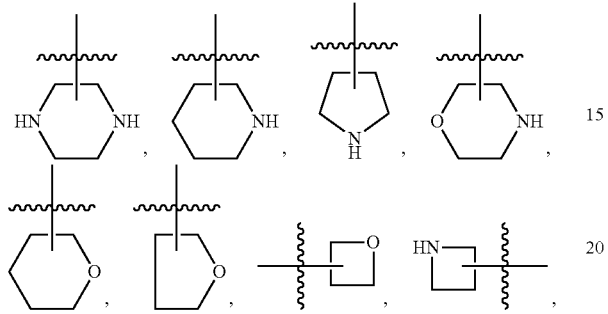

C₁₋₄ haloalkyl, H—(C(R³)₂)ₙ—O—C(=O)—C(=O)—(C(R³)₂)ₙ—, H—(C(R³)₂)ₙ—C(=O)—(C(R³)₂)ₙ—, H—(C(R³)₂)ₙ—O—(C(R³)₂)ₙ—, H—(C(R³)₂)ₙ—SO₂—(C(R³)₂)ₙ—, H—(C(R³)₂)ₙ—O—(C(R³)₂)ₙ₁—C(=O)—(C(R³)₂)ₙ—, cyano, cyclopropyl, cyclohexyl, cyclopentyl or nitro; and wherein n1, R⁴, R³ and n are as defined herein.

In some embodiments, each R⁶ is independently H, oxo (=O), methyl, ethyl, propyl, butyl, F, Cl, Br, amino, hydroxy, carboxy, methoxy, C₁₋₄alkylamino, amino-C₁₋₄-alkyl, N(R⁴)₂—C(=O)—, CN—(C(R³)₂)ₙ—C(=O)—, C₁₋₄ haloalkyl, H—(C(R³)₂)ₙ—O—C(=O)—(C(R³)₂)ₙ—, H—(C(R³)₂)ₙ—O—C(=O)—C(=O)—(C(R³)₂)ₙ—, H—(C(R³)₂)ₙ—C(=O)—(C(R³)₂)ₙ—, H—(C(R³)₂)ₙ—SO₂—(C(R³)₂)ₙ—, H—(C(R³)₂)ₙ—O—(C(R³)₂)ₙ₁—C(=O)—(C(R³)₂)ₙ—, H—(C(R³)₂)ₙ—O—(C(R³)₂)ₙ—, cyano, C₃₋₆ heterocyclyl, C₃₋₆ cycloalkyl or nitro; and wherein n1, R⁴, R³ and n are as defined herein.

In some embodiments,

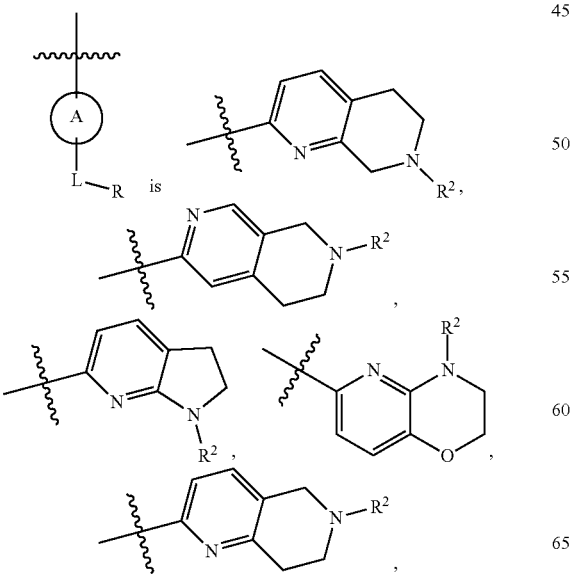

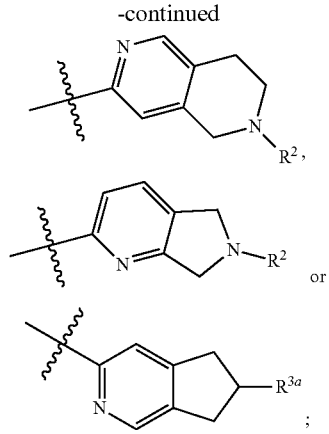

and wherein R² and R³ᵃ are as defined herein.

In some embodiments,

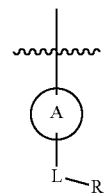

is one of the following sub-structures:

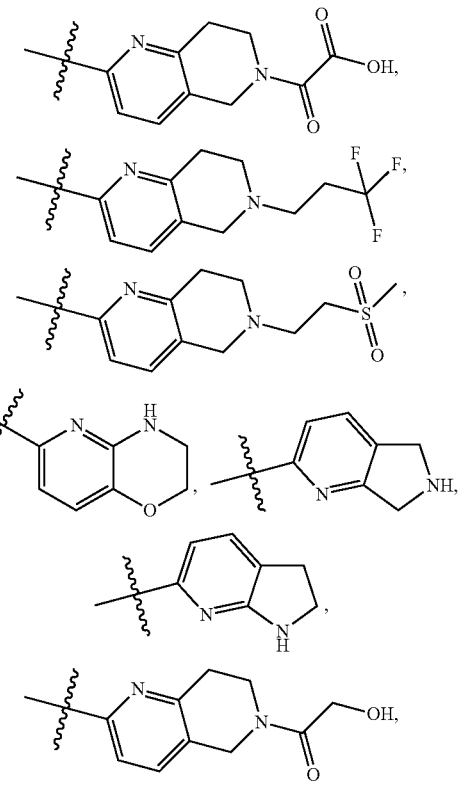

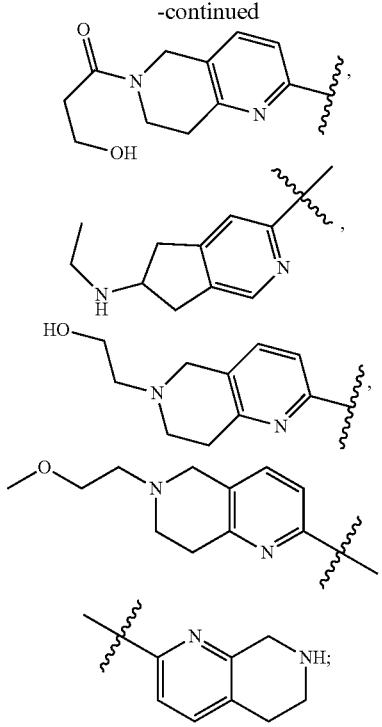

wherein each sub-structure above is independently and optionally substituted with one, two, three or four independent $R^5$; and wherein $R^5$ is as defined herein.

In one aspect, provided herein is a compound having one of the following structures, or a stereoisomer, a geometric isomer, a tautomer, an N-oxide, a hydrate, a solvate, a metabolite, an ester, a pharmaceutically acceptable salt or a prodrug thereof,

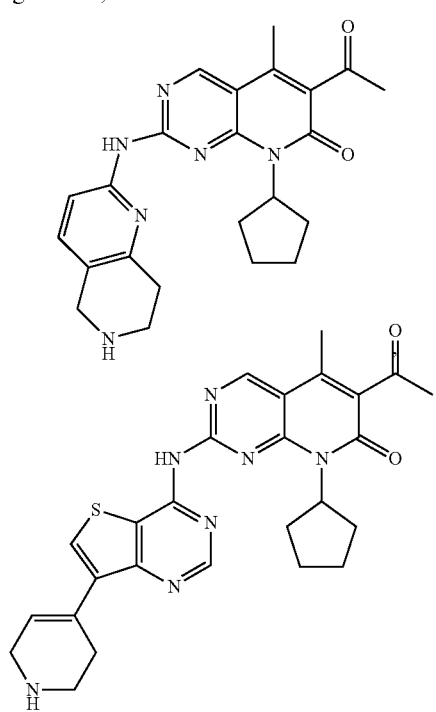

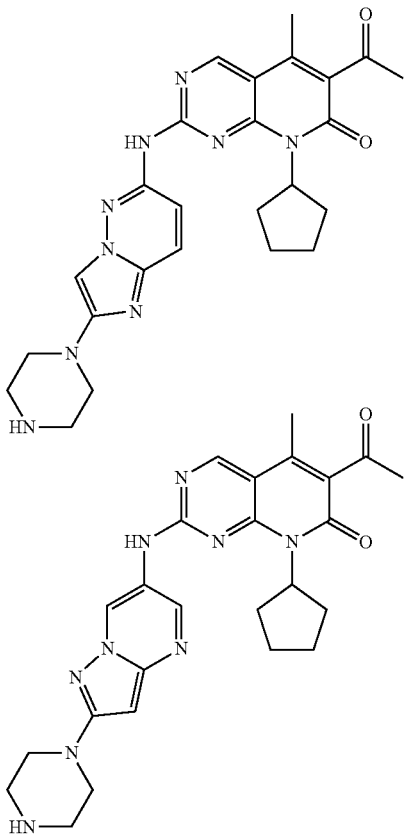

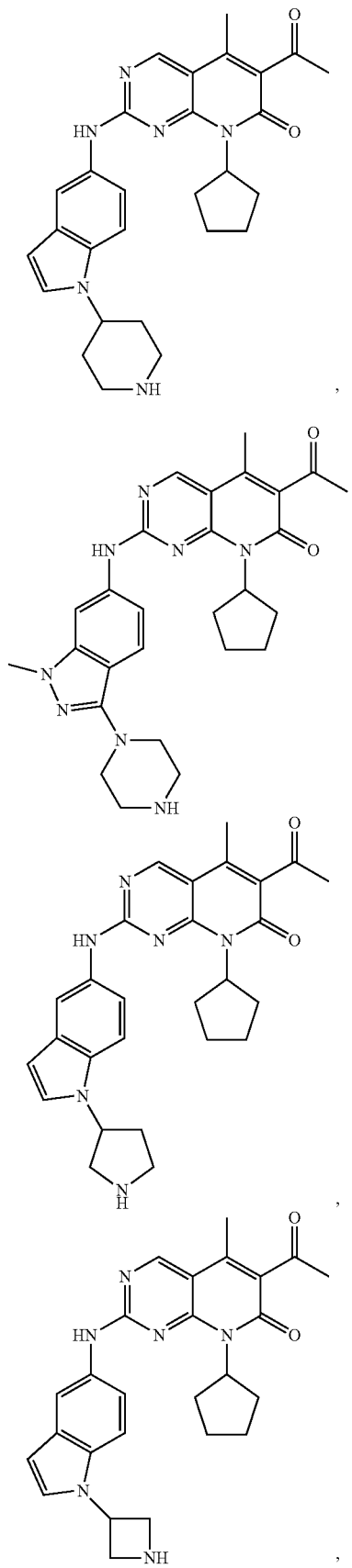
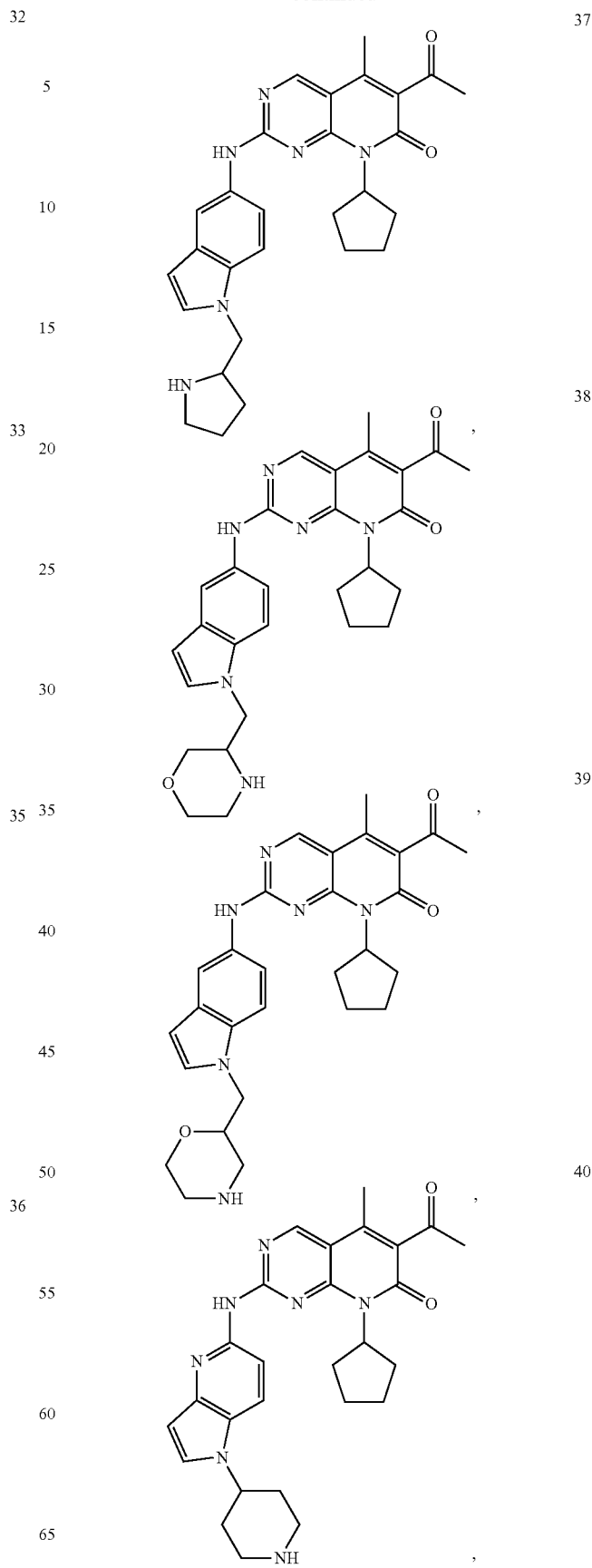

-continued
41
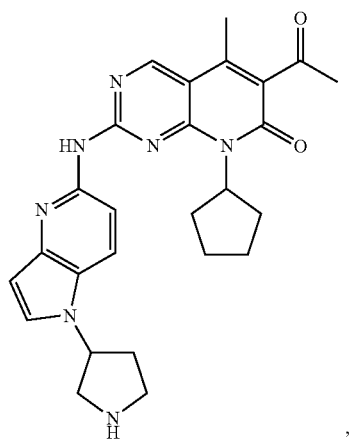
42
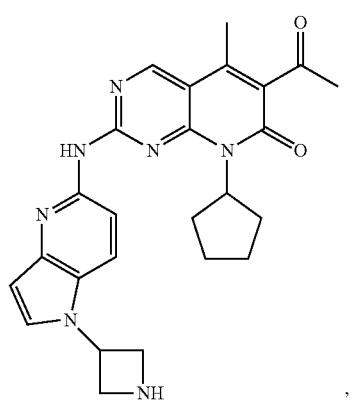
43
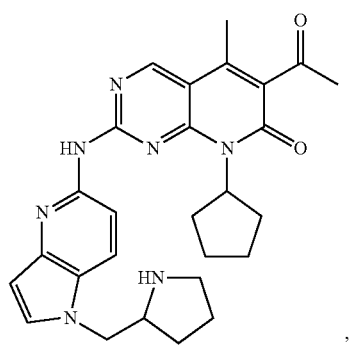
44
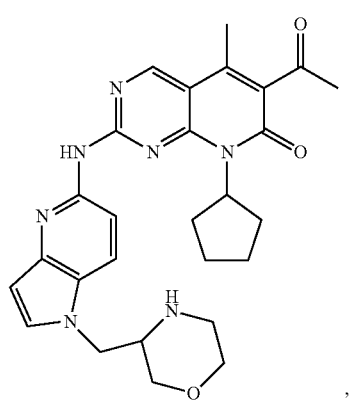
-continued
45
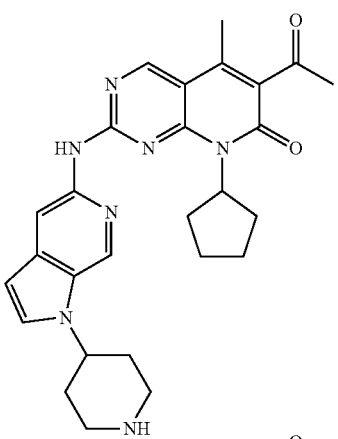
46
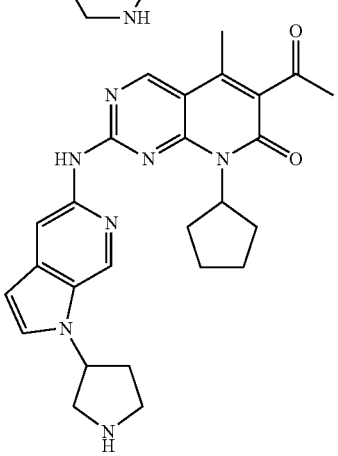
47
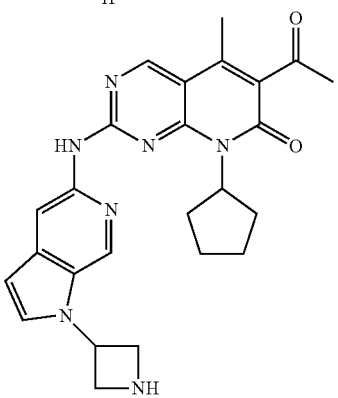
48
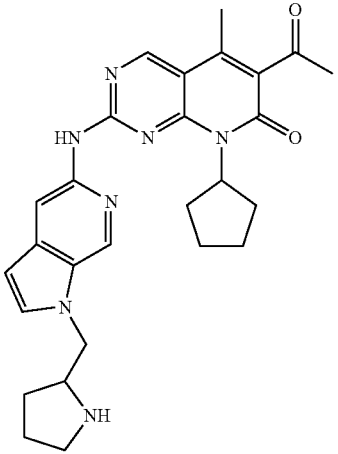

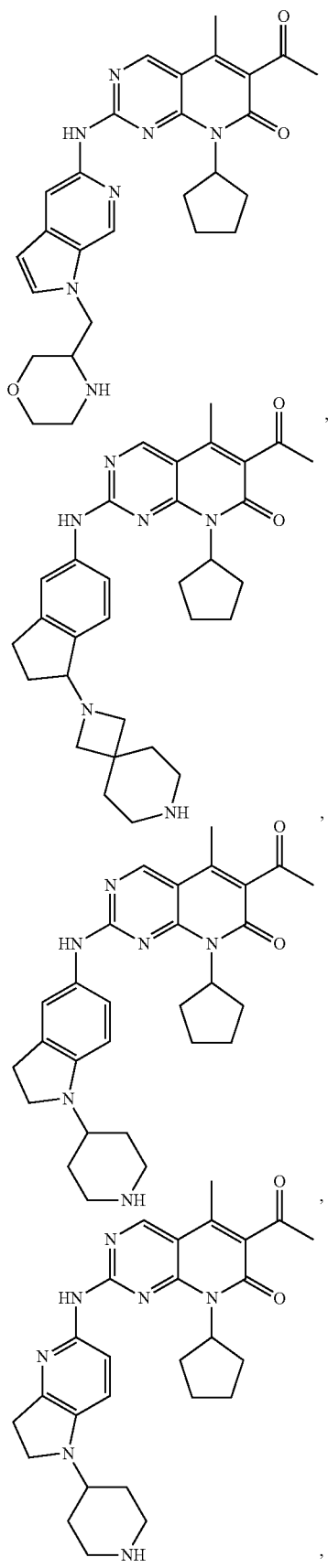
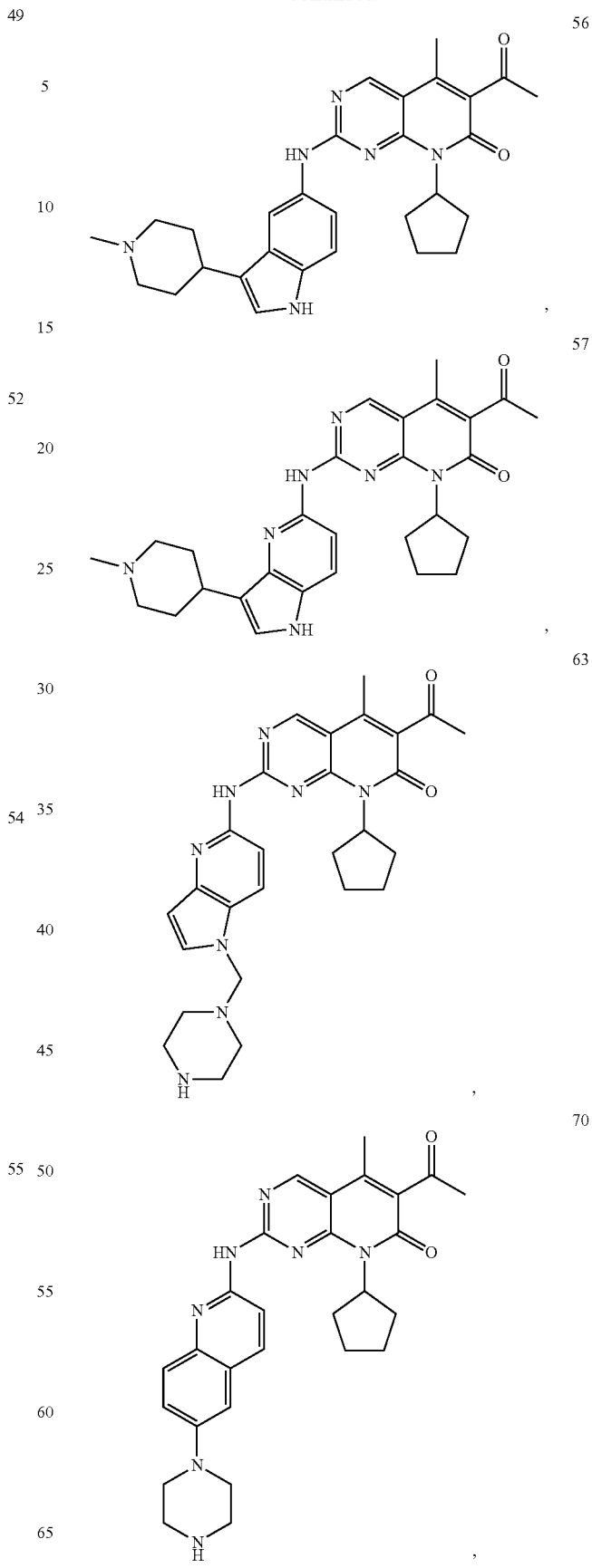

77
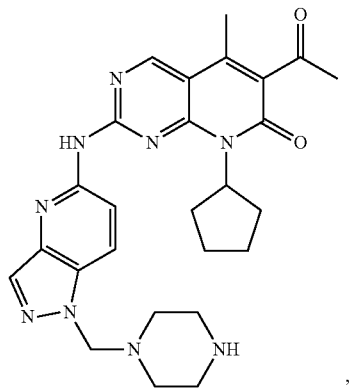
79
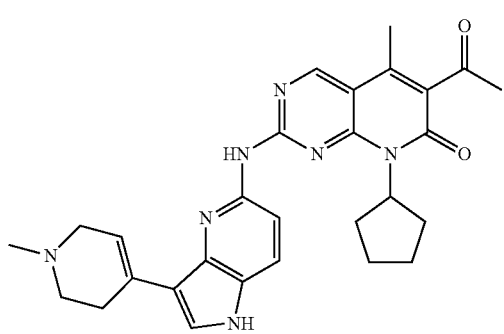
80
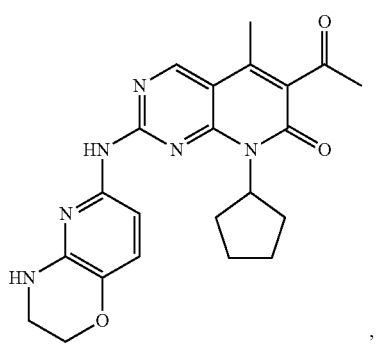
82
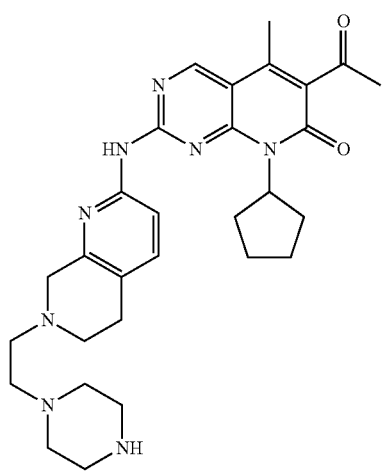
103
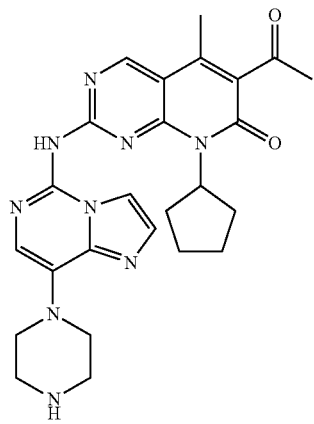
104
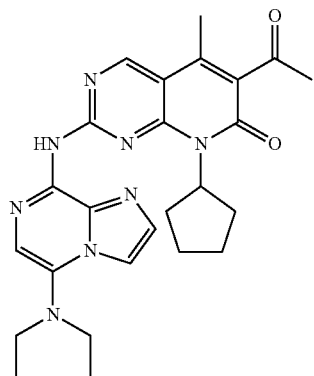
105
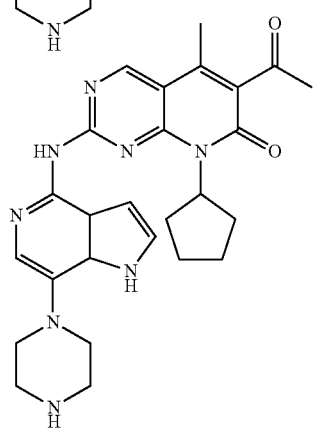
107
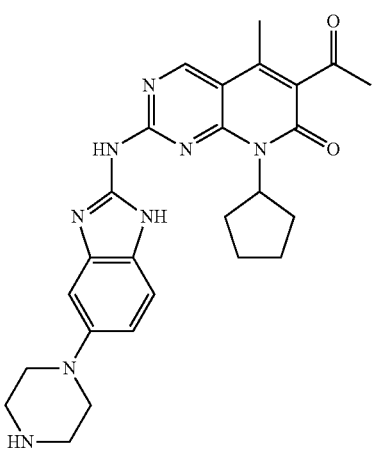

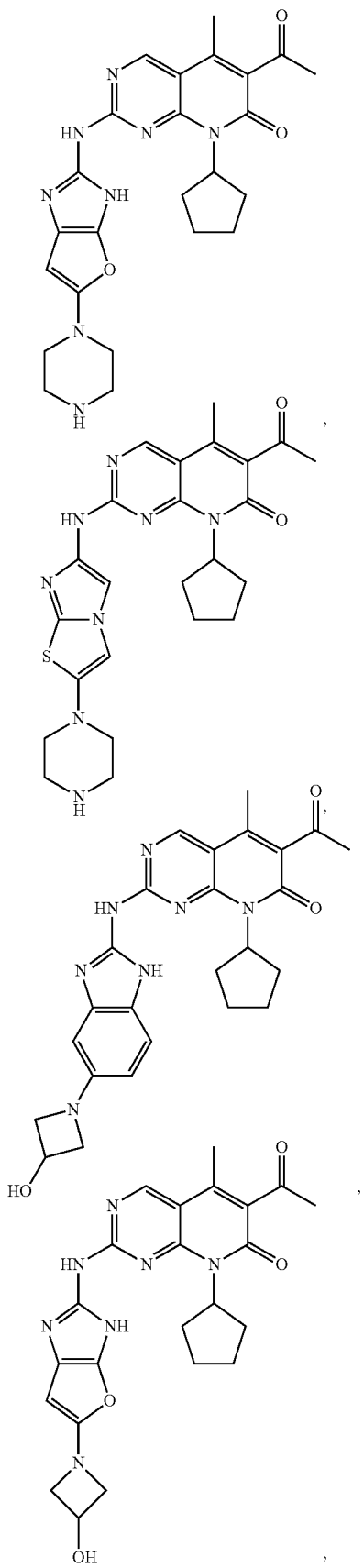
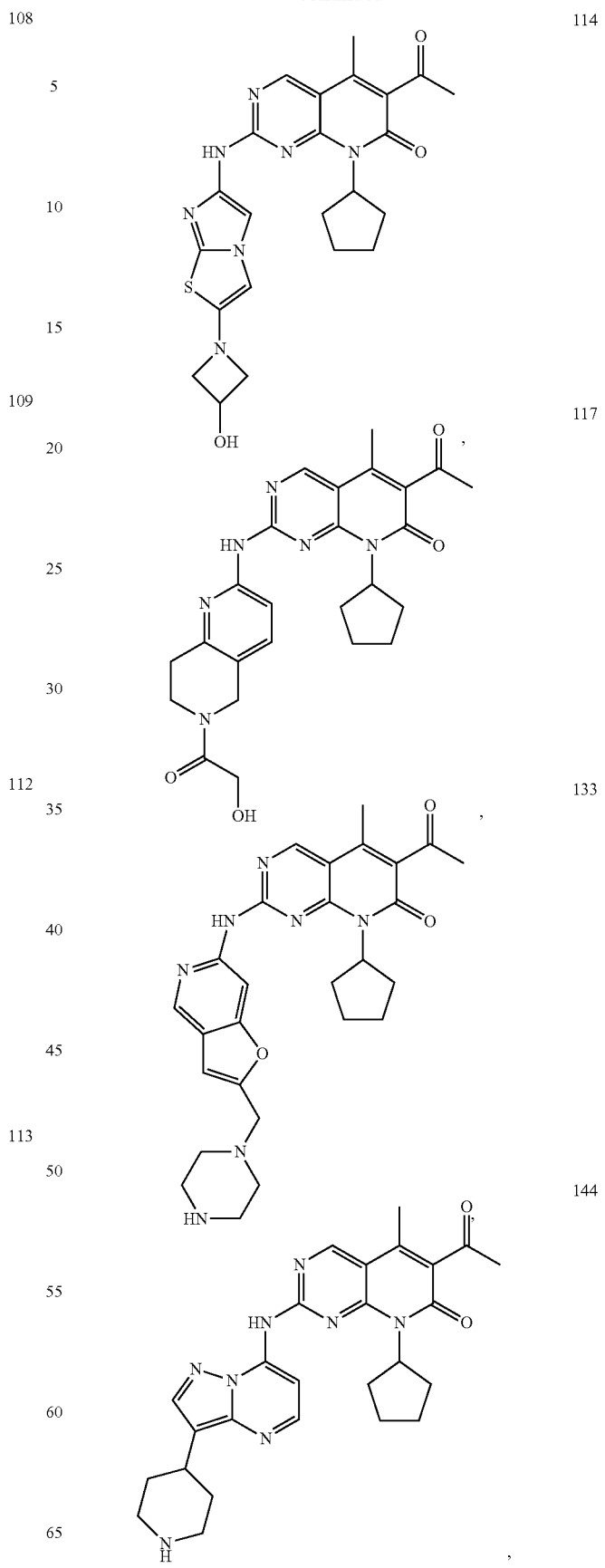

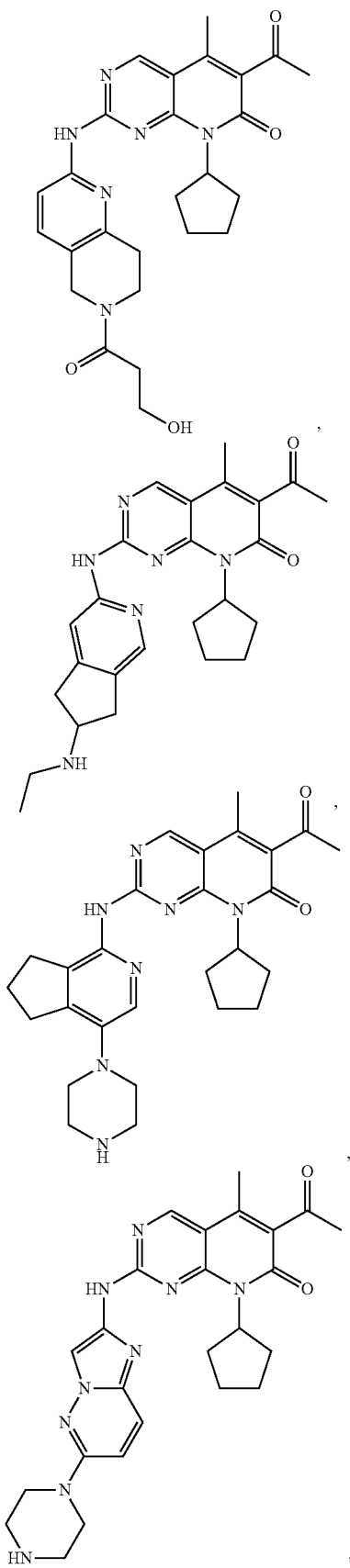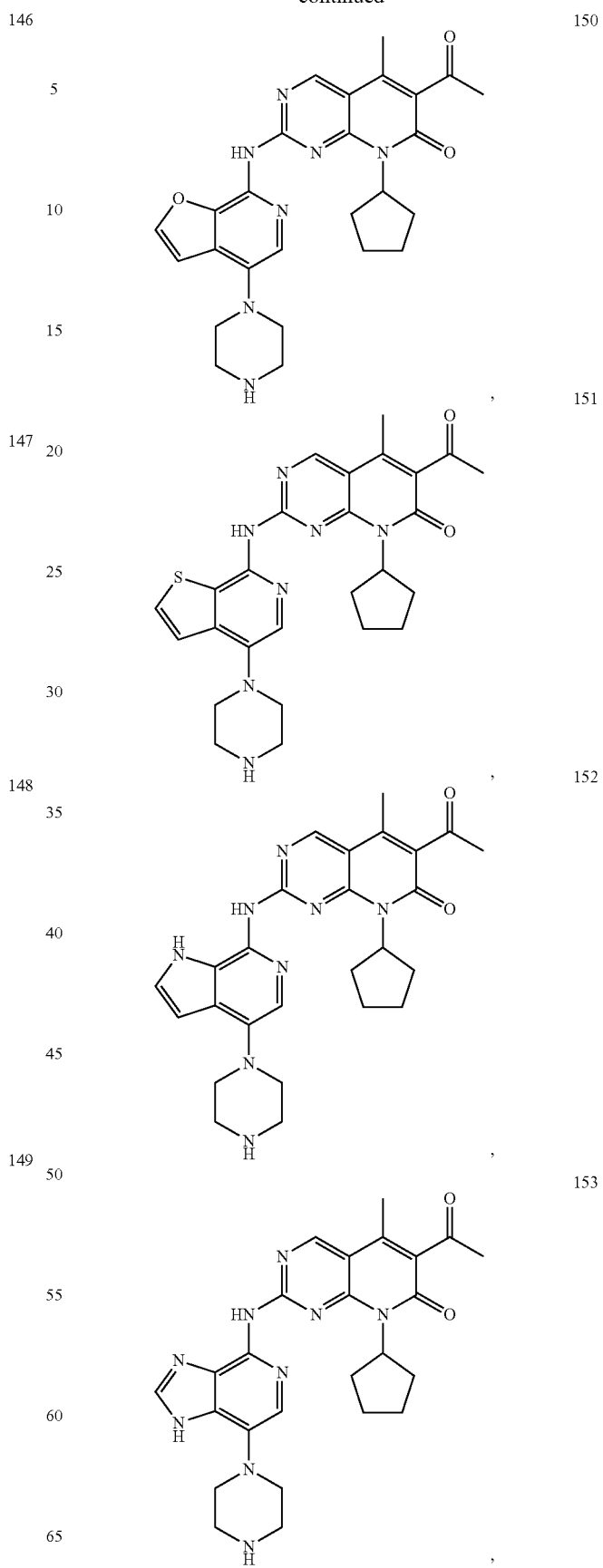

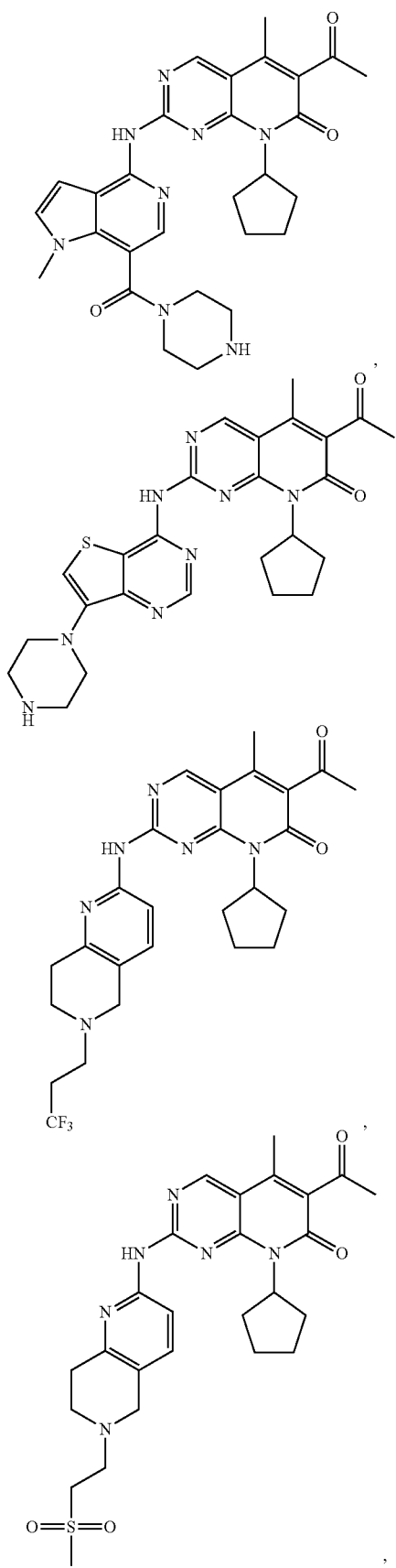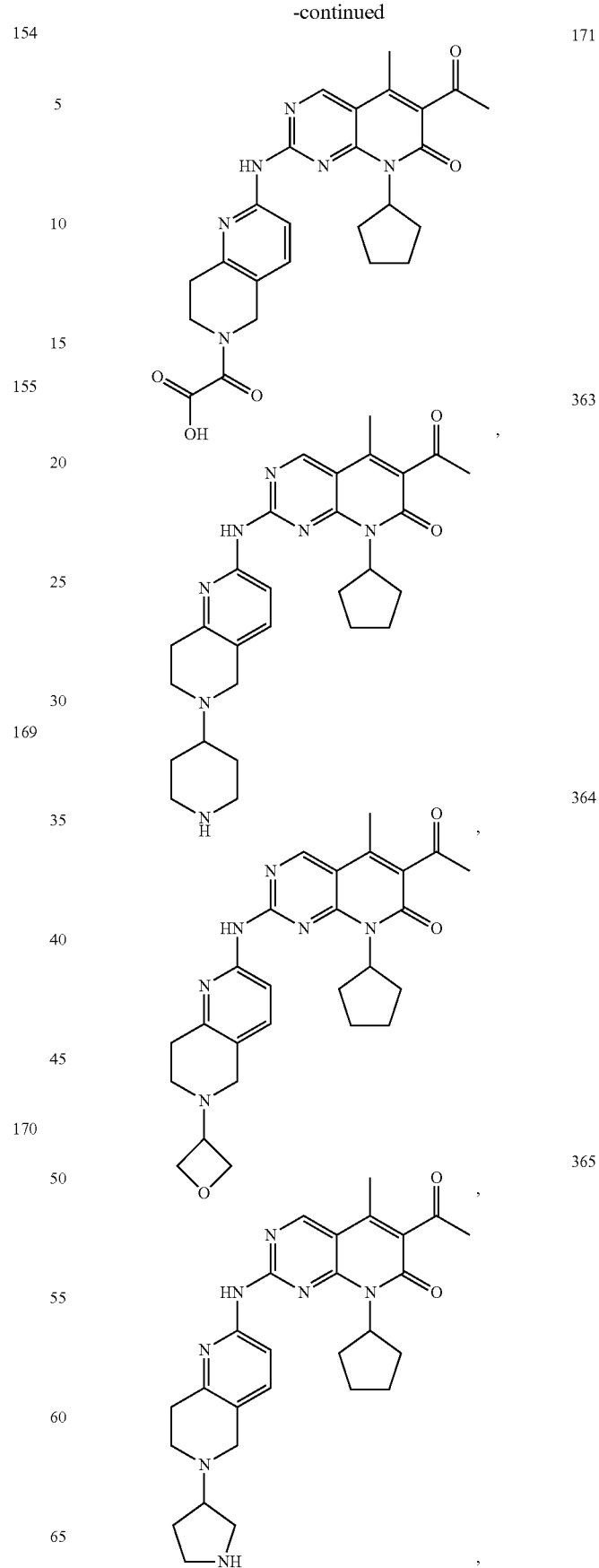

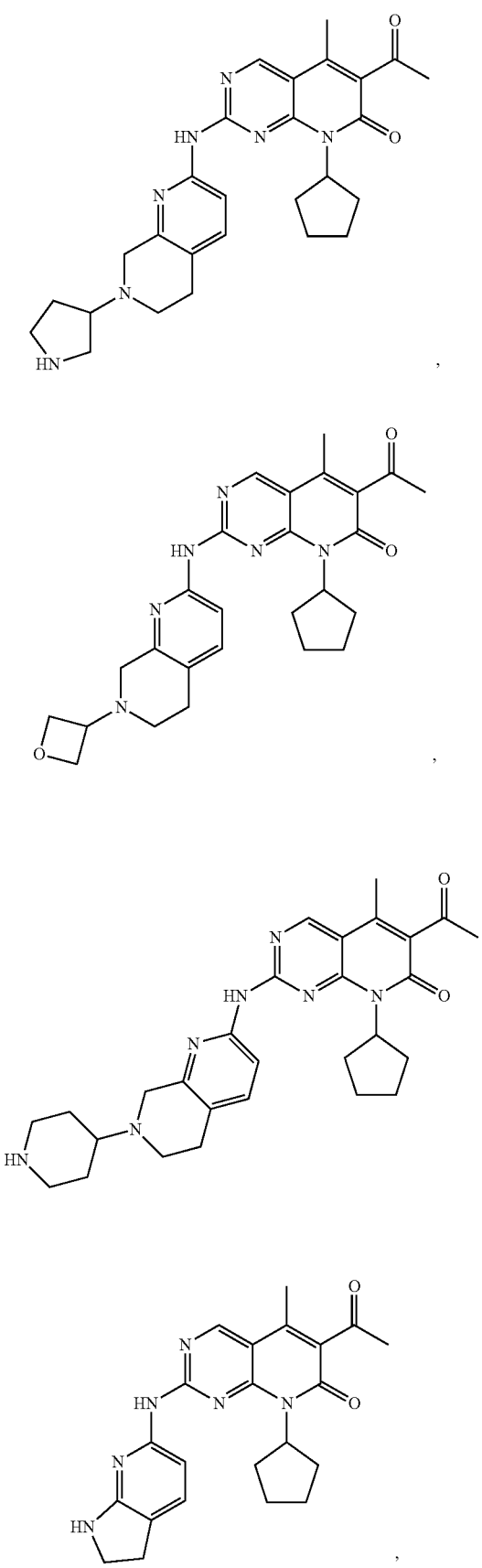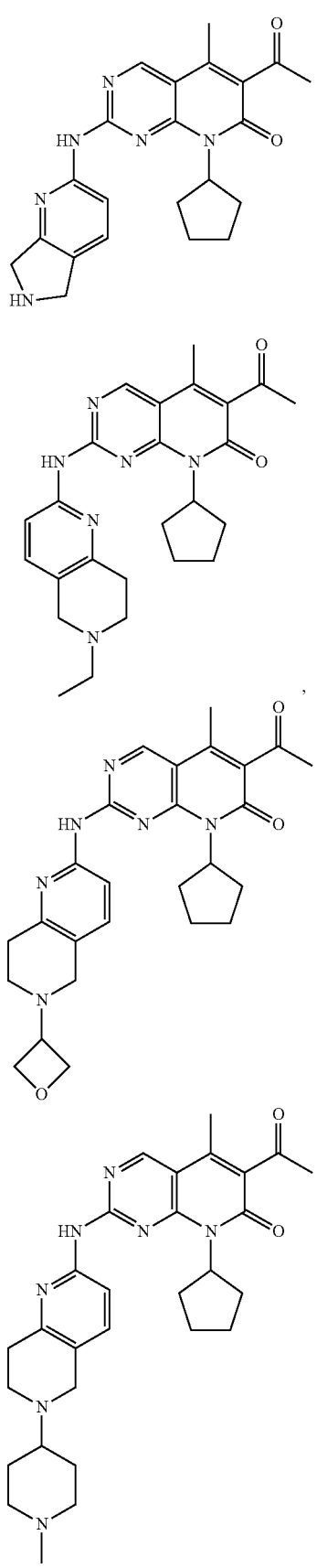

-continued

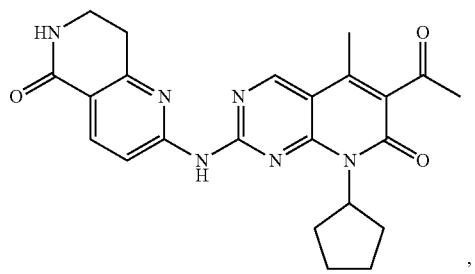
377

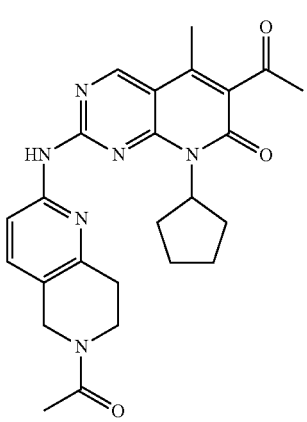
378

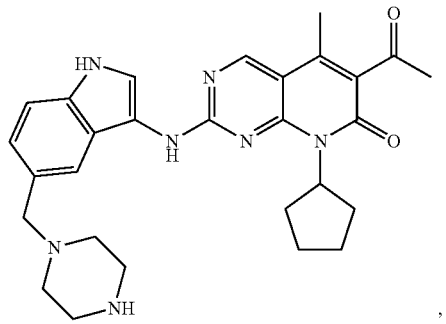
379

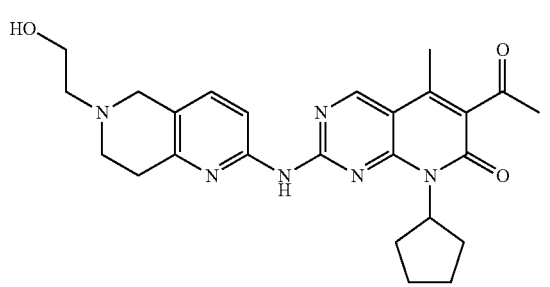
380
or
381

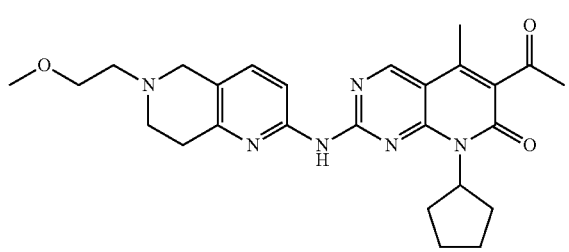

In other aspect, provided herein is a pharmaceutical composition comprising the compound disclosed herein.

In some embodiments, the pharmaceutical composition disclosed herein further comprises at least one of pharmaceutically acceptable carriers, excipients, diluents, adjuvants, vehicles.

In other aspect, provided herein is use of the compound or the pharmaceutical composition disclosed herein in the manufacture a medicament for preventing, managing, treating or lessening disorders or diseases caused by abnormal cell proliferation, autoimmunity, inflammation or infection.

In other aspect, provided herein is a method of using the compound or the pharmaceutical composition disclosed herein in the manufacture a medicament for preventing, managing, treating or lessening disorders or diseases caused by abnormal cell proliferation, autoimmunity, inflammation or infection.

In other aspect, provided herein is the compound or the pharmaceutical composition for use in preventing, managing, treating or lessening disorders or diseases caused by abnormal cell proliferation, autoimmunity, inflammation or infection In some embodiments of the use of the invention, the abnormal cell proliferation disorder or disease is ovarian cancer, cervical cancer, testiculoma, esophagus cancer, gastric cancer, skin cancer, lung cancer, osteocarcinoma, acute myeloid leukemia, chronic myelogenous leukemia, gastrointestinal stromal tumor, acute myelocytic leukemia (AML), chronic myeloid leukemia (CML) with mutation, acute lymphoblastic leukemia (ALL), colorectal cancer, gastric cancer, breast cancer, lung cancer, cancer of the liver, prostate cancer, pancreatic cancer, thyroid cancer, kidney cancer, brain tumor, cervical cancer, cancer of the central nervous system, spongioblastoma or myelodysplastic syndrome, atherosclerosis, pulmonary fibrosis, leukemia, lymph cancer, rheumatic disease, cryoglobulinemia, non-lymphoreticular system tumor, papular mucinosis, familial splenic anemia, multiple myeloma, amyloidosis, solitary plasmacytoma, heavy chain disease, light chain disease, malignant lymphoma, chronic lymphocytic leukemia, primary macroglobulinemia, semi-molecular disease, monocytic leukemia, primary macroglobulinemia purpura, secondary benign monoclonal gammopathy, osteolytic lesion, myeloma, lymphoblastoma, part of the non-Hodgkin's lymphoma, Sezary syndrome, infectious mononucleosis, acute histiocytosis, Hodgkin's lymphoma, hairy cell leukemia, colon cancer, rectal cancer, intestinal polyp, small cell lung cancer, neuroblastoma, neuroendocrine cell tumor, islet cell tumor, medullary thyroid carcinoma, melanoma, retinoblastoma, uterine cancer, head and neck squamous cell carcinoma, alimentary canal malignancy, non-small cell lung cancer, spongioblastoma, mantle cell lymphoma, chronic granulocytic leukemia, acute granulocytic leukemia, bladder cancer or myeloma.

In some embodiments of the use of the invention, the autoimmune disease is rheumatic arthritis, lupus, multiple sclerosis, thyroiditis, type I diabetes, sarcoidosis, inflammatory bowel disease, Crohn's disease or systemic lupus.

In some embodiments of the use of the invention, the inflammatory disease is diverticulitis, colitis, pancreatitis, hepatitis, chronic hepatitis, cirrhosis, cholecystitis or chronic inflammation.

In some embodiments of the use of the invention, the infection disease is virus infection or fungal infection.

In some embodiments of the use of the invention, the disease is a disease caused by changes in cyclin-dependent kinase.

In other embodiments of the use of the invention, the cyclin-dependent kinase is CDK1, CDK2, CDK4, CDK6 or CDK9.

In some embodiments of the use of the invention, the disease is a disease caused by changes in CDK4 or CDK6 protein kinase.

In one aspect, provided herein is a drug combination comprising the compound or the pharmaceutical composition disclosed herein and one or more other activity agents used for treating proliferative diseases, autoimmune diseases or inflammatory diseases.

In some embodiments, the drug combination disclosed herein, the other activity agent comprises chemotherapeutic drug, antiproliferative agent, immunosuppressor, immunologic stimulant, anti-inflammatory agent, CDK4/6 kinase inhibitor, ABL inhibitor, ABL/Scr inhibitor, aurora kinase inhibitor, non-ATP competitive inhibitor of BCR-ABL, c-KIT mutation inhibitor, RET inhibitor, PDGFR inhibitor, VEGFR inhibitor, CSF1R inhibitor, FLT3 inhibitor, FLT3-ITD inhibitor or a combination thereof.

The compound or the pharmaceutical composition of the drug combination disclosed herein is CDK4/6 inhibitor;

Perfectly, the other activity agent is FLT3 inhibitor or FLT3-ITD inhibitor.

Unless otherwise indicated, all stereoisomers, geometric isomers, tautomers, N-oxides, hydrates, solvates, metabolites, pharmaceutically acceptable salts or prodrugs of the compounds disclosed herein are within the scope of the present invention. Specifically, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith. The salt of the compounds disclosed herein also include salts of the compounds which are not necessarily pharmaceutically acceptable salts, and which may be useful as intermediates for preparing and/or purifying compounds of Formula (I)-(III) and/or for separating enantiomers of compounds of Formula (I)-(III).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or the combination thereof.

If the compound disclosed here in is an acid, the desired salt may be prepared by any suitable method, for example, treatment of the free acid with an inorganic or organic base, such as an amine (primary, secondary or tertiary), an alkali metal hydroxide, ammonium, $N^+(R^x)_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^x)_4$ salt, wherein $R^x$ is H, $C_{1-4}$ alkyl, $C_{6-10}$ aryl, $C_{6-10}$ aryl-$C_{1-4}$-alkyl, and the like; and cyclic amines, such as piperidine, morpholine and piperazine, and inorganic salts derived from sodium, calcium, potassium, magnesium, manganese, iron, copper, zinc, aluminum, lithium, and the like, Further include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The compounds of the present invention are CDK4 and CDK6 inhibitors and are therefore useful in the treatment of a disease or disorder characterised by abnormal cell proliferation. In particular, the compounds of the present invention are useful in the treatment of cancer.

CDK4 and CDK6 modulate their effects on the cell cycle through the phosphorylation of pRb. The compounds of the present invention, which are potent inhibitors of CDK4/6 activity and thus pRb phosphorylation, are expected to inhibit cell proliferation (and therefore tumour growth) in any cancer type where the cells are proliferating and contain a functional, intact Rb1 gene (which encodes pRb). The compounds of the invention are therefore useful in the treatment of pRb+ cancers such as colorectal cancer, breast cancer, lung cancer, prostate cancer, chronic myeloid leukaemia, acute myeloid leukaemia (Fry, D. W. et al. Mol. Cancer Ther. (2004), 3(11), 1427), mantel cell lymphoma (Marzec, M. et al., Blood (2006), 108(5), 1744) ovarian cancer (Kim, T. M. et al., Cancer Research (1994), 54, 605), pancreatic cancer (Schutte, M. et al., Cancer Research (1997), 57, 3126) malignant melanoma and metastatic malignant melanoma (Maelandsmo, G. M. et al., British Journal of Cancer (1996), 73, 909) in mammals. The compounds of the invention are also expected to be useful in the treatment of rhabdomyosarcoma (Saab, R. et al., Mol. Cancer. Ther. (2006), 5(5), 1299) and multiple myeloma (Baughn, L. B. et al., Cancer Res. (2006), 66(15), 7661) in mammals. In some embodiments, the mammal to be treated is a human.

The compounds of the invention can be used in the treatment of cancers in mammal, especially in the methods of treating the aforementioned cancers, the methods comprise administrating to the mammal in need of the treatment a therapeutically effective amount of the compounds of the invention.

In some embodiments, the compound of the invention can be used in the methods of treating cancers, the cancer is selected from colorectal cancer, mantle cell lymphoma, breast cancer, spongioblastoma, acute granulocytic leukemia and lung cancer, especially non-small cell lung cancer (NSCLC).

In other embodiments, the compound of the invention can be used in the methods of treating cancers, the cancer is selected from colorectal cancer, spongioblastoma, acute granulocytic leukemia and lung cancer.

In other embodiments, the compound of the invention can be used in the methods of treating spongioblastoma or astrocytoma in mammal, the methods comprise administrating to the mammal in need of the treatment a therapeutically effective amount of a combination of the compounds of the invention and temozolomide.

In other embodiments, the compound of the invention can be used in the methods of treating non-small cell lung cancer, pancreatic cancer, ovarian cancer or metastatic breast cancer in mammal, the methods comprise administrating to the mammal in need of the treatment a therapeutically effective amount of a combination of the compounds of the invention and gemcitabine hydrochloride.

In addition, the compounds of the invention can be used in the manufacture of a medicament for treating cancers, especially the aforementioned cancer.

In some embodiments, the compounds of the invention can be used in the manufacture of a medicament for treating cancers, the cancer is selected from colorectal cancer, mantle cell lymphoma, breast cancer, spongioblastoma, acute granulocytic leukemia and lung cancer, especially non-small cell lung cancer (NSCLC).

In other embodiments, the compounds of the invention can be used in the manufacture of a medicine for treating cancers, the cancer is selected from colorectal cancer, spongioblastoma, acute granulocytic leukemia and lung cancer.

In other embodiments, the present invention provides the use of the compounds of the invention in the manufacture of a medicament for treating spongioblastoma or astrocytoma, wherein the medicament also includes temozolomide or is to be administered simultaneously, separately or sequentially with temozolomide.

In other embodiments, the invention provides the use of a compound of the invention in the manufacture of a medicament for the treatment of NSCLC, pancreatic cancer, ovarian cancer or metastatic breast cancer, wherein the medicament also comprises gemcitabine hydrochloride or is to be administered simultaneously, separately or sequentially with gemcitabine hydrochloride. There is also provided a pharmaceutical formulation for treating cancers, in particular the cancers described above comprising a compound of the present invention or a pharmaceutically acceptable salt thereof together with a pharmaceutically acceptable carrier.

In some embodiments, there is also provided a pharmaceutical formulation for treating a cancer selected from the group consisting of colorectal cancer, mantel cell lymphoma, breast cancer, glioblastoma, acute myeloid leukaemia and lung cancer, especially NSCLC, comprising a compound of the present invention or a pharmaceutically acceptable salt thereof together with a pharmaceutically acceptable carrier.

In some embodiments, there is also provided a pharmaceutical formulation for treating a cancer selected from the group consisting of colorectal cancer, glioblastoma, acute myeloid leukaemia and lung cancer, comprising a compound of the present invention or a pharmaceutically acceptable salt thereof together with a pharmaceutically acceptable carrier.

In other embodiments, the invention provides a pharmaceutical formulation for treating glioblastoma or astrocytoma, comprising a compound of the invention and temozolomide, together with a pharmaceutically acceptable carrier.

In other embodiments, the invention provides a pharmaceutical formulation for treating NSCLC, pancreatic cancer, ovarian cancer or metastatic breast cancer, comprising a compound of the invention and gemcitabine hydrochloride, together with a pharmaceutically acceptable carrier.

The invention also provides a pharmaceutical formulation, comprising a compound of the invention or a pharmaceutically acceptable salt thereof and temozolomide, together with a pharmaceutically acceptable carrier, diluent, or excipient.

The invention also provides a pharmaceutical formulation, comprising a compound of the invention or a pharmaceutically acceptable salt thereof and gemcitabine hydrochloride, together with a pharmaceutically acceptable carrier, diluent, or excipient.

The invention further provides a pharmaceutical formulation comprising a compound of the invention or a pharmaceutically acceptable salt thereof together with a pharmaceutically acceptable carrier and optionally other therapeutic ingredients.

Uses in Cancer, Transplant Rejections, and Autoimmune Diseases

The compounds of the present invention have valuable pharmacological properties and are useful in the treatment of diseases. In certain embodiments, compounds of the invention are useful in the treatment of a proliferative disease, or cancer.

A proliferative disease is mainly a tumor disease (or cancer) (and/or any metastases). The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

In other certain embodiments, compounds of the invention are useful in the treatment of transplant rejections. Examples of transplant rejections that may be treated by the compounds of the invention include, but are not limited to, graft versus host disease, rejection related to xeno transplantation, rejection related to organ transplant, rejection related to acute transplant, heterograft or homograft rejection and ischemic or reperfusion injury incurred during organ transplantation.

In still other certain embodiments, compounds of the invention are useful in the treatment of autoimmune diseases. Examples of autoimmune diseases to be treated by the compounds of the invention include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis, multiple sclerosis, neuritis, uveitis ophthalmia, polyendocrinopathies, purpura, Reiter's Disease, Stiff-Man Syndrome, autoimmune pulmonary inflammation, autism, Guillain-Barre Syndrome, insulin dependent diabetes mellitus, autoimmune inflammatory eye, autoimmune thyroiditis, hypothyroidism, systemic lupus erhythematosus, Goodpasture's syndrome, Pemphigus, Receptor autoimmunities, autoimmune hemolytic anemia, autoimmune thrombocytopenic purpura, rheumatoid arthritis, mixed connective tissue disease, polymyositis/dermatomyositis, pernicious anemia, idiopathic Addison's disease, infertility, glomerulonephritis, bullous pemphigoid, Sjogren's syndrome, diabetes millitus, adrenergic drug resistance, chronic active hepatitis, primary biliary cirrhosis, vitiligo, vasculitis, post-MI, cardiotomy syndrome, urticaria, atopic dermatitis, asthma, inflammatory myopathies, chronic active hepatitis, primary biliary cirrhosis and T-cell mediated hypersensitivity diseases.

The term "use" includes any one or more of the following embodiments of the invention, respectively: the use in the treatment of protein kinase-associated disorders; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from cancer, transplant rejections, or autoimmune diseases, as well as those diseases that depend on the activity of protein kinases. The term "use" further includes embodiments of compositions herein which bind to a protein kinase sufficiently to serve as tracers or labels, so that when coupled to a fluor or tag, or made radioactive, can be used as a research reagent or as a diagnostic or an imaging agent.

Compositions of the Compounds of the Invention

The invention provides pharmaceutical composition, comprising a therapeutically effective amount of a compound of Formula (I)-(III) or a pharmaceutically acceptable salt thereof and a pharmaceutically acceptable carrier, diluent or excipient. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

"Effective amount" of the compound is that amount necessary or sufficient to treat or prevent a protein kinase-associated disorder, e.g. prevent the various morphological and somatic symptoms of a protein kinase-associated disorder, and/or a disease or condition described herein. In an example, an effective amount of the compound of the invention is the amount sufficient to treat a protein kinase-associated disorder in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a protein kinase-associated disorder. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

By "combination" according to the invention, there is meant either a fixed combination in one dosage unit form, or a kit of parts for the combined administration where a compound of the invention and a combination partner may be administered independently at the same time or separately within time intervals that especially allow that the combination partners show a cooperative, e.g. synergistic effect. The terms "co-administration" or "combined administration" or the like as used herein are meant to encompass administration of the selected therapeutic agents to a single patient, and are intended to include treatment regimens in which the agents are not necessarily administered by the same route of administration or at the same time. The term "pharmaceutical combination" as used herein refers to a product obtained from mixing or combining active ingredients, and includes both fixed and non-fixed combinations of the active ingredients. The term "fixed combination" means that the active ingredients, e.g. a compound disclosed herein and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a protein kinase-associated disorder.

If desired, the effective daily dose of the active compound may be administered as two, three, four, five, six or more sub-doses administered separately at appropriate intervals throughout the day, optionally, in unit dosage forms.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human. In certain embodiments, the subject is a primate.

In yet other embodiments, the subject is a human.

Drug Combinations

Also contemplated herein are combination therapies using one or more compounds or compositions provided herein, or pharmaceutically acceptable derivate, in combination with other pharmaceutically active agents for the treatment of the diseases and disorders described herein.

In practicing the methods, effective amounts of the compounds or compositions containing therapeutically effective concentrations of the compounds, which are formulated for oral, systemic, including parenteral or intravenous delivery, or for local or topical application are administered to an individual exhibiting the symptoms of the disease or disorder to be treated. The amounts are effective to treat, manage or ameliorate the disease or ameliorate or eliminate one or more symptoms of the disease or disorder.

Furthermore, it will be understood by those skilled in the art that the compounds, isomers, prodrugs and pharmaceutically acceptable derivatives provided herein, including pharmaceutical compositions and formulations containing these compounds, can be used in a wide variety of combination therapies to treat the conditions and diseases described above. Thus, also contemplated herein is the use of compounds, isomers, prodrugs and pharmaceutically acceptable derivatives provided herein in combination with other active pharmaceutical agents for the treatment of the disease/conditions described herein.

The compound or composition provided herein, or pharmaceutically acceptable derivative thereof, may be administered simultaneously with, prior to, or after administration of one or more additional agents. The additional agents particularly therapeutic agents known to be useful for treating a proliferative disorder or cancer afflicting the subject.

In some embodiments, the one or more additional agents is selected from anticancer agents (such as a cell signal transduction inhibitors, mitosis inhibitors, alkylating agents, anti-metabolites, intercalating anticancer agents, topoisomerase inhibitors, immunotherapeutic agents, or antihormonal agents), steroid drugs, methotrexates, leflunomides, anti-TNF-α agents, calcineurin inhibitors, antihistaminic drugs, chemotherapeutic drugs, antiproliferative agents, immunosuppressors, immunologic stimulants, apronounced anti-inflammatory reagents, CDK4/6 kinases inhibitors, ABL inhibitors, ABL/Scr inhibitors, aurora kinase inhibitors, non-ATP competitive inhibitors of BCR-ABL, c-KIT mutation inhibitors, RET inhibitors, PDGFR inhibitors, VEGFR inhibitors, CSF1R inhibitors, FLT3 inhibitors, FLT3-ITD inhibitors or a combination thereof.

In some embodiments, anticarcinogen is selected from alkylating agent (such as cyclophosphamide, ifosfamide, melphalan, busulfan, nimustine, ranimustine, dacarbazine, temozolomide, chlormethine hydrochloride, dibromannitol, and the like), platinum complexing agent (such as cisplatinum, carboplatin, oxaliplatin, and the like), metabolic antagonist (such as methotrexate, 5-fluorouracil, tegafur, gemcitabine, capecitabine, fulvestrant, pemetrexed, and the like), plant alkaloid (such as vincristine, vinblastine, vindesine, etoposide, docetaxel, paclitaxel, irinotecan, vinorelbine, mitoxantrone, vinflunine, topotecan, and the like), antibody drug (such as trastuzumab, pertuzumab, rituximab, cetuximab, panitumumab, bevacizumab, and the like), hormone anticancer agent (such as leuprorelin, goserelin, dutasteride, dexamethasone, tamoxifon, and the like), proteasome inhibitor (such as bortezomib, lenalidomide, and the like), aromatase inhibitor (such as exemestane, letrozole, anastrozole, and the like), VEGFR inhibitor (such as sunitinib, sorafenib, imatinib, gefitinib, erlotinib, vandetanib, pazopanib, lapatinib, and the like), mTOR inhibitor (such as everolimus, sirolimus, zotarolimus, and the like).

In some embodiments, the additional agents is selected from streptozotocin, oxaliplatin, temozolomide, methotrexate, fluorouracil, gemcitabine, purinethol, navelbine, docetaxel, topotecan, irinotecan, trabectedin, dactinomycin, mitomycin C, lxabepilone, gonadorelin analogues, megestrol acetate, prednisone, methylprednisolone, thalidomide, interferon α, calcium folinate, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, zelboraf, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, busulfan, sulfonated propyl amine ester, piposulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, prednisone, dexamethasone, leucovorin, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, teniposide, tenuazonic acid, triaziquone, 2,2',2"-trichlorotriethylamine, urethane, vinblastine, vincristine, vindesine, deferasirox, cabozantinib, ponatinib, Midostaurin, Pacritinib, quizartinib, gilteritinib, AKN-028, AT-9283, Crenolanib, ENMD-2076, Famitinib, Dovitinib, PLX-3397, palbociclib, abemaciclib, ribociclib, rigosertib sodium, Selinexor, Ronaciclib, AT-7519, Seliciclib, Alvocidib or a combination thereof.

In some embodiments, the present invention also provided herein a pharmaceutical composition containing compounds disclosed herein or a pharmaceutically acceptable derivate, and one or more other active pharmaceutical agents as a single dosage form or separately from the compound or composition as part of a multiple dosage form. The other active pharmaceutical agents may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

In some embodiments, the present invention also provided herein a combination therapy that treats or prevents the onset of the symptoms, or associated complications of cancer and related diseases and disorders comprising the administration to a subject in need thereof, of one of the compounds or compositions disclosed herein, or pharmaceutically acceptable derivatives thereof, with one or more other active pharmaceutical agents.

In some embodiments, two administrations in drug combinations: 1) the compound or pharmaceutical composition disclosed herein and other active drugs which can be used in combination are in separate formulation, two formulations can be same or different, can be administered either in sequence or simultaneously; when administration in sequence, the second drug is administered during the effective period of the first drug in vivo; 2) the compound or pharmaceutical composition disclosed herein and other active drugs which can be used in combination are in single formulation and administered simultaneously.

In some embodiments, specially provided herein is a drug combination of FLT3 inhibitor or FLT3-ITD inhibitor and CDK4/6 inhibitor. The compound or composition provided herein, or pharmaceutically acceptable derivative thereof as CDK4/6 inhibitor, may be administered simultaneously with, prior to, or after administration of one or more additional agents. The additional agents specially is FLT3 inhibitor or FLT3-ITD inhibitor.

In some embodiments, FLT3 inhibitor or FLT3-ITD inhibitor is cabozantinib, ponatinib, midostaurin, pacritinib, quizartinib, gilteritinib, AKN-028, AT-9283, crenolanib, ENMD-2076, famitinib, dovitinib, PLX-3397, and so on.

General Synthetic Procedures

Generally, the compounds disclosed herein may be prepared by methods described herein, wherein the substituents are as defined for Formula (I)-(III), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra was detected using $CDCl_3$, $d_6$-DMSO, $CD_3OD$ or $d_6$-acetone as solutions (reported in ppm), and using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1311A quaternary pumps, a G1316A TCC (Temperature Control of Column, maintained at 30° C.), a G1329A autosampler and a G1315B DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient condition is shown in Table 1:

TABLE 1

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |

TABLE 1-continued

| Time (min) | A ($CH_3CN$, 0.1% HCOOH) | B ($H_2O$, 0.1% HCOOH) |
|---|---|---|
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron, 10 min, 0.6 mL/min flow rate, 5 to 95% (0.1% formic acid in $CH_3CN$) in (0.1% formic acid in $H_2O$). Column was operated at 40° C.

The following abbreviations are used throughout the application:
BOC, Boc tert-butoxycarbonyl
$CHCl_3$ chloroform
$CDCl_3$ chloroform-d
DMF N,N-dimethylformamide
DMAP 4-dimethylaminopyridine
DMSO dimethyl sulfoxide
DMSO-$d_6$ dimethyl sulfoxide-$d_6$
DIPEA ethyldiisopropylamine
HATU 2-(7-aza-1H-benzotriazole-1-yl)-1,1,3,3-tetramethyluronium hexafluorophosphate
EDC, EDCI 1-(3-dimethylaminopropyl)-3-ethylcarbodiimide hydrochloride
mL, ml milliliter
$N_2$ nitrogen
Pd/C Palladium on activated carbon
RT, rt room temperature
Rt retention time
NaH sodium hydride
TFA trifluoroacetic acid Scheme
Intermediate scheme 1

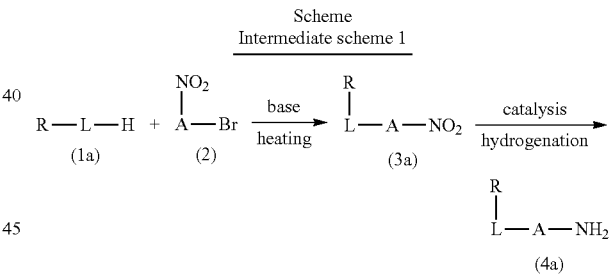

The Intermediate (4a) disclosed herein can be prepared by the process illustrated in intermediate scheme 1. Compound (1a) can react with compound (2) in the present of a base under a heating condition to afford compound (3a); catalytic hydrogenation of compound (3a) in the present of Pd/C can give compound (4a). Wherein A, R and L are as defined herein.

Intermediate scheme 2

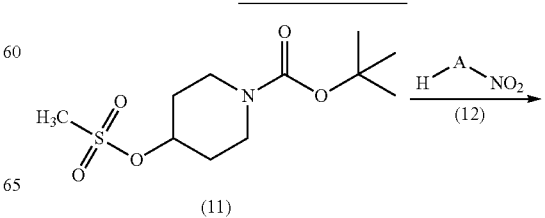

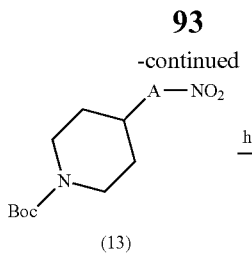

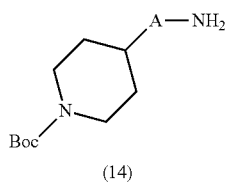

The Intermediate (14) disclosed herein can be prepared by the process illustrated in intermediate scheme 2. Compound (11) can react with compound (12) in the present of a base under a heating condition to afford compound (13); catalytic hydrogenation of compound (13) in the present of Pd/C can give compound (14). Wherein A is as defined herein.

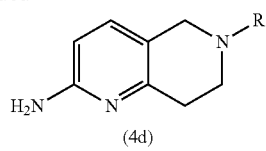

The Intermediate (4d) disclosed herein can be prepared by the process illustrated in intermediate scheme 3. Still reaction of compound (1ad) in the present of toluene-3,4-dithiol can afford compound (1ae); and then compound (1ae) can be cyclized in the present of a base (may be, but not limited RNH₂) under a heating condition to afford compound (1af); amide of compound (1af) can be reduced to afford compound (1ag); methyl of compound (1ag) can be removed in the present of HBr and AcOH to afford compound (1ah); compound (1ah) in the present of POCl₃ can convert to compound (1ai); compound (1ai) can convert to in the present of ammonium hydroxide to compound (4d). Wherein R is as defined herein.

Intermediate scheme 3

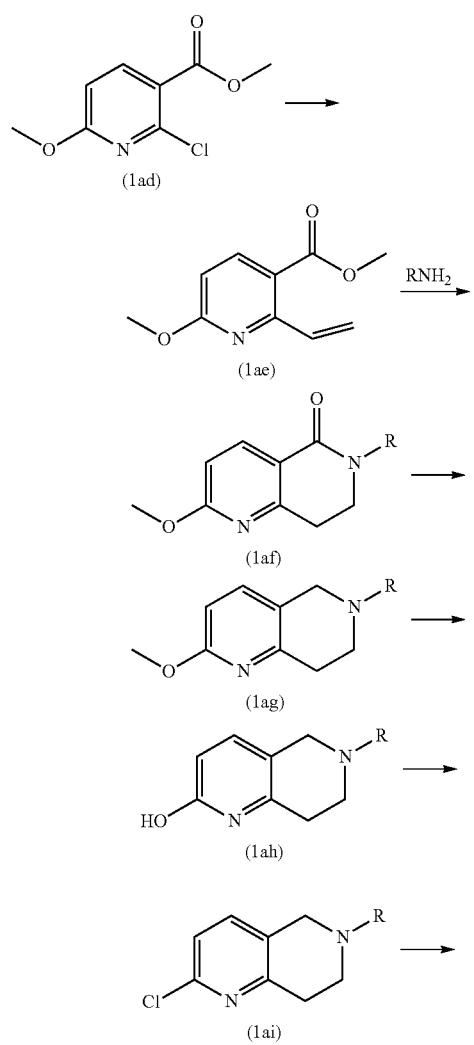

Scheme 1

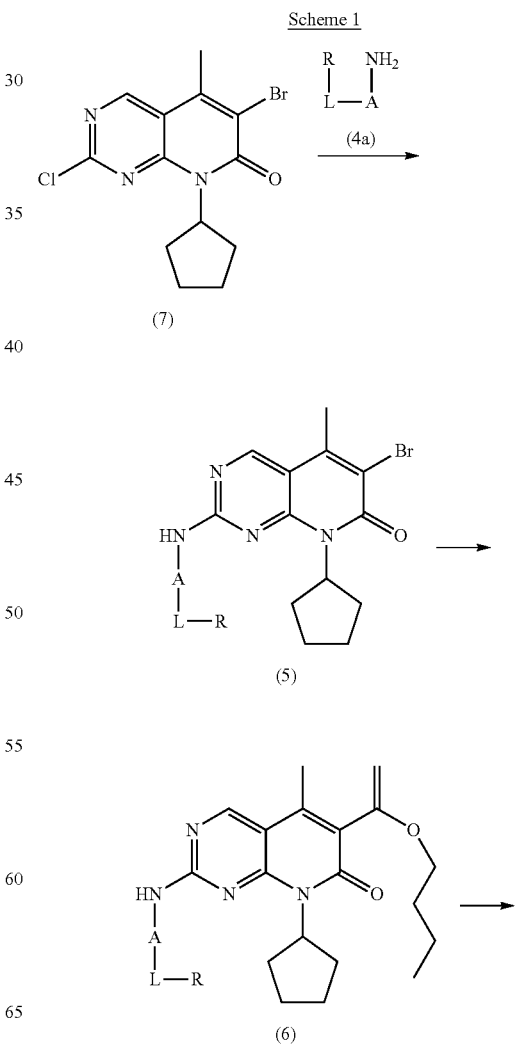

-continued

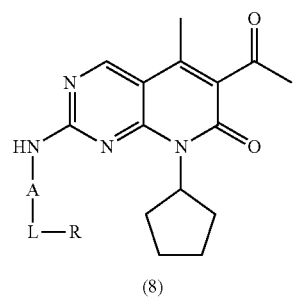

(8)

The compound disclosed herein can be prepared by the process illustrated in scheme 1. Coupling reaction of compound (4a) with compound (7) can afford compound (5) in a suitable solvent; coupling reaction of compound (5) catalyzed by palladium can give compound (6); compound (16) can be rearranged in the present of an acid to afford compound (8). Wherein A, R and L are as defined herein.

Scheme 2

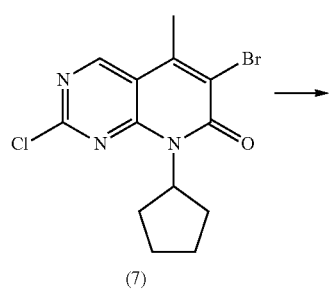

(7)

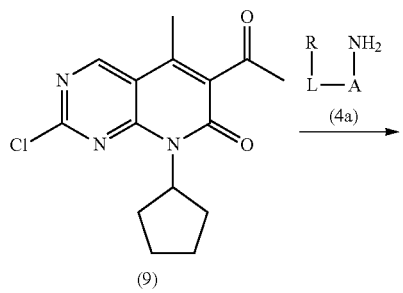

(9)

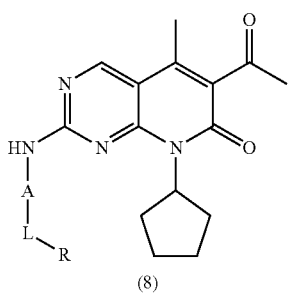

(8)

The compound disclosed herein can be prepared by the process illustrated in scheme 2. Coupling reaction of compound (7) catalyzed by palladium can give compound (9); coupling reaction of compound (9) and compound (4a) in the present of a base can afford compound (8). Wherein A, R and L are as defined herein.

Scheme 3

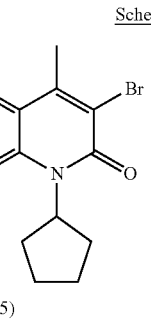

(5)

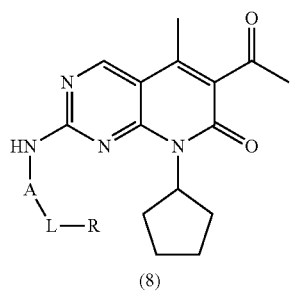

(8)

The compound disclosed herein can be prepared by the process illustrated in scheme 3. Coupling reaction of compound (5) catalyzed by stannum can give compound (8). Wherein A, R and L are as defined herein.

Scheme 4

(14) + (7) ⟶

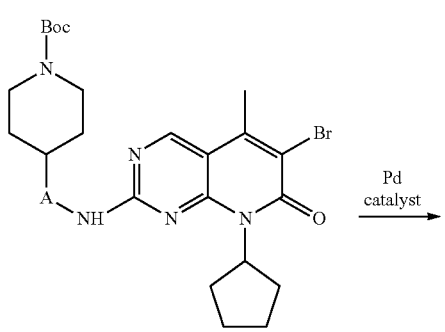

(15)

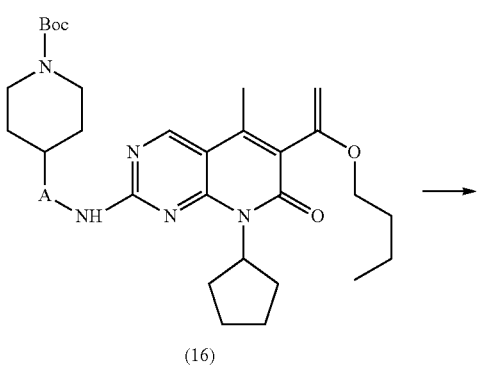

(16)

-continued

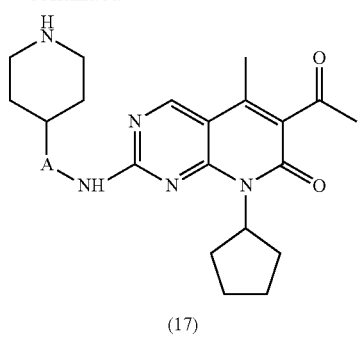

(17)

-continued

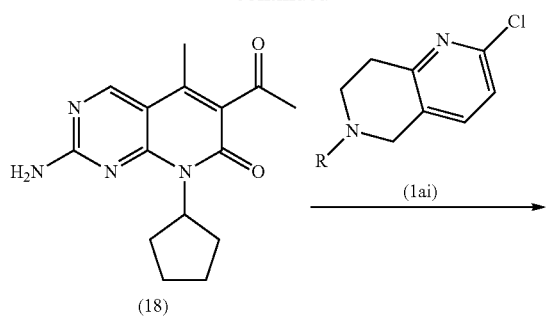

(18)

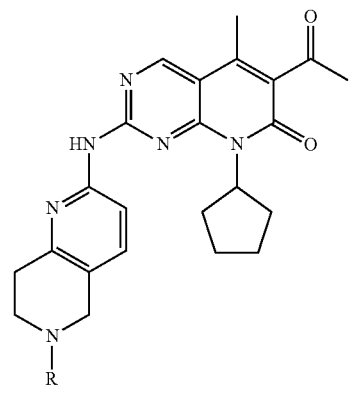

(19)

The compound disclosed herein can be prepared by the process illustrated in scheme 4. Coupling reaction of intermediate (14) and compound (7) can afford compound (15) in a suitable solvent; coupling reaction of compound (15) catalyzed by palladium can give compound (16); compound (6) can be rearranged in the present of an acid to afford compound (17). Wherein A is as defined herein.

The compound disclosed herein can be prepared by the process illustrated in scheme 5. Coupling reaction of compound (7) catalyzed by stannum in a suitable solvent can give compound (10); compound (10) can be rearranged in the present of an acid to afford compound (9); compound (9) can convert to compound (18) in the present of ammonium hydroxide; coupling reaction of compound (18) and compound (1ai) catalyzed by palladium can afford compound (19). Wherein R is as defined herein.

Scheme 5

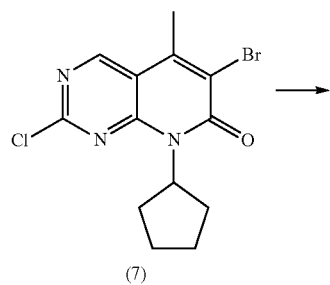

(7)

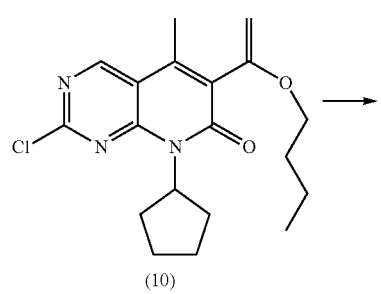

(10)

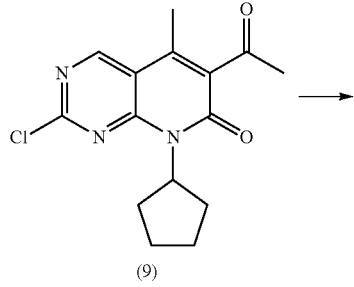

(9)

Scheme 6

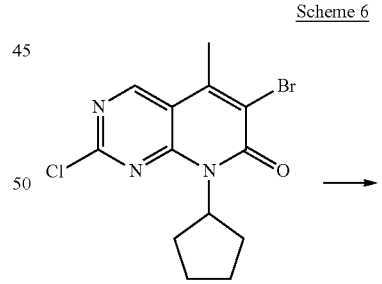

(7)

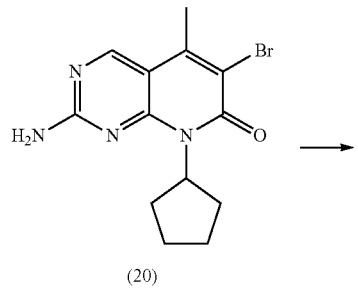

(20)

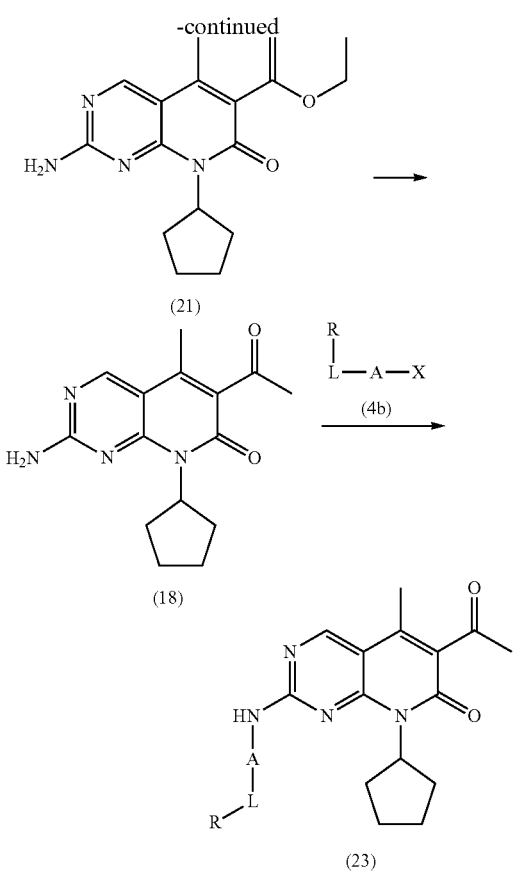

The compound disclosed herein can be prepared by the process illustrated in scheme 6. Compound (7) can convert to compound (20) in the present of ammonium hydroxide; coupling reaction of compound (20) catalyzed by palladium can give compound (21); compound (21) can be rearranged in the present of an acid to afford compound (18); coupling reaction of compound (18) and compound (4b) in the present of a base catalyzed by palladium can afford compound (23). Wherein X is halogen, or other easily-leaving group; A, R and L are as defined herein.

The following examples disclosed herein are presented to further describe the invention. However, these examples should not be used to limit the scope of the invention.

EXAMPLE

Example 1

6-Acetyl-8-cyclopentyl-5-methyl-2-((1-(piperidin-4-yl)-1H-indol-5-yl)amino)pyrido[2,3-d]pyrimidin-7(8H)-one

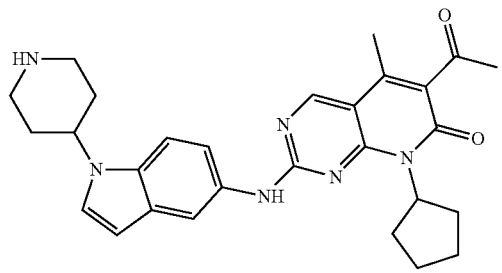 [SMILES: CC(=O)c1c(C)c2cnc(Nc3ccc4c(ccn4C4CCNCC4)c3)nc2n(C2CCCC2)c1=O]

Step 1) tert-butyl 4-(5-nitro-1H-indol-1-yl)piperidine-1-carboxylate

To a solution of 5-nitro-1H-indole (3.0 g, 18.3 mmol) in DMF (45 mL) was added NaH (1.5 g, 38 mmol) in an ice bath. The mixture was stirred at rt for 30 min, a solution of tert-butyl 4-((methylsulfonyl)oxy)piperidine-1-carboxylate (5.2 g, 19 mmol) in DMF (50 mL) was added. The resulting mixture was stirred at 100° C. for 12 h. The reaction mixture was cooled to rt and poured into saturated aqueous sodium bicarbonate solution (150 mL). The mixture was extracted with EtOAc (300 mL×3). The combined organic layers were washed with saturated aqueous NaCl, dried over anhydrous $Na_2SO_4$ and concentrated in vacuo. The residue was purified by silica gel chromatography eluted with PE/EtOAc (V/V)=10/1 to give a yellow oily product (1.1 g, 15.8%).

LC-MS: (pos.ion) m/z: 346.4 $[M+1]^+$;

Step 2) tert-butyl 4-(5-amino-1H-indol-1-yl)piperidine-1-carboxylate

To a solution of tert-butyl 4-(5-nitro-1H-indol-1-yl)piperidine-1-carboxylate (0.80 g, 2 mmol) in methanol (50 mL) was added 10% Pd/C (0.10 g). The system was exchanged with $H_2$ and stirred at rt for 10 h. The reaction mixture was filtered through a Celite pad. The filtrate was concentrated. The residue was purified by silica gel chromatography eluted with DCM/MeOH (V/V)=50/1 to give a brown solid product (0.30 g, 40.1%).

LC-MS: (pos.ion) m/z: 316.3 $[M+1]^+$;

Step 3) tert-butyl 4-(5-(((6-bromo-8-cyclopentyl-5-methyl-7-oxo-7,8-dihydropyrido[2,3-d]pyrimidin-2-yl)amino)-1H-indol-1-yl)piperidine-1-carboxylate To a solution of 6-bromo-2-chloro-8-cyclopentyl-5-methylpyrido[2,3-d]pyrimidin-7(8H)-one (170 mg, 0.5 mmol) (referred to document WO 2003062236A1) and tert-butyl 4-(5-amino-1H-indol-1-yl)piperidine-1-carboxylate (230 mg, 0.73 mmol) in anhydrous DMSO (20 mL) was added powder molecular sieve (200 mg). The system was replaced with $N_2$ and stirred at 120° C. for 12 h. The reaction mixture was cooled to rt and diluted with water. The resulting mixture was extracted with DCM (100 mL×3). The combined organic layers were washed with water (30 mL) and saturated aqueous NaCl (30 mL), dried over anhydrous $Na_2SO_4$ and concentrated in vacuo. The residue was purified by silica gel chromatography eluted with DCM/MeOH (V/V)=20/1 to give a yellow solid product (0.20 g, 60.2%).

LC-MS: (pos.ion) m/z: 621.3 $[M+1]^+$;

Step 4) tert-butyl 4-(5-(((6-acetyl-8-cyclopentyl-5-methyl-7-oxo-7,8-dihydropyrido[2,3-d]pyrimidin-2-yl)amino)-1H-indol-1-yl)piperidine-1-carboxylate To a solution of tert-butyl 4-(5-(((6-bromo-8-cyclopentyl-5-methyl-7-oxo-7,8-dihydropyrido[2,3-d]pyrimidin-2-yl)amino)-1H-indol-1-yl)piperidine-1-carboxylate (130 mg, 0.21 mmol) and [1,1'-bis(diphenylphosphino)ferrocene]dichloropalladium(II) (15 mg, 0.02 mmol) in n-butyl alcohol (20 mL) were added DIPEA (0.05 mL, 0.30 mmol) and n-butyl vinyl ether (0.1 mL, 0.80 mmol). The system was exchanged with $N_2$ and stirred at 95° C. for 10 h. The reaction mixture was concentrated in vacuo and poured into saturated aqueous sodium bicarbonate solution (50 mL). The resulting mixture was extracted with DCM (100 mL×3). The combined organic layers were washed with saturated aqueous NaCl (30 mL), dried over anhydrous Na₂SO₄ and concentrated in vacuo to give a yellow solid product (100 mg, 74.6%).

LC-MS: (pos.ion) m/z: 641.5 [M+1]⁺;

Step 5) 6-acetyl-8-cyclopentyl-5-methyl-2-((1-(piperidin-4-yl)-1H-indol-5-yl)amino)pyrido[2,3-d]pyrimidin-7(8H)-one To a solution of tert-butyl 4-(5-((6-acetyl-8-cyclopentyl-5-methyl-7-oxo-7,8-dihydropyrido[2,3-d]pyrimidin-2-yl)amino)-1H-indol-1-yl)piperidine-1-carboxylate (100 mg, 0.16 mmol) in DCM (20 mL) was added trifluoroacetic acid (0.06 mL, 0.8 mmol). The mixture was refluxed for 12 h. The reaction mixture was cooled and poured into saturated aqueous sodium bicarbonate solution (40 mL). The resulting mixture was extracted with DCM (100 mL×3). The combined organic layers were washed with saturated aqueous NaCl (40 mL), dried over anhydrous Na₂SO₄ and concentrated in vacuo. The residue was purified by prep. HPLC to give a yellow solid product (30 mg, 40.1%).

LC-MS: (pos.ion) m/z: 485.4 [M+1]⁺; and
¹H NMR (400 MHz, DMSO-d₆): δ 10.04-9.88 (m, 1H), 8.91 (s, 1H), 7.93 (s, 1H), 7.52 (d, J=8.8 Hz, 1H), 7.44 (d, J=3.2 Hz, 1H), 7.32 (d, J=8.4 Hz, 1H), 6.39 (d, J=2.8 Hz, 1H), 5.85 (s, 1H), 4.44-4.33 (m, 1H), 3.08 (d, J=12.4 Hz, 2H), 2.71 (t, J=11.2 Hz, 2H), 2.42 (s, 3H), 2.30 (s, 3H), 2.27-2.20 (m, 2H), 2.01-1.94 (m, 1H), 1.89 (d, J=12.4 Hz, 2H), 1.83 (dd, J=11.8 Hz, 3.6 Hz, 2H), 1.77-1.70 (m, 2H), 1.56-1.47 (m, 2H), 1.37-1.28 (m, 2H).

Example 2

6-Acetyl-8-cyclopentyl-5-methyl-2-((7-(1,2,3,6-tetrahydropyridin-4-yl)thieno[3,2-d]pyrimidin-4-yl)amino)pyrido[2,3-d]pyrimidin-7(8H)-one

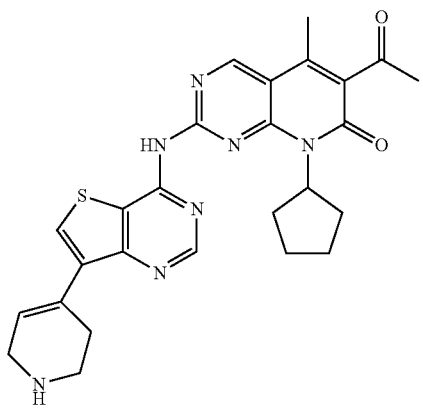 [SMILES: CC(=O)c1c(C)c2cnc(Nc3ncnc4c(C5=CCNCC5)csc34)nc2n(C2CCCC2)c1=O]

Step 1) tert-butyl 4-(4-aminothieno[3,2-d]pyrimidin-7-yl)-5,6-dihydropyridine-1(2H)-carboxylate To a solution of 7-bromothieno[3,2-d]pyrimidin-4-amine (50 mg, 0.21 mmol) and tert-butyl 4-(4,4,5-tetramethyl-1,3,2-dioxaborolan-2-yl)-5,6-dihydropyridine-1(2H)-carboxylate (100 mg, 0.32 mmol) in 1,4-dioxane (10 mL) were added sodium carbonate (72 mg, 0.68 mmol) and Bis(triphenylphosphine)palladium(II) chloride (16 mg, 0.023 mmol). The system was exchanged with N₂ and stirred at 110° C. The mixture was diluted with DCM (100 mL) and washed with saturated aqueous NaCl (20 mL). The combined organic layers were dried over anhydrous Na₂SO₄ and concentrated in vacuo. The residue was purified by silica gel column chromatography eluted with PE/EtOAc (v/v)=1/1 to give a yellow solid product (68 mg, 94%).

LC-MS: (pos.ion) m/z: 333.0 [M+1]⁺;

Step 2) 2-chloro-8-cyclopentyl-6-(1-ethoxyvinyl)-5-methylpyrido[2,3-d]pyrimidin-7(8H)-one To a solution of 6-bromo-2-chloro-8-cyclopentyl-5-methylpyrido[2,3-d]pyrimidin-7(8H)-one (1.00 g, 2.9 mmol) in toluene (40 mL) were added tributyl(1-ethoxyvinyl)stannane (1.05 g, 2.9 mmol) and tetrakis(triphenylphosphine)palladium (0.30 g, 0.26 mmol) in turn. The mixture was stirred at 115° C. for 4 h and filtered. The filtrate was concentrated in vacuo. The residue was purified by silica gel column chromatography eluted with PE/EtOAc (v/v)=5/1 to give a white solid product (614 mg, 62.8%).

LC-MS: (pos.ion) m/z: 334.2 [M+1]⁺;

Step 3) 6-acetyl-2-chloro-8-cyclopentyl-5-methylpyrido[2,3-d]pyrimidin-7(8H)-one To a solution of 2-chloro-8-cyclopentyl-6-(1-ethoxyvinyl)-5-methylpyrido[2,3-d]pyrimidin-7(8H)-one (614 mg, 1.84 mmol) in DCM was added TFA (1.4 mL, 18.4 mmol). The mixture was stirred at 50° C. for 3 h. After the reaction was completed, the reaction mixture was concentrated in vacuo. The residue was purified by silica gel column chromatography eluted with PE/EtOAc (v/v)=5/1 to give a white solid product (334 mg, 61.2%).

LC-MS: (pos.ion) m/z: 306.2 [M+1]⁺;

Step 4) tert-butyl 4-(4-((6-acetyl-8-cyclopentyl-5-methyl-7-oxo-7,8-dihydropyrido[2,3-d]pyrimidin-2-yl)amino)thieno[3,2-d]pyrimidin-7-yl)-5,6-dihydropyridine-1(2H)-carboxylate A mixture of 6-acetyl-2-chloro-8-cyclopentyl-5-methylpyrido[2,3-d]pyrimidin-7(8H)-one (65 mg, 0.21 mmol), tert-butyl 4-(4-aminothieno[3,2-d]pyrimidin-7-yl)-5,6-dihydropyridine-1(2H)-carboxylate (68 mg, 0.20 mmol), [1,1'-bis(diphenylphosphino)ferrocene]dichloropalladium(II) (16 mg, 0.022 mmol) and potassium tert-butoxide (50 mg, 0.42 mmol) in toluene (10 mL) was stirred at 110° C. under N₂ for 6 h. The reaction mixture was diluted with DCM (100 mL). The resulting mixture was filtered through a Celite pad. The filtrate was concentrated in vacuo. The residue was purified by silica gel column chromatography eluted with PE/EtOAc (v/v)=1/1 to give a yellow solid product (16 mg, 13%).

LC-MS: (pos.ion) m/z: 602.3 [M+1]⁺;

Step 5) 6-acetyl-8-cyclopentyl-5-methyl-2-((7-(1,2,3,6-tetrahydropyridin-4-yl)thieno[3,2-d]pyrimidin-4-yl)amino)pyrido[2,3-d]pyrimidin-7(8H)-one To a solution of tert-butyl 4-(4-((6-acetyl-8-cyclopentyl-5-methyl-7-oxo-7,8-dihydropyrido[2,3-d]pyrimidin-2-yl)amino)thieno[3,2-d]pyrimidin-7-yl)-5,6-dihydropyridine-1(2H)-carboxylate (309 mg, 0.51 mmol) in DCM (20 mL) was added TFA (0.8 mL, 10 mmol). The mixture was refluxed for 3 h. The mixture was cooled to rt and diluted with saturated aqueous sodium bicarbonate solution (10 mL). The organic layer was dried over anhydrous Na₂SO₄ and concentrated in vacuo. The residue was purified by silica gel column chromatography eluted with DCM/MeOH (v/v)=10/1 to give a yellow solid product (126 mg, 48.9%).

LC-MS: (pos.ion) m/z: 502.3 [M+1]$^+$; and $^1$H NMR (600 MHz, DMSO-d$_6$) δ 11.32 (s, 1H), 9.13 (d, J=9.8 Hz, 1H), 8.97 (s, 1H), 8.92 (s, 1H), 8.38-8.31 (m, 1H), 7.41 (s, 1H), 5.69 (dt, J=17.1, 8.6 Hz, 1H), 3.88 (s, 2H), 3.17 (m, 2H), 2.83 (s, 2H), 2.46-2.40 (m, 3H), 2.35 (d, J=17.4 Hz, 3H), 2.24-2.15 (m, 2H), 1.77-1.63 (m, 4H), 1.40 (d, J=4.4 Hz, 2H).

Example 3

6-Acetyl-8-cyclopentyl-5-methyl-2-((5,6,7,8-tetra-hydro-1,6-naphthyridin-2-yl)amino)pyrido[2,3-d]pyrimidin-7(8H)-one

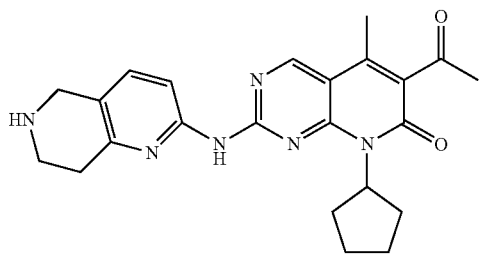 [SMILES: CC(=O)c1c(C)c2cnc(Nc3ccc4c(n3)CCNC4)nc2n(C2CCCC2)c1=O]

Step 1) tert-butyl 2-((6-acetyl-8-cyclopentyl-5-methyl-7-oxo-7,8-dihydropyrido[2,3-d]pyrimidin-2-yl)amino)-7,8-dihydro-1,6-naphthyridine-6(5H)-carboxylate A mixture of 6-acetyl-2-chloro-8-cyclopentyl-5-methyl-pyrido[2,3-d]pyrimidin-1,6(-8H)-one (502 mg, 1.64 mmol), tert-butyl 2-amino-7,8-dihydro-1,6-naphthyridine-6(5H)-carboxylate (329 mg, 1.32 mmol), [1,1'-bis(diphenylphosphino)ferrocene]dichloropalladium(II) (97 mg, 0.13 mmol) and potassium tert-butoxide (308 mg, 2.61 mmol) in toluene (30 mL) was stirred at 110° C. under N$_2$ for 4 h. The reaction mixture was diluted with DCM (100 mL). The resulting mixture was filtered through a Celite pad. The filtrate was concentrated in vacuo. The residue was purified by silica gel column chromatography eluted with PE/EtOAc (v/v)=1/1 to give a yellow solid product (189 mg, 27.6%).

LC-MS: (pos.ion) m/z: 519.5 [M+1]$^+$;

Step 2) 6-acetyl-8-cyclopentyl-5-methyl-2-((5,6,7,8-tetrahydro-1,6-naphthyridin-2-yl)amino)pyrido[2,3-d]pyrimidin-7(8H)-one To a solution of tert-butyl 2-((6-acetyl-8-cyclopentyl-5-methyl-7-oxo-7,8-dihydropyrido[2,3-d]pyrimidin-2-yl)amino)-7,8-dihydro-1,6-naphthyridine-6(5H)-carboxylate (52 mg, 0.1 mmol) in methanol (10 mL) in a 100 mL of one-neck flask was added a methanol solution of HCl (30%, 15 mL) in an ice bath. The mixture was stirred for 30 min and further stirred at rt for 3 h. The reaction mixture was concentrated in vacuo. To the residue was added triethylamine (10 mL) in an ice bath, the mixture was stirred for 1 h. The mixture was stirred for 1 h and concentrated in vacuo. The residue was purified by silica gel chromatography eluted with DCM/MeOH (V/V)=10/1 to give a light yellow solid product (33 mg, 79.7%).

LC-MS: (pos.ion) m/z: 419.6 [M+1]$^+$; and $^1$H NMR (400 MHz, DMSO-d$_6$) δ 10.42 (s, 1H), 9.01 (s, 1H), 7.97 (d, J=8.5 Hz, 1H), 7.70 (d, J=8.6 Hz, 1H), 5.95-5.79 (m, 1H), 4.30 (s, 2H), 3.51 (m, 2H), 3.02 (t, J=6.1 Hz, 2H), 2.43 (s, 3H), 2.33 (s, 3H), 2.30-2.21 (m, 2H), 1.96 (s, 3H), 1.86-1.74 (m, 2H), 1.66-1.56 (m, 2H).

Example 4

6-Acetyl-8-cyclopentyl-2-((6-(2-hydroxyacetyl)-5,6,7,8-tetrahydro-1,6-naphthyridin-2-yl)amino)-5-methylpyrido[2,3-d]pyrimidin-7(8H)-one

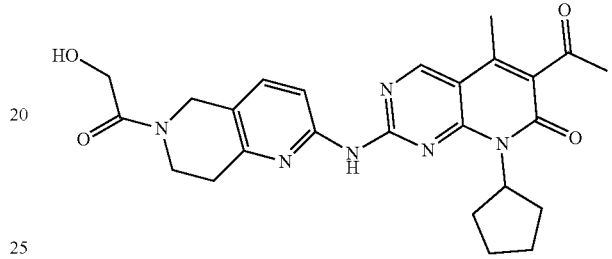

To a solution of glycolic acid (119 mg, 1.56 mmol) in N,N-dimethylformamide (20 mL, 258 mmol, 99.9 mass %) were added HATU (612 mg, 1.56 mmol) and DIPEA (0.30 mL, 1.8 mmol). After stirring for 10 min, to the mixture was added 6-acetyl-8-cyclopentyl-5-methyl-2-((5,6,7,8-tetrahydro-1,6-naphthyridin-2-yl)amino)pyrido[2,3-d]pyrimidin-7(8H)-one (669 mg, 1.60 mmol). The resulting mixture was stirred at rt for 10 h. The mixture was concentrated in vacuo and the residue was purified by silica gel chromatography eluted with DCM/MeOH (V/V)=20/1 to give a yellow solid product (207 mg, 27.9%).

LC-MS: (pos.ion) m/z: 477.5 [M+1]$^+$; and $^1$H NMR (600 MHz, DMSO-d$_6$) δ 10.32 (d, J=12.1 Hz, 1H), 9.00 (s, 1H), 7.95-7.89 (m, 1H), 7.66 (dd, J=34.7, 8.3 Hz, 1H), 5.86 (dt, J=17.8, 8.8 Hz, 1H), 4.74-4.54 (m, 4H), 4.21 (dd, J=20.6, 5.1 Hz, 2H), 3.82 (s, 1H), 3.69 (d, J=5.4 Hz, 2H), 2.43 (s, 3H), 2.32 (s, 3H), 2.26 (s, 2H), 1.94 (s, 2H), 1.78 (dd, J=18.1, 14.5 Hz, 2H), 1.65-1.56 (m, 2H).

Example 5

6-Acetyl-8-cyclopentyl-5-methyl-2-((6-(3,3,3-trifluoropropyl)-5,6,7,8-tetrahydro-1,6-naphthyridin-2-yl)amino)pyrido[2,3-d]pyrimidin-7(8H)-one

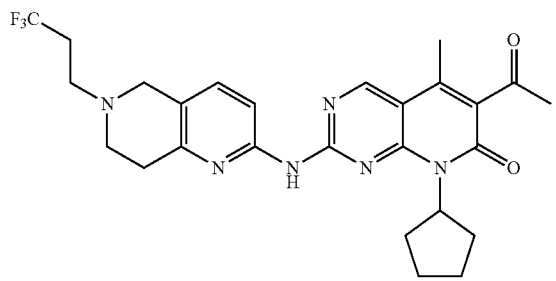

To a solution of 6-acetyl-8-cyclopentyl-5-methyl-2-((5,6,7,8-tetrahydro-1,6-naphthyridin-2-yl)amino)pyrido[2,3-d]

pyrimidin-7(8H)-one (419 mg, 1.0 mmol) in DCM (40 mL) in a 100 mL of one-neck flask was added 3,3,3-trifluoropropanal and (56 mg, 1.2 mmol) and sodium cyanoborohydride (91 mg, 1.2 mmol) in an ice bath. The mixture was stirred for 30 min and further stirred at rt for 6 h. The reaction mixture was concentrated in vacuo. To the residue was added DCM (100 mL) and water (100 mL). The organic layer was washed with saturated aqueous sodium bicarbonate (80 mL×3), saturated aqueous NaCl (80 mL×1) and dried over anhydrous Na$_2$SO$_4$. The residue was purified by silica gel chromatography eluted with DCM/MeOH (V/V)=10/1 to give a light yellow solid product (243 mg, 47.44%).

MS-ESI: (ESI, pos.ion) m/z: 515.3 [M+1]$^+$; and $^1$H NMR (600 MHz, CDCl$_3$) δ 8.87 (s, 1H), 8.34 (s, 1H), 8.13 (d, J=8.4 Hz, 1H), 7.42 (d, J=8.5 Hz, 1H), 5.93-5.84 (m, 1H), 3.70-3.64 (m, 2H), 3.00 (t, J=5.7 Hz, 2H), 2.90 (t, J=5.9 Hz, 2H), 2.88-2.82 (m, 2H), 2.57 (s, 3H), 2.46 (dt, J=10.5, 9.2 Hz, 2H), 2.40 (s, 3H), 2.37 (dd, J=13.3, 5.5 Hz, 2H), 2.09 (dt, J=13.5, 6.9 Hz, 2H), 1.94-1.85 (m, 2H), 1.74-1.68 (m, 2H).

Example 6

6-Acetyl-2-((6-acetyl-5,6,7,8-tetrahydro-1,6-naphthyridin-2-yl)amino)-8-cyclopentyl-5-methylpyrido[2,3-d]pyrimidin-7(8H)-one

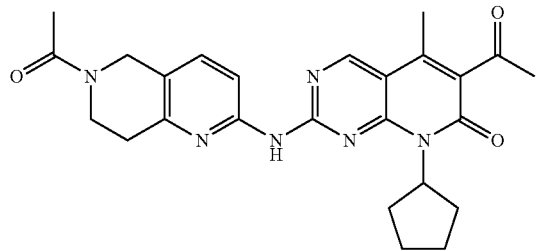 [SMILES: CC(=O)c1c(C)c2cnc(Nc3ccc4c(n3)CCN(C(C)=O)C4)nc2n(C2CCCC2)c1=O]

To a solution of acetic acid (30.8 mg, 0.51 mmol) in N,N-dimethylformamide (15 mL) were added HATU (172 mg, 0.44 mmol) and N,N-diisopropylethylamine (0.10 mL, 0.59 mmol). After stirring for 10 min, 6-acetyl-8-cyclopentyl-5-methyl-2-((5,6,7,8-tetrahydro-1,6-naphthyridin-2-yl)amino)pyrido[2,3-d]pyrimidin-7(8H)-one (171 mg, 0.41 mmol) was added to the mixture. The mixture was stirred at rt for 6 h. The reaction mixture was concentrated in vacuo. To the residue was added silica gel, the resulting mixture was purified by silica gel chromatography eluted with DCM/MeOH (V/V)=10/1 to give a yellow solid product (143 mg, 76.3%).

LC-MS: (pos.ion) m/z: 461.5 [M+1]$^+$; and $^1$H NMR (600 MHz, CDCl$_3$) δ 8.84 (d, J=4.3 Hz, 1H), 8.20 (dd, J=13.4, 8.6 Hz, 1H), 8.12 (s, 1H), 7.49 (dd, J=15.7, 8.5 Hz, 1H), 5.94-5.79 (m, 1H), 4.75 (s, 1H), 3.94 (t, J=5.9 Hz, 1H), 3.80 (t, J=5.9 Hz, 1H), 3.71 (s, 1H), 2.99 (t, J=5.7 Hz, 1H), 2.93 (t, J=5.7 Hz, 1H), 2.54 (d, J=8.6 Hz, 3H), 2.38 (d, J=8.7 Hz, 3H), 2.36 (s, 2H), 2.22 (d, J=7.9 Hz, 3H), 2.08 (s, 2H), 1.91-1.85 (m, 2H), 1.70 (m, 2H).

Example 7

6-Acetyl-2-((6-ethyl-5,6,7,8-tetrahydro-1,6-naphthyridin-2-yl)amino)-8-cyclopentyl-5-methylpyrido[2,3-d]pyrimidin-7(8H)-one

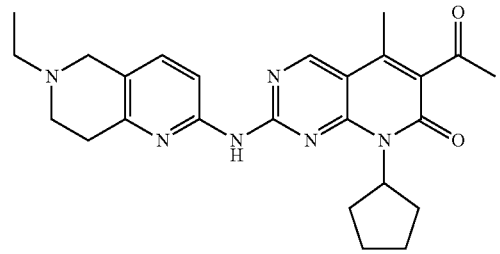 [SMILES: CCN1CCc2nc(Nc3ncc4c(C)c(C(C)=O)c(=O)n(C5CCCC5)c4n3)ccc2C1]

To a solution of 6-acetyl-8-cyclopentyl-5-methyl-2-((5,6,7,8-tetrahydro-1,6-naphthyridin-2-yl)amino)pyrido[2,3-d]pyrimidin-7(8H)-one (213 mg, 0.51 mmol) in N,N-dimethylformamide (15 mL) were added iodoethane (119 mg, 0.76 mmol) and potassium carbonate (141 mg, 1.02 mmol). The mixture was stirred at rt. After the reaction was completed, the mixture was concentrated in vacuo. To the residue was added silica gel for sample. The sample was purified by silica gel chromatography eluted with DCM/MeOH (V/V)=10/1 to give a yellow solid product (199 mg, 87.4%).

LC-MS: (pos.ion) m/z: 447.5 [M+1]$^+$; and $^1$H NMR (600 MHz, CDCl$_3$) δ 8.85 (s, 1H), 8.20-8.10 (m, 2H), 7.42 (d, J=8.5 Hz, 1H), 5.86 (dt, J=17.9, 8.9 Hz, 1H), 3.76 (s, 2H), 3.05 (d, J=18.7 Hz, 2H), 3.04 (s, 2H), 2.78 (d, J=5.4 Hz, 3H), 2.58 (d, J=11.5 Hz, 3H), 2.42-2.38 (m, 2H), 2.38-2.32 (m, 2H), 2.08 (dd, J=12.7, 8.9 Hz, 2H), 1.89 (dd, J=12.1, 8.4 Hz, 2H), 1.82-1.74 (m, 2H), 1.30 (d, J=5.5 Hz, 3H).

Examples 8-38

The following compounds were prepared by a similar method to that described in example 1 or 2 by using suitable raw materials:

| Example | Structure | MS [M + 1]$^+$ |
|---|---|---|
| 8 | 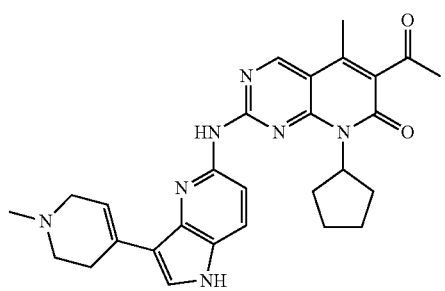 [SMILES: CC(=O)c1c(C)c2cnc(Nc3ccc4[nH]cc(C5=CCN(C)CC5)c4n3)nc2n(C2CCCC2)c1=O] | 498.59 |

| Example | Structure | MS [M+1]+ |
|---|---|---|
| 9 | 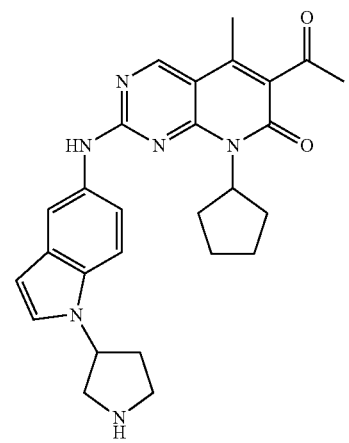 [SMILES: CC(=O)c1c(C)c2cnc(Nc3ccc4c(ccn4C4CCNC4)c3)nc2n(C2CCCC2)c1=O] | 471.57 |
| 10 | 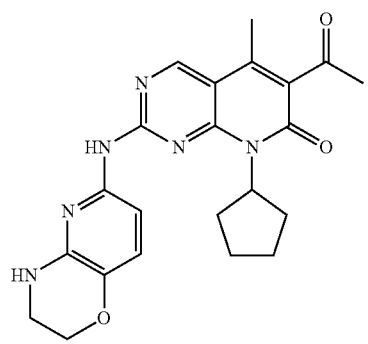 [SMILES: CC(=O)c1c(C)c2cnc(Nc3ccc4c(n3)NCCO4)nc2n(C2CCCC2)c1=O] | 421.46 |
| 11 | 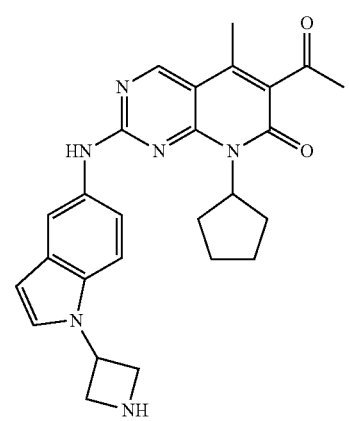 [SMILES: CC(=O)c1c(C)c2cnc(Nc3ccc4c(ccn4C4CNC4)c3)nc2n(C2CCCC2)c1=O] | 457.54 |
| 12 | | 531.66 |
| 13 | | 485.59 |
| 14 | | 498.59 |

| Example | Structure | MS [M+1]+ |
|---|---|---|
| 15 | 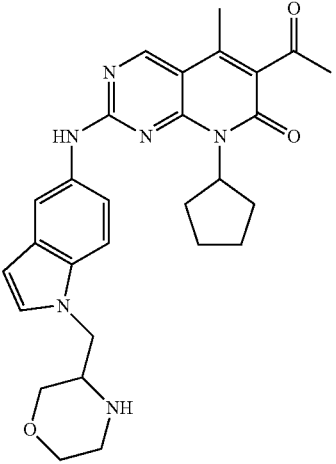 [SMILES: CC(=O)c1c(C)c2cnc(Nc3ccc4c(ccn4CC4COCCN4)c3)nc2n(C2CCCC2)c1=O] | 501.59 |
| 16 | 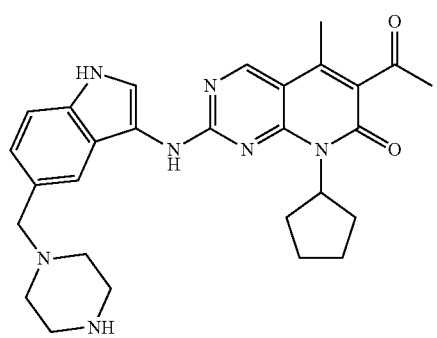 [SMILES: CC(=O)c1c(C)c2cnc(Nc3c[nH]c4ccc(CN5CCNCC5)cc34)nc2n(C2CCCC2)c1=O] | 500.61 |
| 17 | 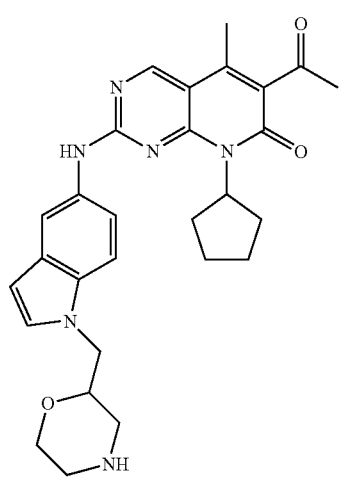 [SMILES: CC(=O)c1c(C)c2cnc(Nc3ccc4c(ccn4CC4CNCCO4)c3)nc2n(C2CCCC2)c1=O] | 501.59 |
| Example | Structure | MS [M+1]+ |
|---|---|---|
| 18 | 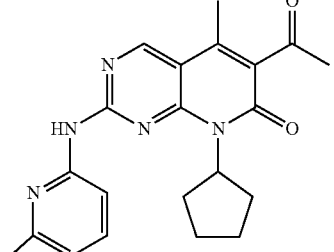 | 502.58 |
| 19 | | 486.58 |
| 20 | | 501.6 |

| Example | Structure | MS [M+1]+ |
|---|---|---|
| 21 | 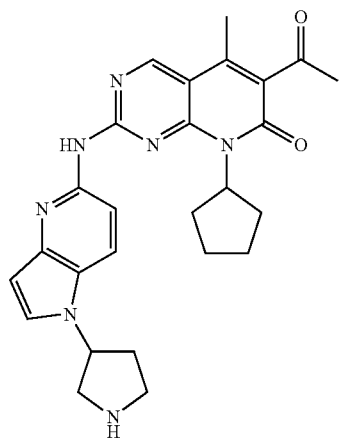 [SMILES: CC(=O)c1c(C)c2cnc(Nc3ccc4c(ccn4C4CCNC4)n3)nc2n(C2CCCC2)c1=O] | 472.55 |
| 22 | 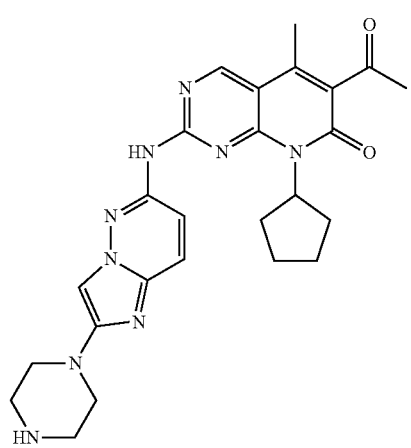 [SMILES: CC(=O)c1c(C)c2cnc(Nc3ccc4nc(N5CCNCC5)cn4n3)nc2n(C2CCCC2)c1=O] | 488.56 |
| 23 | 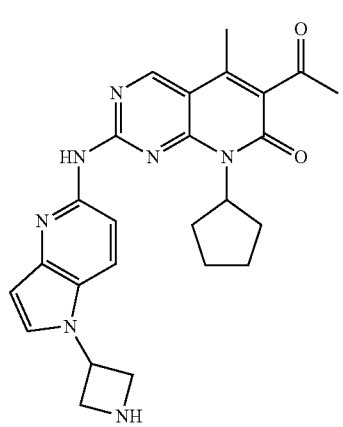 [SMILES: CC(=O)c1c(C)c2cnc(Nc3ccc4c(ccn4C4CNC4)n3)nc2n(C2CCCC2)c1=O] | 458.53 |
| 24 | 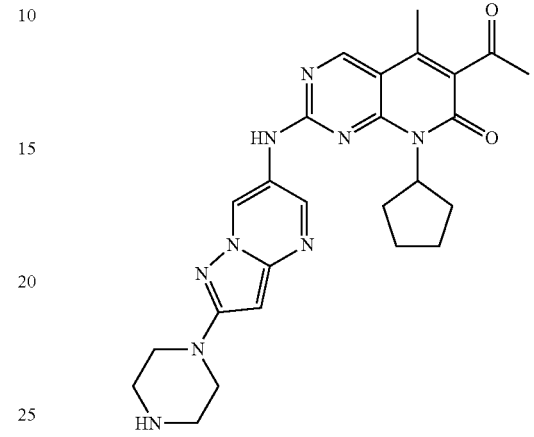 | 488.56 |
| 25 | 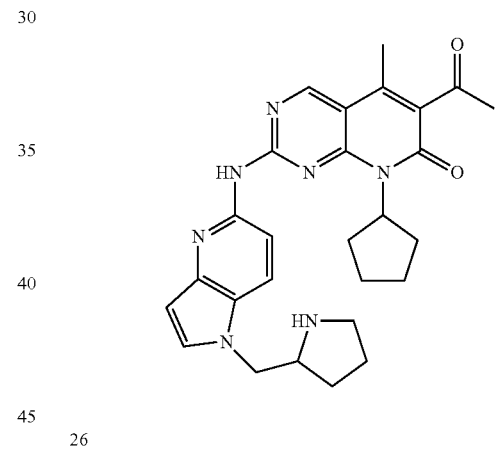 | 486.58 |
| 26 | 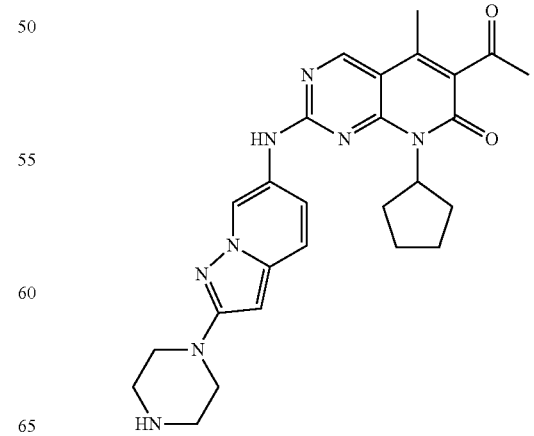 | 487.57 |

| Example | Structure | MS [M+1]+ |
|---|---|---|
| 27 | 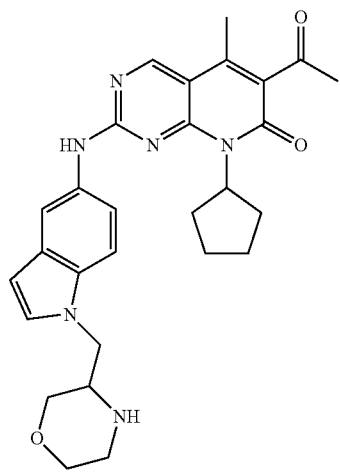 [SMILES: CC(=O)c1c(C)c2cnc(Nc3ccc4c(ccn4CC4COCCN4)c3)nc2n(C2CCCC2)c1=O] | 502.58 |
| 28 | 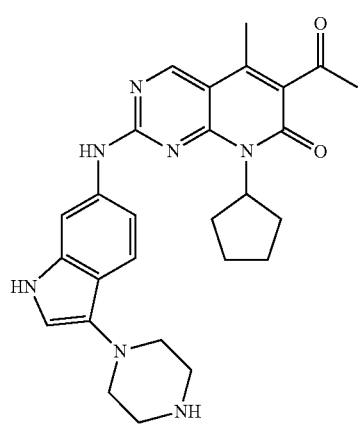 [SMILES: CC(=O)c1c(C)c2cnc(Nc3ccc4c(N5CCNCC5)c[nH]c4c3)nc2n(C2CCCC2)c1=O] | 486.58 |
| 29 | 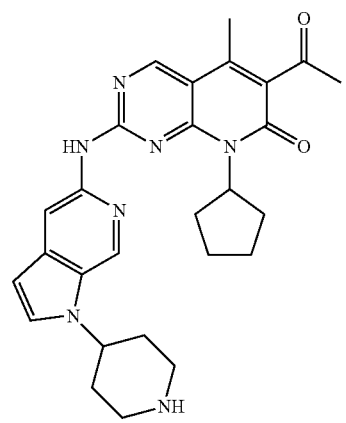 [SMILES: CC(=O)c1c(C)c2cnc(Nc3cc4ccn(C5CCNCC5)c4cn3)nc2n(C2CCCC2)c1=O] | 486.58 |
| 30 | 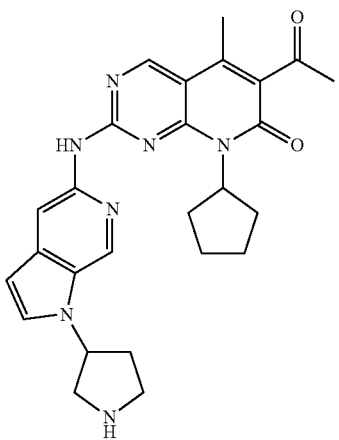 [SMILES: CC(=O)c1c(C)c2cnc(Nc3cc4ccn(C5CCNC5)c4cn3)nc2n(C2CCCC2)c1=O] | 472.55 |
| 31 | 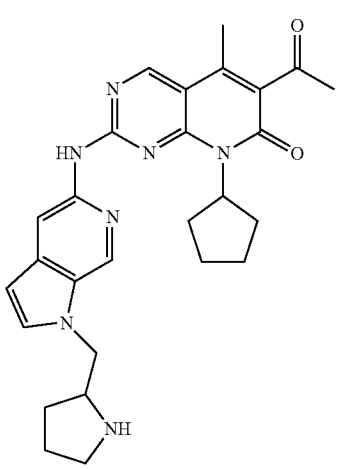 [SMILES: CC(=O)c1c(C)c2cnc(Nc3cc4ccn(CC5CCCN5)c4cn3)nc2n(C2CCCC2)c1=O] | 486.58 |
| 32 | 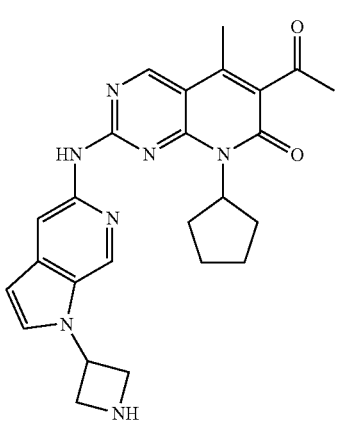 [SMILES: CC(=O)c1c(C)c2cnc(Nc3cc4ccn(C5CNC5)c4cn3)nc2n(C2CCCC2)c1=O] | 458.53 |

-continued
| Example | Structure | MS [M + 1]+ |
|---|---|---|
| 33 | 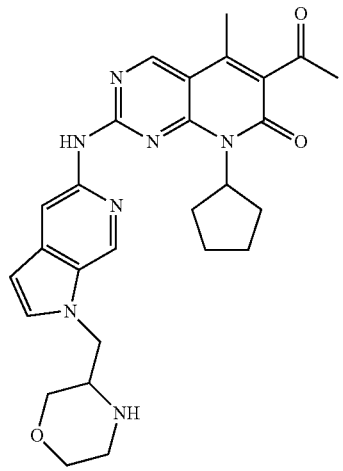 [SMILES: CC(=O)c1c(C)c2cnc(Nc3cc4ccn(CC5COCCN5)c4cn3)nc2n(C2CCCC2)c1=O] | 502.58 |
| 34 | 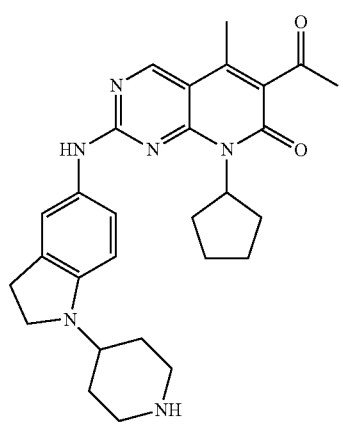 [SMILES: CC(=O)c1c(C)c2cnc(Nc3ccc4c(c3)CCN4C3CCNCC3)nc2n(C2CCCC2)c1=O] | 487.61 |
| 35 | 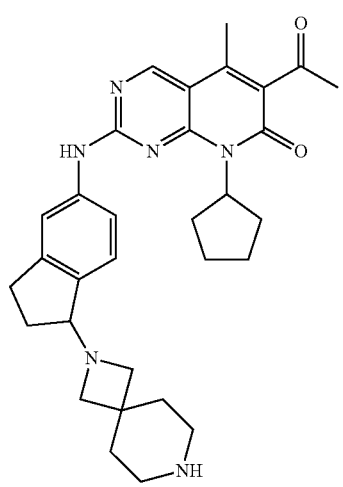 [SMILES: CC(=O)c1c(C)c2cnc(Nc3ccc4c(c3)CCC4N3CC4(CCNCC4)C3)nc2n(C2CCCC2)c1=O] | 527.67 |
-continued
| Example | Structure | MS [M + 1]+ |
|---|---|---|
| 36 | 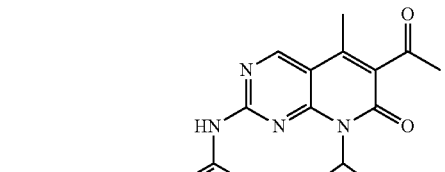 | 500.61 |
| 37 | 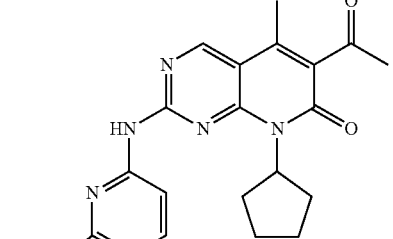 | 488.6 |
| 38 | 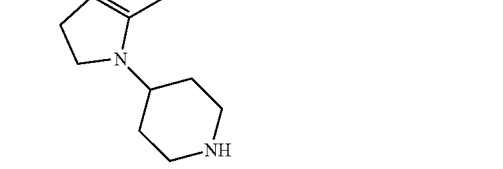 | 499.62 |
Example 39
6-Acetyl-8-cyclopentyl-5-methyl-2-((6-(piperidin-4-yl)-5,6,7,8-tetrahydro-1,6-naphthyridin-2-yl)amino)pyrido[2,3-d]pyrimidin-7(8H)-one)
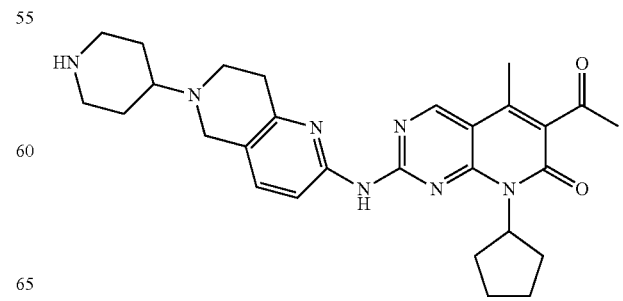

Step 1) tert-butyl 4-(2-((6-acetyl-8-cyclopentyl-5-methyl-7-oxo-7,8-dihydropyrido[2,3-d]pyrimidin-2-yl)amino)-7,8-dihydro-1,6-naphthyridin-6(5H)-yl)piperidine-1-carboxylate)

A mixture of 6-acetyl-8-cyclopentyl-5-methyl-2-((5,6,7,8-tetrahydro-1,6-naphthyridin-2-yl)amino)pyrido[2,3-d]pyrimidin-7(8H)-one (294 mg, 0.70 mmol) and tert-butyl 4-oxopiperidine-1-carboxylate (158 mg, 0.79 mmol) in DMF (20 mL) was stirred for 10 min, and then sodium cyanoborohydride (62.6 mg, 0.86 mmol) was added. The resulting mixture was stirred at rt. The reaction was monitored by LC-MS until the reaction was completed. The reaction mixture was concentrated in vacuo. To the residue was added silica gel, the resulting mixture was purified by silica gel chromatography eluted with DCM/MeOH (V/V)=10/1 to give a yellow solid product (222 mg, 52.5%).

LC-MS: (pos.ion) m/z: 602.6 [M+1]$^+$;

Step 2) 6-acetyl-8-cyclopentyl-5-methyl-2-((6-(piperidin-4-yl)-5,6,7,8-tetrahydro-1,6-naphthyridin-2-yl)amino)pyrido[2,3-d]pyrimidin-7(8H)-one)

To a solution of tert-butyl 4-(2-((6-acetyl-8-cyclopentyl-5-methyl-7-oxo-7,8-dihydropyrido[2,3-d]pyrimidin-2-yl)amino)-7,8-dihydro-1,6-naphthyridin-6(5H)-yl)piperidine-1-carboxylate) (222 mg, 0.37 mmol) in DCM (10 mL) was added TFA (2 mL, 25.8 mmol). The mixture was stirred at rt. After the reaction was completed, the reaction mixture was concentrated in vacuo. The residue was purified by silica gel chromatography eluted with DCM/MeOH (V/V)=20/1 to give a yellow solid product (160 mg, 86.5%).

LC-MS: (pos.ion) m/z: 502.7 [M+1]$^+$; and
$^1$H NMR (400 MHz, CDCl$_3$) δ: 10.16 (s, 1H), 8.86 (s, 1H), 8.27 (s, 1H), 8.14 (d, J=8.4 Hz, 1H), 7.38 (d, J=8.4 Hz, 1H), 5.86-5.84 (m, 1H), 3.78 (s, 2H), 3.11 (d, J=11.2 Hz, 2H), 2.96 (s, 4H), 2.64-2.58 (m, 1H), 2.56 (s, 3H), 2.43 (s, 3H), 2.39 (s, 3H), 2.08 (s, 3H), 1.97 (d, J=11.6 Hz, 2H), 1.92-1.82 (m, 4H), 1.76-1.67 (m, 2H).

Example 40

6-Acetyl-8-cyclopentyl-5-methyl-2-((6-(1-methylpiperidin-4-yl)-5,6,7,8-tetrahydro-1,6-naphthyridin-2-yl)amino)pyrido[2,3-d]pyrimidin-7(8H)-one

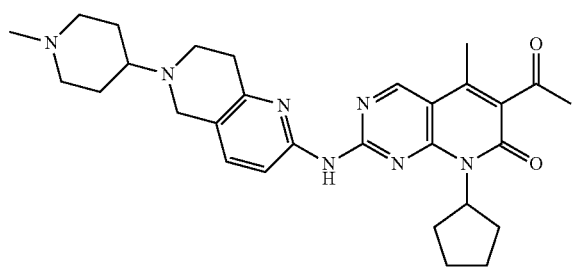 [SMILES: CC(=O)c1c(C)c2cnc(Nc3ccc4c(n3)CCN(C3CCN(C)CC3)C4)nc2n(C2CCCC2)c1=O]

A mixture of 6-acetyl-8-cyclopentyl-5-methyl-2-((6-(piperidin-4-yl)-5,6,7,8-tetrahydro-1,6-naphthyridin-2-yl)amino)pyrido[2,3-d]pyrimidin-7(8H)-one) (98 mg, 0.20 mmol) and formaldehyde (25 mg, 0.31 mmol) in DMF (20 mL) was stirred for 10 min, and then sodium triacetoxyborohydride (53 mg, 0.24 mmol) was added. The resulting mixture was stirred at rt. After the reaction was completed, the reaction mixture was concentrated in vacuo. The residue was purified by silica gel chromatography eluted with DCM/MeOH (V/V)=10/1 to give a yellow solid product (52.6 g, 52%).

LC-MS: (pos.ion) m/z: 516.7 [M+1]$^+$; and
$^1$H NMR (400 MHz, CDCl$_3$) δ 8.87 (s, 1H), 8.29 (s, 1H), 8.10 (d, J=8.4 Hz, 1H), 7.41 (d, J=8.4 Hz, 1H), 5.97-5.78 (m, 1H), 3.78 (s, 2H), 3.12 (d, J=11.2 Hz, 2H), 2.96 (s, 4H), 2.64-2.58 (m, 1H), 2.56 (s, 3H), 2.43 (s, 3H), 2.39 (s, 3H), 2.25 (s, 3H), 2.08 (s, 3H), 1.97 (d, J=11.6 Hz, 2H), 1.92-1.82 (m, 4H), 1.76-1.67 (m, 2H).

Example 41

6-Acetyl-8-cyclopentyl-5-methyl-2-((6-(oxetan-3-yl)-5,6,7,8-tetrahydro-1,6-naphthyridin-2-yl)amino)pyrido[2,3-d]pyrimidin-7(8H)-one

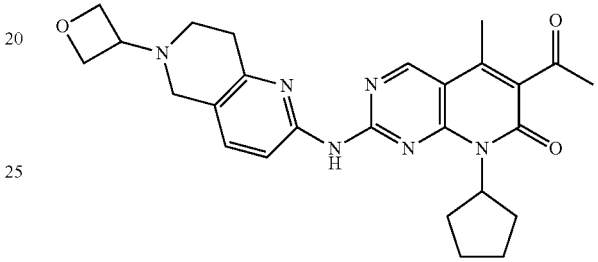

A mixture of 6-acetyl-8-cyclopentyl-5-methyl-2-((5,6,7,8-tetrahydro-1,6-naphthyridin-2-yl)amino)pyrido[2,3-d]pyrimidin-7(8H)-one (109 mg, 0.26 mmol) and oxetan-3-one (25.6 g, 0.36 mmol) in DMF (20 mL) was stirred for 10 min, and then sodium cyanoborohydride (24.1 mg, 0.29 mmol) was added. The resulting mixture was stirred at rt. After the reaction was completed, the reaction mixture was concentrated in vacuo. The residue was purified by silica gel chromatography eluted with DCM/MeOH (V/V)=10/1 to give a yellow solid product (56.5 mg, 45.7%).

LC-MS: (pos.ion) m/z: 475.5 [M+1]$^+$; and
$^1$H NMR (400 MHz, DMSO-d$_6$) δ 10.17 (s, 1H), 8.97 (s, 1H), 7.83 (d, J=8.4 Hz, 1H), 7.51 (d, J=8.4 Hz, 1H), 5.83 (dd, J=17.7, 8.9 Hz, 1H), 4.63 (t, J=6.5 Hz, 2H), 4.54 (t, J=6.1 Hz, 2H), 3.68-3.58 (m, 2H), 3.33 (d, J=13.2 Hz, 1H), 2.85 (t, J=5.6 Hz, 2H), 2.63 (t, J=5.8 Hz, 2H), 2.42 (s, 3H), 2.31 (s, 3H), 2.25 (s, 2H), 1.91 (s, 2H), 1.78 (d, J=8.8 Hz, 2H), 1.59 (d, J=5.0 Hz, 2H).

Example 42

6-Acetyl-8-cyclopentyl-5-methyl-2-((5-oxo-5,6,7,8-tetrahydro-1,6-naphthyridin-2-yl)amino)pyrido[2,3-d]pyrimidin-7(8H)-one

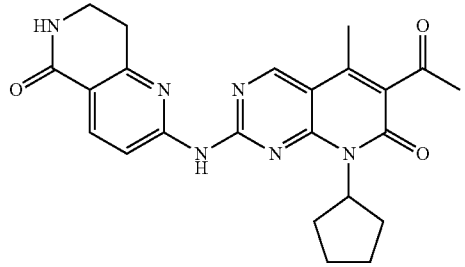 [SMILES: CC(=O)c1c(C)c2cnc(Nc3ccc4c(n3)CCNC4=O)nc2n(C2CCCC2)c1=O]

Step 1) tert-butyl 2-chloro-5-oxo-7,8-dihydro-1,6-naphthyridine-6(5H)-carboxylate To a 100 mL of dry one-neck flask were added tert-butyl 2-chloro-7,8-dihydro-1,6-naphthyridine-6(5H)-carboxylate (500 mg, 1.86 mmol), a solution of ruthenium(III) chloride (100 mg, 0.48 mmol) in tetrachloromethane (16 mL) in turn, and then sodium periodate (1.2 g, 5.6 mmol) was added, the reaction mixture was stirred at rt The reaction was monitored by TLC and LC-MS until the reaction was completed. The reaction mixture was concentrated in vacuo. The residue was diluted with water (100 mL), and extracted with DCM (100 mL×2). The combined organic layers were washed with saturated aqueous NaCl (100 mL×1) and concentrated in vacuo. The residue was purified by silica gel chromatography eluted with DCM/MeOH (V/V)=10/1 to give a yellow solid product (451 mg, 85.73%).

MS-ESI: (ESI, pos.ion) m/z: 283.6 [M+1]$^+$; and $^1$H NMR (400 MHz, CDCl$_3$) δ 8.38 (d, J=8.2 Hz, 1H), 7.37 (d, J=8.3 Hz, 1H), 4.09 (t, J=6.4 Hz, 2H), 3.20 (t, J=6.4 Hz, 2H), 1.60 (s, 9H).

Step 2) tert-butyl 2-((6-acetyl-8-cyclopentyl-5-methyl-7-oxo-7,8-dihydropyrido[2,3-d]pyrimidin-2-yl)amino)-5-oxo-7,8-dihydro-1,6-naphthyridine-6(5H)-carboxylate To a 100 mL of dry one-neck flask were added tert-butyl 2-chloro-5-oxo-7,8-dihydro-1,6-naphthyridine-6(5H)-carboxylate (446 mg, 1.58 mmol), 6-acetyl-2-amino-8-cyclopentyl-5-methylpyrido[2,3-d]pyrimidin-7(8H)-one (455 mg, 1.59 mmol) and 1,4-dioxane (50 mL), and then cesium carbonate (1.76 g, 5.40 mmol), dimethylbisdiphenylphosphinoxanthene (90 mg, 0.15 mmol) and tris(dibenzylideneacetone)dipalladium (150 mg, 0.16 mmol) were added. The mixture was stirred at 110° C. under N$_2$ overnight. After the reaction was completed, stopping heating, the mixture was filtered. The filtrate was concentrated, the residue was purified by silica gel chromatography eluted with DCM/MeOH (V/V)=10/1 to give a light yellow solid product (170 mg, 20.23%).

MS-ESI: (ESI, pos.ion) m/z: 533.4 [M+1]$^+$;

Step 3) 6-acetyl-8-cyclopentyl-5-methyl-2-((5-oxo-5,6,7,8-tetrahydro-1,6-naphthyridin-2-yl)amino)pyrido[2,3-d]pyrimidin-7(8H)-one To a 100 mL of dry one-neck flask was added a solution of tert-butyl 100-((6-acetyl-8-cyclopentyl-5-methyl-7-oxo-7,8-dihydropyrido[2,3-d]pyrimidin-2-yl)amino)-5-oxo-7,8-dihydro-1,6-naphthyridine-6(5H)-carboxylate (350 mg, 0.66 mmol) in DCM (19 mL) and trifluoroacetic acid (4 mL). The mixture was stirred at rt overnight. After the reaction was completed, the mixture was filtered. The filtrate was concentrated. The residue was purified by silica gel chromatography eluted with DCM/MeOH (V/V)=10/1 to give a light yellow solid product (270 mg, 95.0%).

MS-ESI: (ESI, pos.ion) m/z: 433.5 [M+1]$^+$; and $^1$H NMR (600 MHz, DMSO-d$_6$) δ 10.69 (s, 1H), 9.06 (s, 1H), 8.13 (dd, J=34.9, 8.5 Hz, 2H), 7.94 (d, J=17.8 Hz, 1H), 5.91-5.84 (m, 1H), 3.46 (d, J=14.0 Hz, 2H), 2.98 (t, J=6.0 Hz, 2H), 2.89 (s, 2H), 2.44 (s, 3H), 2.34 (s, 3H), 2.26 (s, 2H), 1.96 (s, 2H), 1.82 (s, 2H).

Example 43

6-acetyl-8-cyclopentyl-2-((6-(2-hydroxyethyl)-5,6,7,8-tetrahydro-1,6-naphthyridin-2-yl)amino)-5-methylpyrido[2,3-d]pyrimidin-7(8H)-one

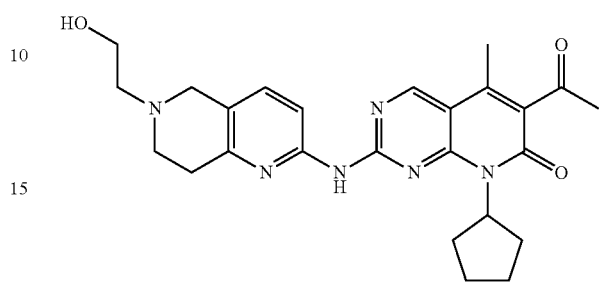

To a solution of 6-acetyl-8-cyclopentyl-5-methyl-2-((5,6,7,8-tetrahydro-1,6-naphthyridin-2-yl)amino)pyrido[2,3-d]pyrimidin-7(8H)-one (213 mg, 0.51 mmol) in N,N-dimethylformamide (15 mL) were added 2-bromoethanol (128 mg, 1.02 mmol) and potassium carbonate (141 mg, 1.02 mmol). The mixture was stirred at rt. After the reaction was completed, the mixture was concentrated in vacuo. To the residue was added silica gel for sample. The sample was purified by silica gel chromatography eluted with DCM/MeOH (V/V)=10/1 to give a yellow solid product (159 mg, 67.4%).

LC-MS: (pos.ion) m/z: 463.5 [M+1]$^+$;

$^1$H NMR (600 MHz, CDCl$_3$) δ 8.85 (s, 1H), 8.13 (d, J=8.2 Hz, 1H), 8.09 (s, 1H), 7.42 (d, J=8.2 Hz, 1H), 5.91-5.84 (m, 1H), 3.77 (s, 2H), 3.72 (s, 2H), 3.00 (d, J=4.6 Hz, 2H), 2.95 (d, J=5.1 Hz, 2H), 2.79 (s, 2H), 2.57 (s, 3H), 2.40 (s, 3H), 2.38-2.34 (m, 2H), 2.09 (s, 2H), 1.90 (s, 2H), 1.71 (s, 2H).

Example 44

6-acetyl-8-cyclopentyl-2-((6-(2-methoxyethyl)-5,6,7,8-tetrahydro-1,6-naphthyridin-2-yl)amino)-5-methylpyrido[2,3-d]pyrimidin-7(8H)-one

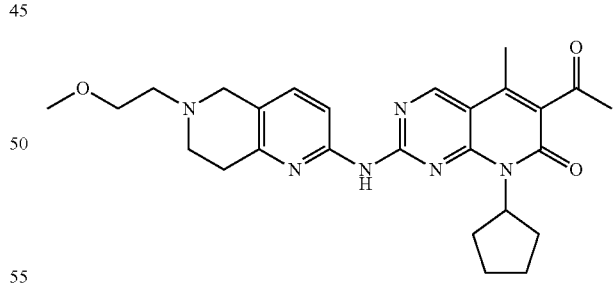

To a solution of 6-acetyl-8-cyclopentyl-5-methyl-2-((5,6,7,8-tetrahydro-1,6-naphthyridin-2-yl)amino)pyrido[2,3-d]pyrimidin-7(8H)-one (271 mg, 0.65 mmol) in N,N-dimethylformamide (15 mL) were added 2-bromoethanol (106 mg, 0.76 mmol) and potassium carbonate (209 mg, 1.51 mmol). The mixture was stirred at rt. After the reaction was completed, the mixture was concentrated in vacuo. To the residue was added silica gel for sample. The sample was purified by silica gel chromatography eluted with DCM/MeOH (V/V)=10/1 to give a yellow solid product (234 mg, 75.6%).

LC-MS: (pos.ion) m/z: 477.5 [M+1]$^+$;

$^1$H NMR (600 MHz, CDCl$_3$) δ 8.88 (s, 1H), 8.35 (s, 1H), 8.10 (d, J=8.4 Hz, 1H), 7.41 (d, J=8.4 Hz, 1H), 5.92-5.85 (m, 1H), 3.71 (d, J=8.0 Hz, 2H), 3.64 (t, J=5.4 Hz, 2H), 3.42 (s, 3H), 3.01 (t, J=5.7 Hz, 2H), 2.93 (t, J=5.9 Hz, 2H), 2.82 (t, J=5.4 Hz, 2H), 2.57 (s, 3H), 2.40 (s, 3H), 2.37 (dd, J=13.5, 5.7 Hz, 2H), 2.08 (dt, J=12.7, 5.6 Hz, 2H), 1.90 (dd, J=12.7, 7.4 Hz, 2H), 1.71 (dd, J=10.7, 5.5 Hz, 2H).

Detection of Anti-Tumor Activity In Vitro of the Compound of the Invention

Biologic Example 1 Enzymatic Inhibitory Activity In Vitro of the Compound of the Invention Test Method The materials are used in the following assay:

HEPES: 4-(2-Hydroxyethyl)piperazine-1-ethanesulfonic acid; Brij-35: Polyethylene Glycol Monoisotridecyl Ether; DTT: Dithiothreitol; EDTA: Ethylene Diamine Tetraacetic Acid; CDK4/CycD3: Cyclin dependent kinase 4; CDK6/CycD3: Cyclin dependent kinase 6; Peptide FAM-P22: fluorescein-labeled peptide 22; ATP: adenosine triphosphate; DMSO: dimethyl sulfoxide; Staurosporine; Coating Reagent #3;

1. Preparation of 1× Kinase Base Buffer and Stop Buffer:

(1) 1× Kinase buffer without MnCl$_2$ (50 mM HEPES, pH 7.5, 0.0015% Brij-35, 10 mM MgCl$_2$, 2 mM DTT); (2) Stop buffer (100 mM HEPES, pH 7.5, 0.015% Brij-35, 0.2% Coating Reagent #3, 50 mM EDTA).

2. Prepare Compound (1) The compound was diluted to 50× of the final desired highest inhibitor concentration in reaction by 100% DMSO. Transferring 100 µL of this compound dilution to a well in a 96-well plate. (2) The compound was diluted by transferring 20 µL of the compound dilution to 60 µL of 100% DMSO in the next well and so forth for a total of 10 concentrations. (3) 100 µL of 100% DMSO was added to two empty wells for no compound control and no enzyme control. (4) Intermediate plate was prepared by transferring 10 µL of compound from source plate to a new 96-well plate and adding 90 µL of 1× kinase buffer to each well of the intermediate plate. The compounds in intermediate plate were mixed for 10 min on shaker. (5) Assay plate was prepared by transferring 5 µL of each well from the 96-well intermediate plate to a 384-well plate in duplicates.

3. Kinase Reaction (1) 2.5× Enzyme solution was prepared by adding kinase in 1× kinase base buffer. (2) 2.5× Peptide solution was prepared by adding FAM-labeled peptide and ATP in the 1× kinase base buffer. (3) 2.5× Enzyme solution was transferred to the assay plate contained 5 µL of compound in 10% DMSO, which was incubated at room temperature for 10 min. (4) 10 µL of 2.5× enzyme solution was added to each well of the 384-well assay plate. (5) Kinase reaction and stopping, after incubating at 28° C. for specified period of time, 25 µL of stop buffer was added to stop reaction.

4. Caliper Reading, Collect Data on Caliper.

5. Curve Fitting (1) Copying conversion data from Caliper program; (2) Converting conversion values to inhibition values: Percent inhibition=(max−conversion)/(max−min)*100; "max" means the value of control without compound; "min" means the value of control without enzyme; (3) Fitting the data in XLfit to obtain IC$_{50}$ values.

Results:

TABLE 2

Enzymatic inhibitory activity in vitro of the compound of the invention

| Example No. | Enzymatic inhibitory activity IC$_{50}$ (nM) | |
| --- | --- | --- |
| | CDK4 | CDK6 |
| 1 | 6.8 | 29.2 |
| 2 | 2392 | 4813 |
| 3 | 5.7 | 47 |
| 4 | 17 | 62 |
| 5 | 25 | 1064 |
| 6 | 20 | 65 |
| 7 | 19 | 83 |
| 39 | 14 | 51 |
| 40 | 7.2 | 25 |
| 41 | 18 | 59 |

Conclusion: The results listed in Table 2 indicated that the most compounds disclosed herein showed high inhibitory activity on CDK4 and CDK6, enzymatic inhibitory activity in vitro thereof are less than 10 µm.

Biologic Example 2 Pharmacokinetic Activity the Compound of the Invention in Rats Test Method The assay agents and samples are as shown below:

Propranolol: Propranolol (internal standard); MTBE: Methyl Tertiary Butyl Ether; Cremophor EL: polyoxyethylated castor oil; KolliphorHS 15: polyethylene glycol 12-hydroxystearate; DMSO: dimethylsulfoxide; PEG400: polyethylene glycol 400; 18 male SD rats.

1. Sample Preparation

Each test compound prepared was completely dissolved in a mixture of 5% DMSO+10% KolliphorHS 15+35% Saline or 5% DMSO+60% PEG400+35% Saline according solubility property thereof.

2. Animal Experiment

Grouping male SD rats weighing 190-250 g randomly to two groups; one group was administered with test compound at a dose of 1.0 mg/kg by intravenous injection, the other group was administered with test compound at a dose of 5.0 mg/kg by oral. After administering, blood samples of intravenous injection group were collected at time points of 0.0833, 0.25, 0.5, 1, 2, 5, 7 and 24 h from caudal vein; blood samples of oral group were collected at time points of 0.25, 0.5, 1, 2, 5, 7 and 24 h from caudal vein. Standard curve was plotted based on concentrations of the samples in a suitable range, the concentrations of test compounds in plasma samples were determined by using LC-MS/MS. Pharmacokinetic parameters were calculated according to drug concentration-time curve using a noncompartmental method by WinNonLin 6.3 software.

3. Results

TABLE 3

Pharmacokinetic acivities of the compound of the invention in rats

| Example | Drug-delivery way | T$_{1/2}$ (h) | T$_{max}$ (h) | C$_{max}$ (ng/ml) | AUC$_{last}$ (h * ng/ml) | AUC$_{INF}$ (h * ng/ml) | F (%) |
| --- | --- | --- | --- | --- | --- | --- | --- |
| 3 | iv | 2.93 | 0.42 | 141 | 485 | 587 | 101 |
| | po | 3.91 | 4 | 293 | 2930 | 2970 | |

TABLE 3-continued

Pharmacokinetic acivities of the compound of the invention in rats

| Example | Drug-delivery way | $T_{1/2}$ (h) | $T_{max}$ (h) | $C_{max}$ (ng/ml) | $AUC_{last}$ (h * ng/ml) | $AUC_{INF}$ (h * ng/ml) | F (%) |
|---|---|---|---|---|---|---|---|
| Palbociclib | iv | 2.72 | 0.083 | 143 | 294 | 332 | 79.94 |
|  | po | 4.28 | 2.67 | 156 | 1280 | 1400 |  |

Conclusion: The results demonstrated that the most compounds disclosed herein had a good in vivo metabolism, better absorption and exposure, and a high bioavailability, and which had an obvious advantage in exposure compared to Palbociclib.

Biologic Example 3: In Vivo Pharmacokinetic Activity of the Compound of the Invention in Mice Test Method:

Grouping 18 ICR mice weighing 18-25 g randomly to three groups; each group has 6 mice. 3 mice of every group were administered by intravenous injection and the other 3 mice were administered by gavage with test compound. After administering, blood samples were collected at designed time points. The blood samples were centrifuged to collect plasma samples. After treating the plasma samples, the blood medicinal concentrations were determined by using LC-MS/MS. Pharmacokinetic parameters were calculated using a noncompartmental method by WinNonLin 6.3 software. Results were shown as below:

Conclusion: The results demonstrated that the most compounds disclosed herein had a good in vivo metabolism, better absorption and exposure, and a high bioavailability, and which had an obvious advantage in bioavailability compared to Palbociclib, especially examples 1 to 44.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a geometric isomer, a tautomer, an N-oxide, or a pharmaceutically acceptable salt thereof,

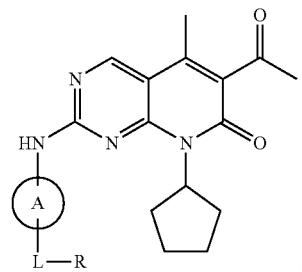

wherein
L is a bond, $-(C(R^{3b})_2)_n-$, $-N(R^1)-(C(R^{3b})_2)_n-$, $-O-(C(R^{3b})_2)_n-$, $-S(=O)_m-$ or $-C(=O)-(C(R^{3b})_2)_n-$;
ring A is

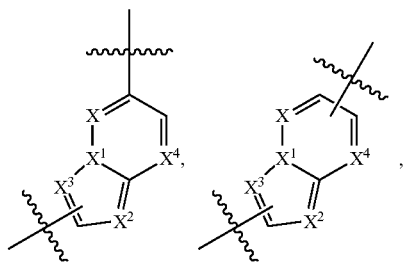

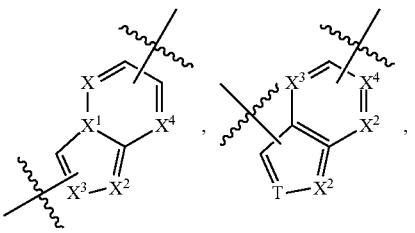

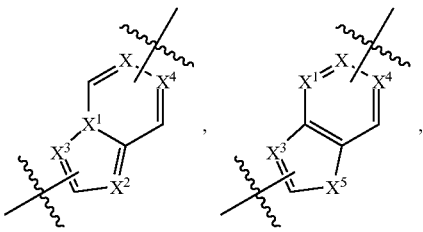

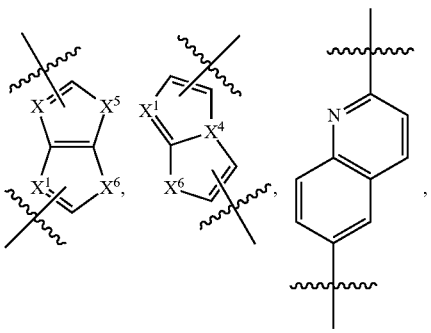

-continued

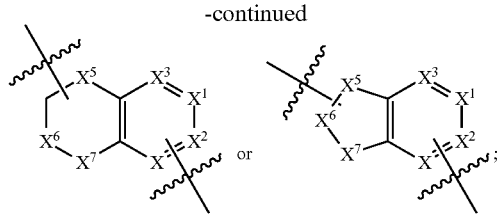

and wherein when ==== is a double bond, T is X,

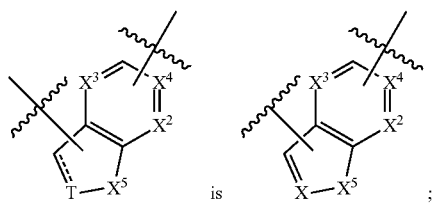

when ==== is a single bond, T is $X^6$,

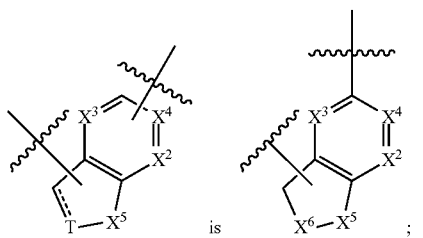

R is H, $R^{13}$, $-(C(R^{3b})_2)_n-N(R^{1a})-C(=O)-(C(R^{3b})_2)_n-R^{13}$ or $-(CH_2)_n-C(=O)-N(R^{1a})-(C(R^{3b})_2)_n-R^{13}$;

$R^{13}$ is H, $C_{3-9}$ cycloalkyl, heteroaryl, heterocyclyl, spiro heterobicyclyl, bridged heterobicyclyl or fused heterobicyclyl;

each $X^7$, $X^5$ and $X^6$ is independently $-C(R^{3a})_2-$, $-N(R^2)-$, $-O-$, $-S(=O)_m-$ or $-C(=O)-$;

each X, $X^1$, $X^2$, $X^3$ and $X^4$ is independently $CR^{3a}$ or N;

each n is independently 0, 1, 2, 3, or 4;

each n1 is independently 1, 2, or 3;

each m is independently 0, 1, or 2;

each $R^{1a}$, $R^1$ and $R^2$ is independently H, $C_{1-4}$ haloalkyl, $H-(C(R^3)_2)_n-O-C(=O)-(C(R^3)_2)_n-$, $(R^4)_2N-(C(R^3)_2)_n-$, $HO-(C(R^3)_2)_n-C(=O)-$, $N(R^4)_2-C(=O)-$, $HO-(C(R^3)_2)_n-$, $H-(C(R^3)_2)_n-O-(C(R^3)_2)_n-$, $H-(C(R^3)_2)_n-SO_2-(C(R^3)_2)_n-$, $H-(C(R^3)_2)_n-C(=O)-(C(R^3)_2)_n-$, $CN-(C(R^3)_2)_n-C(=O)-$, $H-(C(R^3)_2)_n-O-C(=O)-C(=O)-(C(R^3)_2)_n-$, heterocyclyl, heteroaryl, $C_{3-9}$ cycloalkyl or $C_{1-4}$ alkyl;

each $R^{3a}$, $R^{3b}$ and $R^3$ is independently H, F, Cl, Br, $C_{1-4}$ alkyl, hydroxy, carboxy, amino, heterocyclyl, heteroaryl, $C_{3-9}$ cycloalkyl, $C_{1-4}$ haloalkyl, $H-(CH_2)_n-O-(CH_2)_n-$, $N(R^4)_2-C(=O)-$, $H-(CH_2)_n-SO_2-(CH_2)_n-$, $H-O-(CH_2)_n-C(=O)-(CH_2)_n-$, $H-(CH_2)_n-C(=O)-(CH_2)_n-$ or $N(R^4)_2-(CH_2)_n-$;

each $R^4$ is independently H, $C_{1-4}$ alkyl, hydroxy, carboxy, amino, $C_{1-4}$ alkoxy, amino-$C_{1-4}$-alkyl, $NH_2-C(=O)-$, heterocyclyl, heteroaryl, $C_{3-9}$ cycloalkyl, $C_{1-4}$ haloalkyl or $C_{1-4}$ alkylamino;

each moiety represented by A is independently and optionally substituted with one, two, three or four substituents independently selected from H, $C_{1-4}$ alkyl, F, Cl, Br, amino, hydroxy, carboxy, $C_{1-4}$ alkoxy, $C_{1-4}$ haloalkyl, $C_{1-4}$ alkylamino, amino-$C_{1-4}$-alkyl, $H-(C(R^3)_2)_n-O-C(=O)-(C(R^3)_2)_n-$, $(R^4)_2N-(C(R^3)_2)_n-$, $HO-(C(R^3)_2)_n-C(=O)-$, $N(R^4)_2-C(=O)-$, $HO-(C(R^3)_2)_n-$, $H-(C(R^3)_2)_n-O-(C(R^3)_2)_n-$, $H-(C(R^3)_2)_n-SO_2-(C(R^3)_2)_n-$, $H-(C(R^3)_2)_n-C(=O)-(C(R^3)_2)_n-$, $CN-(C(R^3)_2)_n-C(=O)-$, $H-(C(R^3)_2)_n-O-C(=O)-C(=O)-(C(R^3)_2)_n-$, cyano and nitro;

each alkyl, haloalkyl, $H-(C(R^3)_2)_n-O-C(=O)-(C(R^3)_2)_n-$, $N(R^4)_2-C(=O)-$, $H-(C(R^3)_2)_n-SO_2-(C(R^3)_2)_n-$, $-(C(R^3)_2)_n-N(R^4)_2$, $HO-(C(R^3)_2)_n-C(=O)-$, $HO-(C(R^3)_2)_n-$, $H-(C(R^3)_2)_n-O-(C(R^3)_2)_n-$, $H-(C(R^3)_2)_n-C(=O)-(C(R^3)_2)_n-$, $CN-(C(R^3)_2)_n-C(=O)-$, spiro heterobicyclyl, bridged heterobicyclyl, fused heterobicyclyl, heterocyclyl, cycloalkyl, heteroaryl and $H-(C(R^3)_2)_n-O-C(=O)-C(=O)-(C(R^3)_2)_n-$ described in R, $R^1$, $R^{1a}$, $R^2$ and/or $R^{13}$ is optionally and independently substituted with one, two, three or four independent $R^5$;

each $R^5$ is independently H, oxo, $C_{1-6}$ alkyl, F, Cl, Br, amino, hydroxy, carboxy, $C_{1-4}$ alkoxy, $C_{1-4}$ alkylamino, amino-$C_{1-4}$-alkyl, $N(R^4)_2-C(=O)-$, $CN-(C(R^3)_2)_n-C(=O)-$, $C_{1-6}$ haloalkyl, $H-(C(R^3)_2)_n-O-C(=O)-C(=O)-(C(R^3)_2)_n-$, $H-(C(R^3)_2)_n-C(=O)-(C(R^3)_2)_n-$, $H-(C(R^3)_2)_n-SO_2-(C(R^3)_2)_n-$, $H-(C(R^3)_2)_n-O-(C(R^3)_2)_{n1}-C(=O)-(C(R^3)_2)_n-$, $H-(C(R^3)_2)_n-O-C(=O)-(C(R^3)_2)_n-$, $H-(C(R^3)_2)_n-O-(C(R^3)_2)_n-$, cyano, heterocyclyl, $C_{3-9}$ cycloalkyl, heteroaryl or nitro;

each alkyl, alkoxy, alkylamino, aminoalkyl, $N(R^4)_2-C(=O)-$, $CN-(C(R^3)_2)_n-C(=O)-$, haloalkyl, $H-(C(R^3)_2)_n-O-C(=O)-(C(R^3)_2)_n-$, $H-(C(R^3)_2)_n-O-C(=O)-C(=O)-(C(R^3)_2)_n-$, $H-(C(R^3)_2)_n-C(=O)-(C(R^3)_2)_n-$, $H-(C(R^3)_2)_n-SO_2-(C(R^3)_2)_n-$, $H-(C(R^3)_2)_n-O-(C(R^3)_2)_{n1}-C(=O)-(C(R^3)_2)_n-$, $H-(C(R^3)_2)_n-O-(C(R^3)_2)_n-$, heterocyclyl, cycloalkyl and heteroaryl described in $R^5$ is independently and optionally substituted with one, two, three or four independent $R^6$; and each $R^6$ is independently H, oxo, $C_{1-4}$ alkyl, F, Cl, Br, amino, hydroxy, carboxy, $C_{1-4}$ alkoxy, $C_{1-4}$ alkylamino, amino-$C_{1-4}$-alkyl, $N(R^4)_2-C(=O)-$, $CN-(C(R^3)_2)_n-C(=O)-$, $C_{1-4}$ haloalkyl, $H-(C(R^3)_2)_n-O-C(=O)-(C(R^3)_2)_n-$, $H-(C(R^3)_2)_n-O-C(=O)-C(=O)-(C(R^3)_2)_n-$, $H-(C(R^3)_2)_n-C(=O)-(C(R^3)_2)_n-$, $H-(C(R^3)_2)_n-SO_2-(C(R^3)_2)_n-$, $H-(C(R^3)_2)_n-O-(C(R^3)_2)_{n1}-C(=O)-(C(R^3)_2)_n-$, $H-(C(R^3)_2)_n-O-(C(R^3)_2)_n-$, cyano, heterocyclyl, $C_{3-9}$ cycloalkyl, heteroaryl or nitro, wherein each of heteroaryl, heterocyclyl, spiro heterobicyclyl, bridged heterobicyclyl and fused heterobicyclyl has 1-3 ring members independently selected from N, O, P and S, wherein heteroaryl is 5-6 membered monocyclic ring, 7-10 membered bicyclic ring or 10-15 membered tricyclic ring; and wherein heterocyclyl is a saturated or partially unsaturated monocyclic ring having 3-7 ring members or a bicyclic ring having 7-10 ring members.

2. The compound of claim 1 having Formula (II) or Formula (III) or a stereoisomer, a geometric isomer, a tautomer, an N-oxide, or a pharmaceutically acceptable salt thereof,

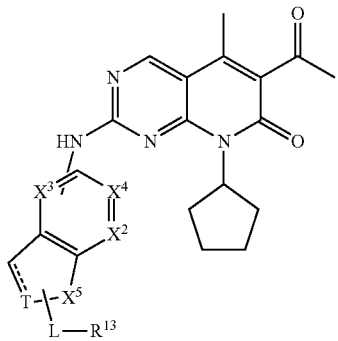

(II)

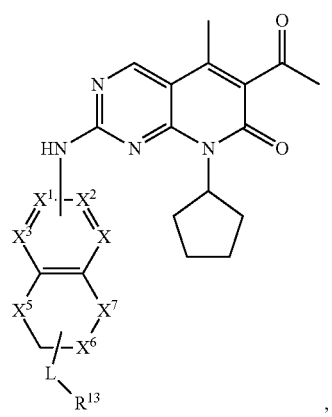

(III)

wherein

L is a bond, —(CH$_2$)$_n$—, —N(R$^1$)—, —O—, —S— or —C(=O)—.

3. The compound of claim 1, wherein R$^{13}$ is H,

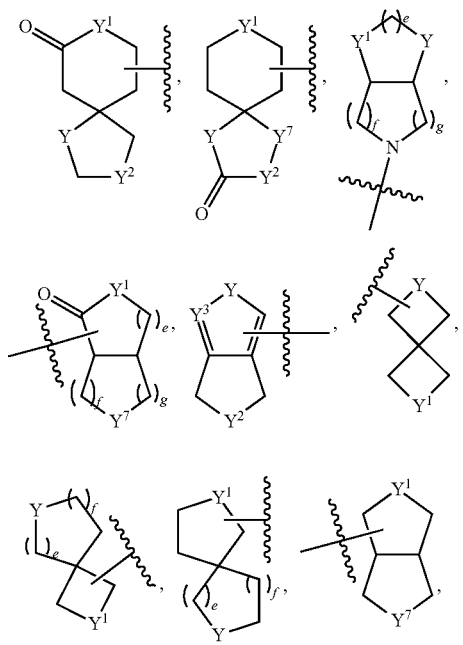

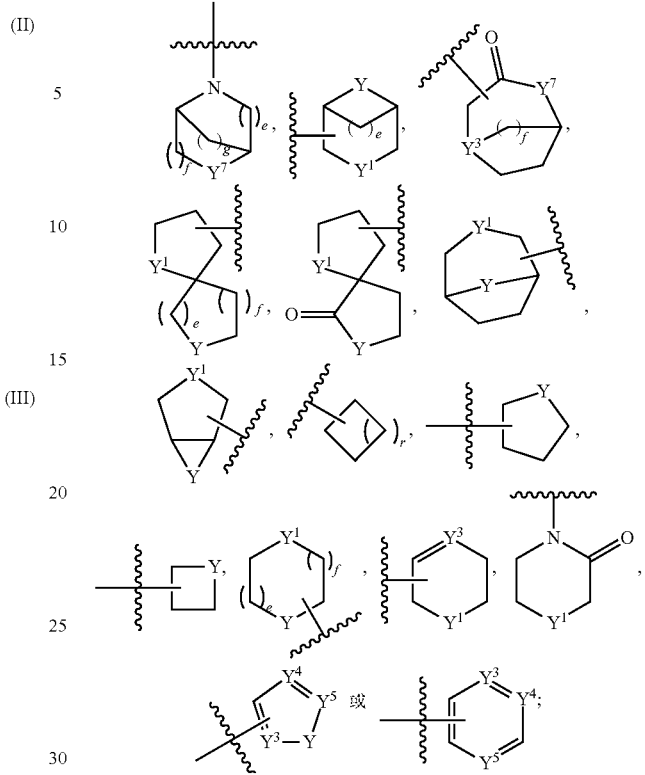

and wherein each Y, Y$^1$, Y$^7$ and Y$^2$ is independently —C(R$^{3c}$)$_2$—, —N(R$^{2b}$)—, —O—, —S(=O)$_m$— or —C(=O)—;

each Y$^3$, Y$^4$ and Y$^5$ is independently CR$^{3c}$ or N; and each R$^{2b}$ is independently H, C$_{1-4}$ haloalkyl, H—(C(R$^3$)$_2$)$_n$—O—C(=O)—(C(R$^3$)$_2$)$_n$—, (R$^4$)$_2$N—(C(R$^3$)$_2$)$_n$—, HO—(C(R$^3$)$_2$)$_n$—C(=O)—, N(R$^4$)$_2$—C(=O)—, HO—(C(R$^3$)$_2$)$_n$—, H—(C(R$^3$)$_2$)$_n$—O—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—C(=O)—(C(R$^3$)$_2$)$_n$—, CN—(C(R$^3$)$_2$)$_n$—C(=O)—, H—(C(R$^3$)$_2$)$_n$—O—C(=O)—C(=O)—(C(R$^3$)$_2$)$_n$— or C$_{1-4}$ alkyl;

each R$^{3c}$ is independently H, F, Cl, Br, C$_{1-4}$ alkyl, hydroxy, carboxy, amino, C$_{1-4}$ haloalkyl, H—(CH$_2$)$_n$—O—(CH$_2$)$_n$—, N(R$^4$)$_2$—C(=O)—, H—(CH$_2$)$_n$—SO$_2$—(CH$_2$)$_n$—, H—O—(CH$_2$)$_n$—C(=O)—(CH$_2$)$_n$—, H—(CH$_2$)$_n$—C(=O)—(CH$_2$)$_n$— or N(R$^4$)$_2$—(CH$_2$)$_n$—;

each e, r, f and g is independently 0, 1, 2, or 3.

4. The compound of claim 1, wherein

R$^{13}$ is cyclopropyl, cyclohexyl, cyclopentyl, cyclobutyl, H,

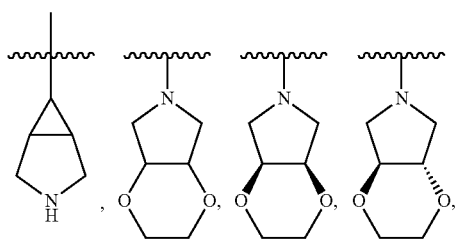

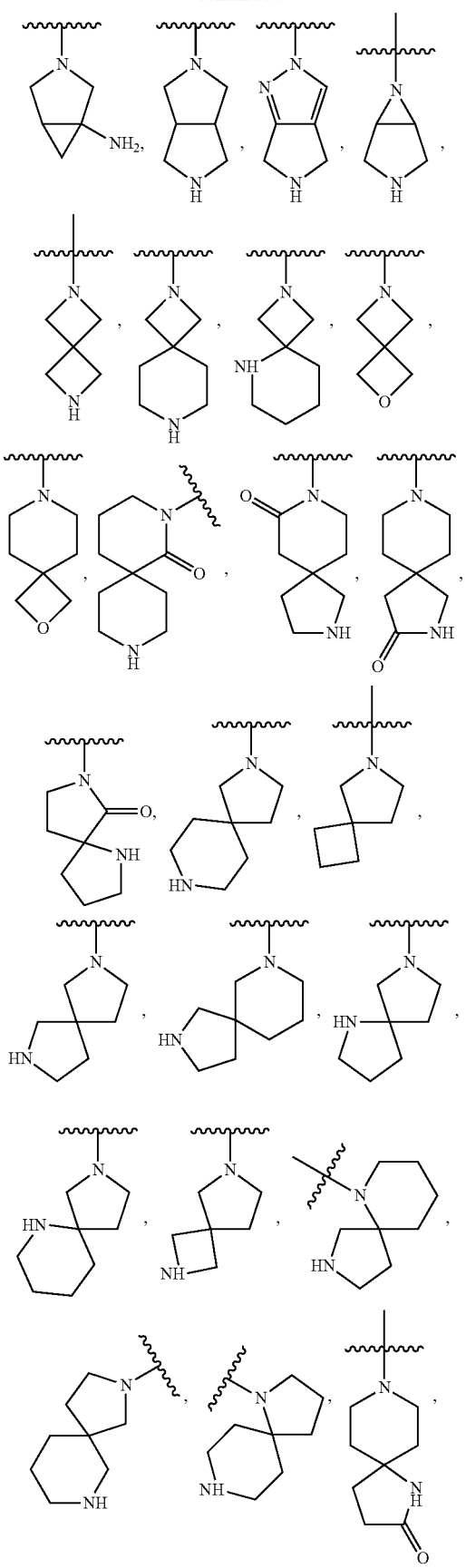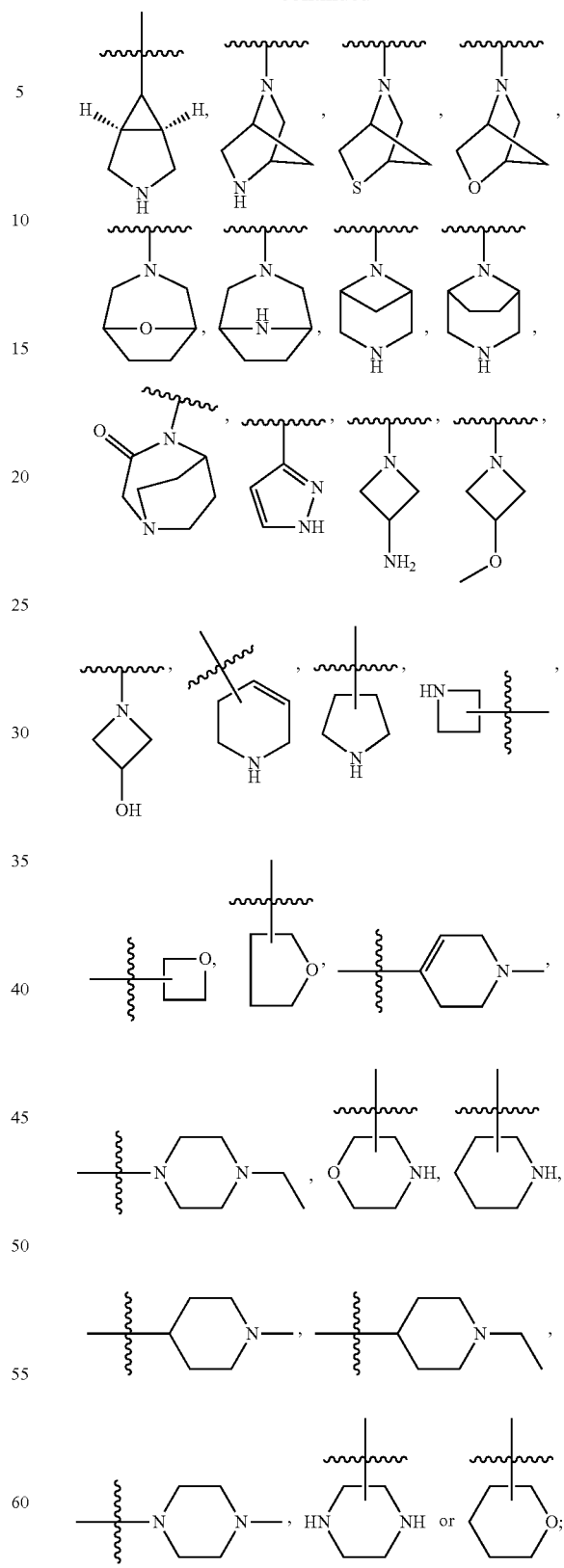
and wherein each moiety represented by $R^{13}$ is independently and optionally substituted with one, two, three or four independent $R^5$.

5. The compound of claim 1, wherein ring A is
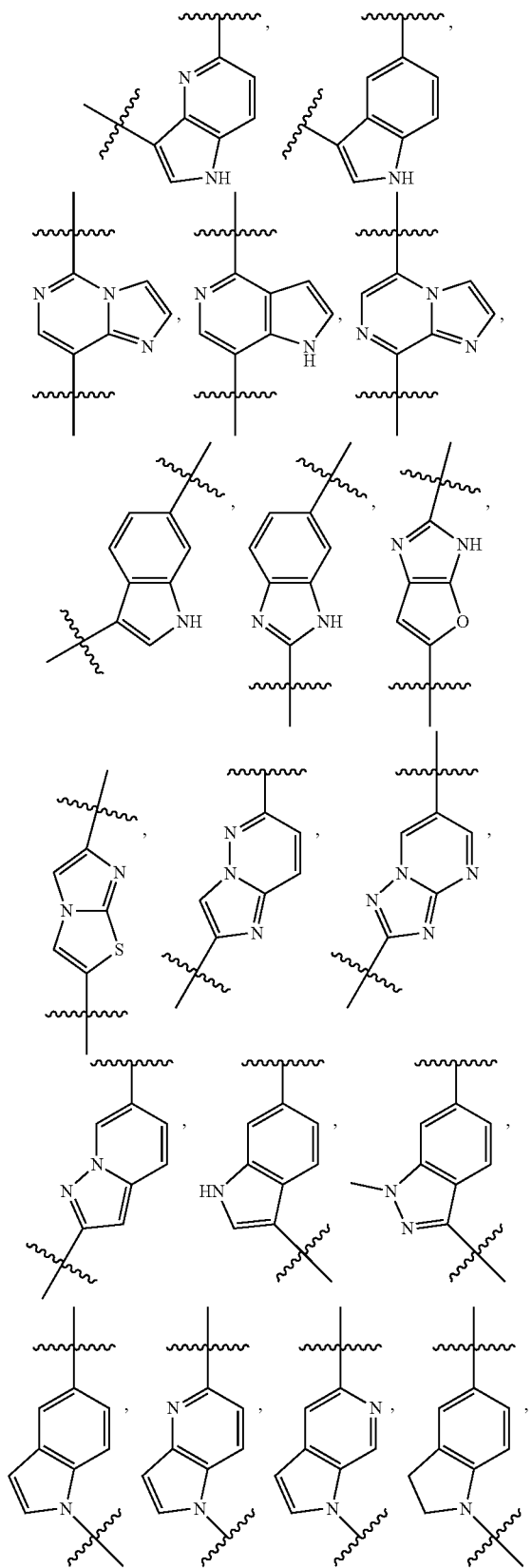
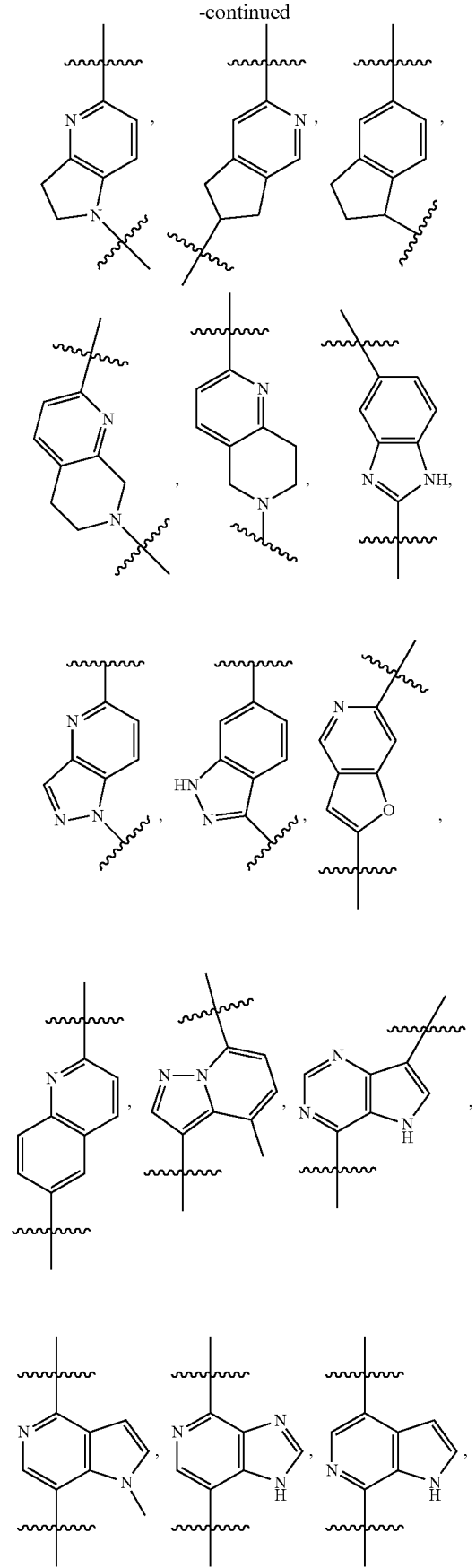

-continued

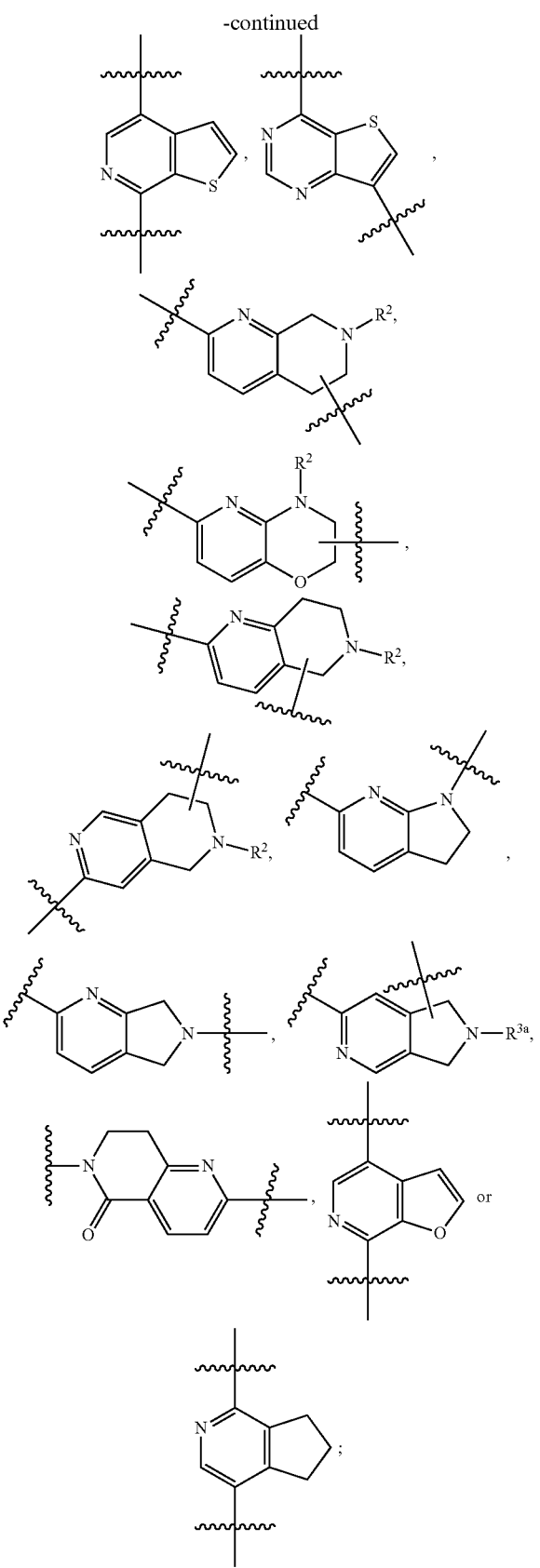

each moiety represented by A is independently and optionally substituted with one, two, three or four substituents independently selected from H, $C_{1-4}$ alkyl, F, Cl, Br, amino, hydroxy, carboxy, $C_{1-4}$ alkoxy, $C_{1-4}$ haloalkyl, $C_{1-4}$ alkylamino, amino-$C_{1-4}$-alkyl, H—(C($R^3$)$_2$)$_n$—O—C(=O)—(C($R^3$)$_2$)$_n$—, ($R^4$)$_2$N—(C($R^3$)$_2$)$_n$—, HO—(C($R^3$)$_2$)$_n$—C(=O)—, N($R^4$)$_2$—C(=O)—, HO—(C($R^3$)$_2$)$_n$—, H—(C($R^3$)$_2$)$_n$—O—(C($R^3$)$_2$)$_n$—, H—(C($R^3$)$_2$)$_n$—SO$_2$—(C($R^3$)$_2$)$_n$—, H—(C($R^3$)$_2$)$_n$—C(=O)—(C($R^3$)$_2$)$_n$—, CN—(C($R^3$)$_2$)$_n$—C(=O)—, H—(C($R^3$)$_2$)$_n$—O—C(=O)—C(=O)—(C($R^3$)$_2$)$_n$—, cyano and nitro.

6. The compound of claim 1, wherein each $R^{3a}$, $R^{3b}$ and $R^3$ is independently H, F, Cl, Br, hydroxy, carboxy, amino, trifluoromethyl, methyl, ethyl, propyl, butyl, cyclopropyl, cyclohexyl, cyclopentyl, H—(CH$_2$)$_n$—O—(CH$_2$)$_n$—, N($R^4$)$_2$—C(=O)—, H—(CH$_2$)$_n$—SO$_2$—(CH$_2$)$_n$—, H—O—(CH$_2$)$_n$—C(=O)—(CH$_2$)$_n$— or N($R^4$)$_2$—(CH$_2$)$_n$—; and each $R^4$ is independently H, hydroxy, carboxy, amino, methoxy, aminomethyl, aminoethyl, NH$_2$—C(=O)—, trifluoromethyl, 2,2-difluoroethyl, methyl, ethyl, propyl or butyl.

7. The compound of claim 1, wherein each $R^{1a}$, $R^1$ and $R^2$ is independently H, 3,3,3-trifluoropropyl, trifluoromethyl, 1,1-difluoroethyl, cyclopropyl, cyclohexyl, cyclopentyl, cyclobutyl, H—(C($R^3$)$_2$)$_n$—O—C(=O)—(C($R^3$)$_2$)$_n$—, ($R^4$)$_2$N—(C($R^3$)$_2$)$_n$—, HO—(C($R^3$)$_2$)$_n$—C(=O)—, N($R^4$)$_2$—C(=O)—, HO—(C($R^3$)$_2$)$_n$—, H—(C($R^3$)$_2$)$_n$—O—(C($R^3$)$_2$)$_n$—, H—(C($R^3$)$_2$)$_n$—SO$_2$—(C($R^3$)$_2$)$_n$—, H—(C($R^3$)$_2$)$_n$—C(=O)—(C($R^3$)$_2$)$_n$—, CN—(C($R^3$)$_2$)$_n$—(C=O)—, H—(C($R^3$)$_2$)$_n$—O—C(=O)—C(=O)—(C($R^3$)$_2$)$_n$—,

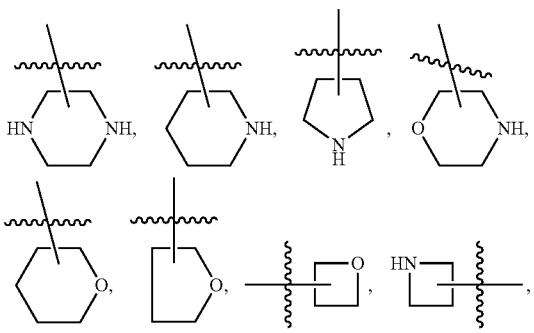

methyl, ethyl, propyl or butyl;

each $R^5$ is independently H, oxo, methyl, ethyl, propyl, butyl, F, Cl, Br, amino, hydroxy, carboxy, methoxy, $C_{1-4}$ alkylamino, amino-$C_{1-4}$-alkyl, N($R^4$)$_2$—C(=O)—, CN—(C($R^3$)$_2$)$_n$—C(=O)—, H—(C($R^3$)$_2$)$_n$—O—C(=O)—(C($R^3$)$_2$)$_n$—,

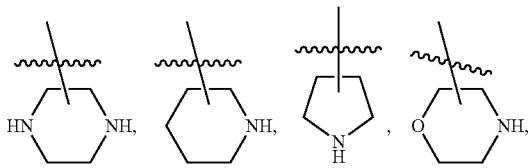

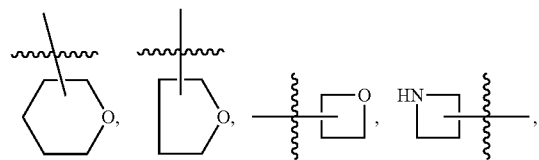

$C_{1-4}$ haloalkyl, H—(C(R$^3$)$_2$)$_n$—O—C(=O)—C(=O)—(C(R$^3$)$_2$)$_n$—, H—(C(R$^3$)$_2$)$_n$—C(=O)—(C(R$^3$)$_2$)$_n$—, H—(C(R$^3$)$_2$)$_n$—O—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—O—(C(R$^3$)$_2$)$_{n1}$—C(=O)—(C(R$^3$)$_2$)$_n$—, cyano, cyclopropyl, cyclohexyl, cyclopentyl or nitro; and each R$^6$ is independently H, oxo, methyl, ethyl, propyl, butyl, F, Cl, Br, amino, hydroxy, carboxy, methoxy, $C_{1-4}$ alkylamino, amino-$C_{1-4}$-alkyl, N(R$^4$)$_2$—C(=O)—, CN—(C(R$^3$)$_2$)$_n$—C(=O)—, $C_{1-4}$ haloalkyl, H—(C(R$^3$)$_2$)$_n$—O—C(=O)—(C(R$^3$)$_2$)$_n$—, H—(C(R$^3$)$_2$)$_n$—O—C(=O)—C(=O)—(C(R$^3$)$_2$)$_n$—, H—(C(R$^3$)$_2$)$_n$—C(=O)—(C(R$^3$)$_2$)$_n$—, H—(C(R$^3$)$_2$)$_n$—SO$_2$—(C(R$^3$)$_2$)$_n$—, H—(C(R$^3$)$_2$)$_n$—O—(C(R$^3$)$_2$)$_{n1}$—C(=O)—(C(R$^3$)$_2$)$_n$—, H—(C(R$^3$)$_2$)$_n$—O—(C(R$^3$)$_2$)$_n$—, cyano, heterocyclyl, $C_{3-6}$ cycloalkyl or nitro.

8. The compound of claim 1 having one of the following structures:

22
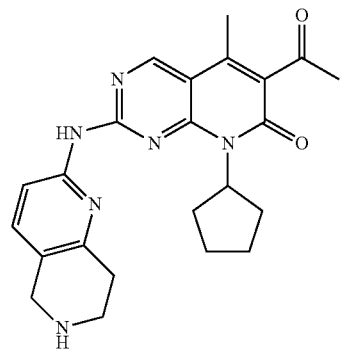

23
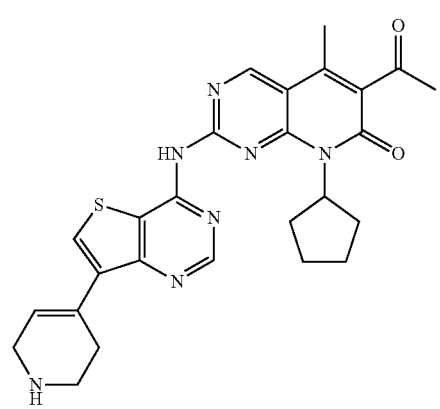

24
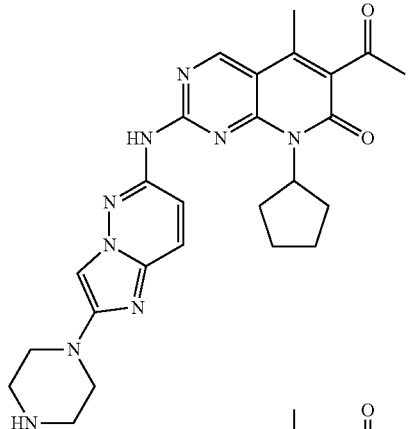

25
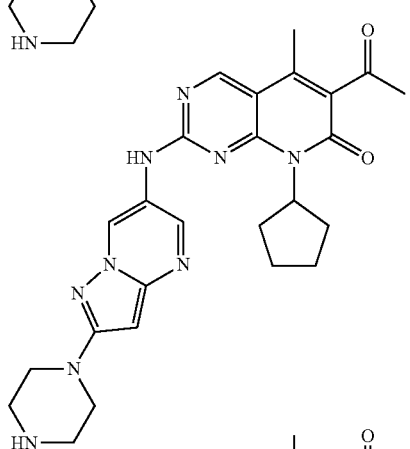

26
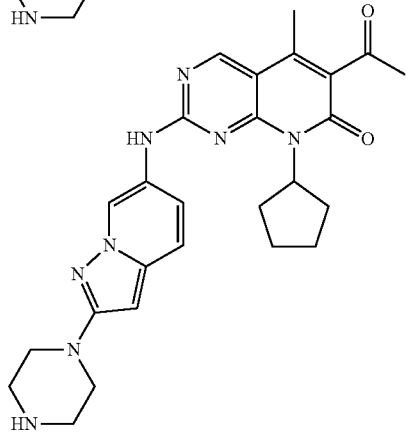

27
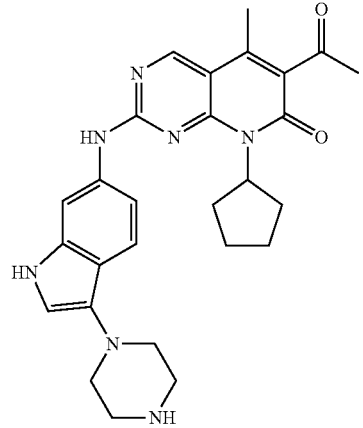

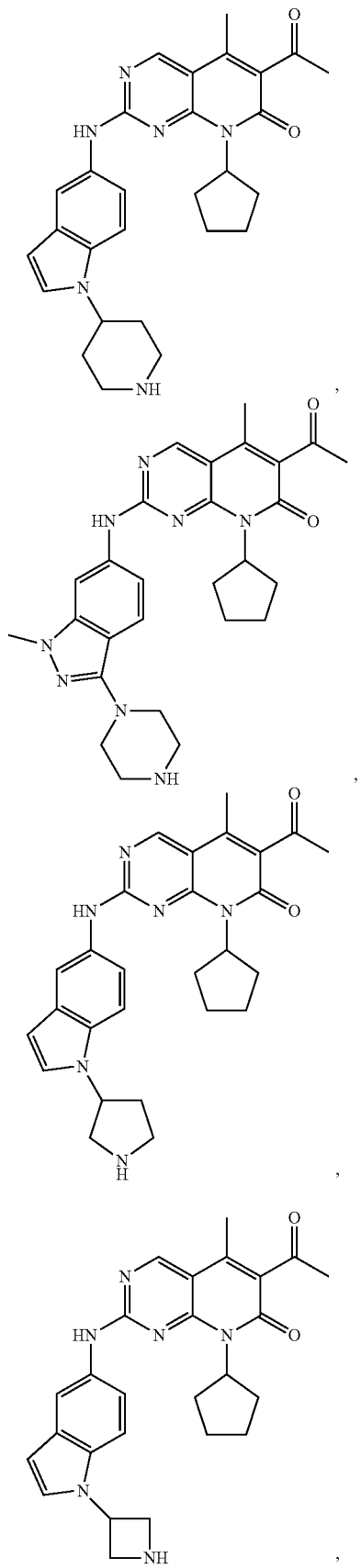
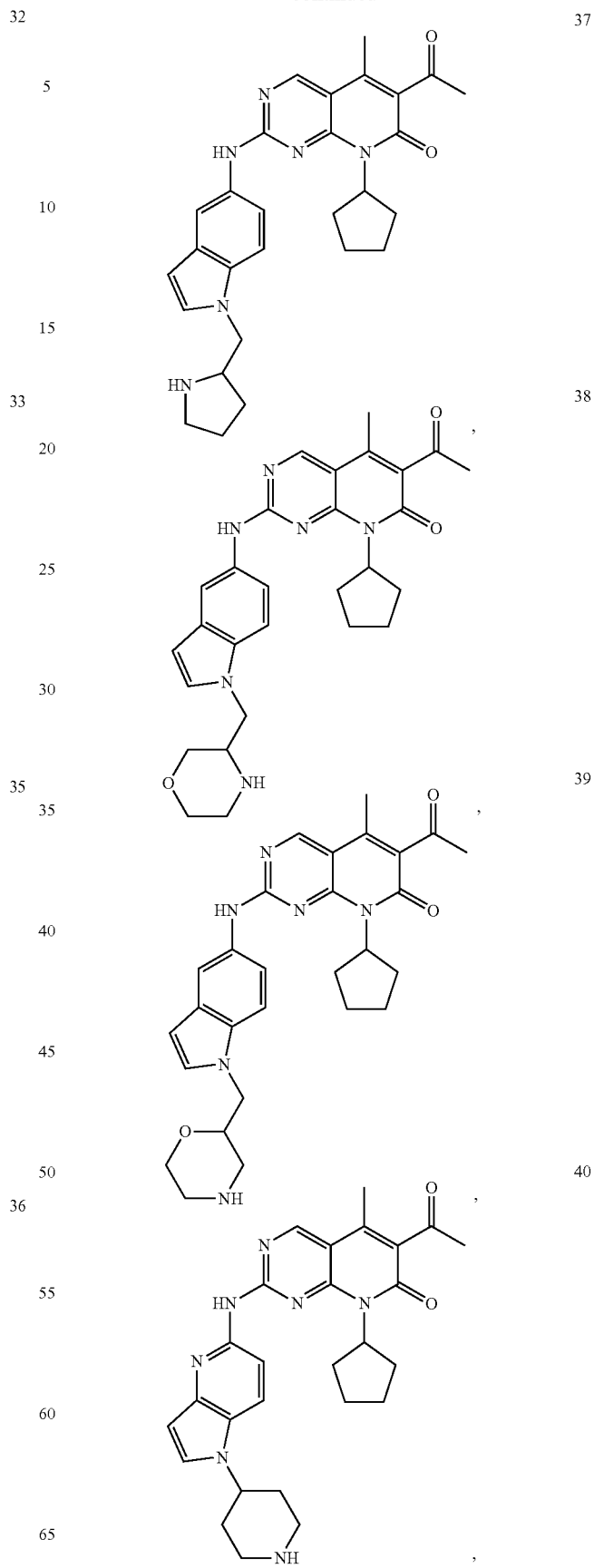

41
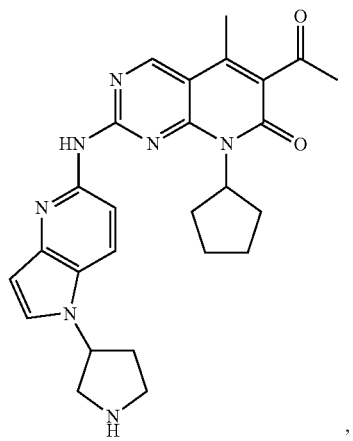
,
42
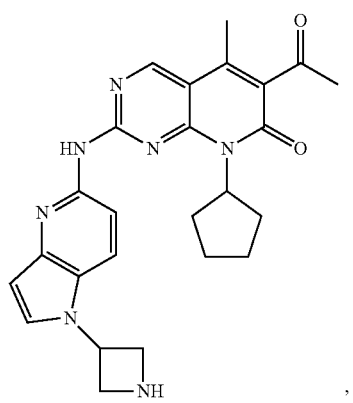
,
43
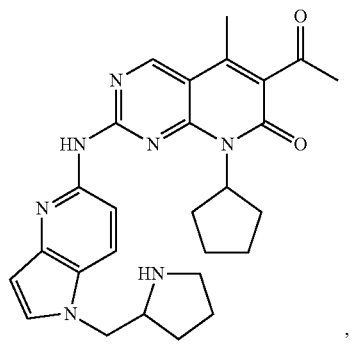
,
44
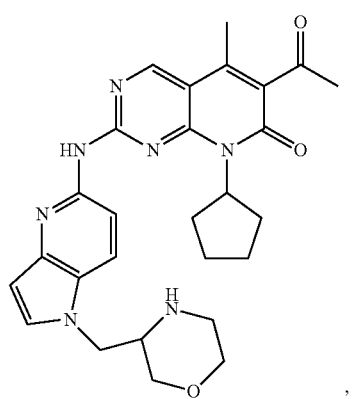
,
45
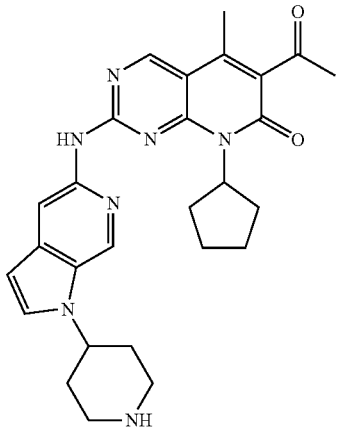
,
46
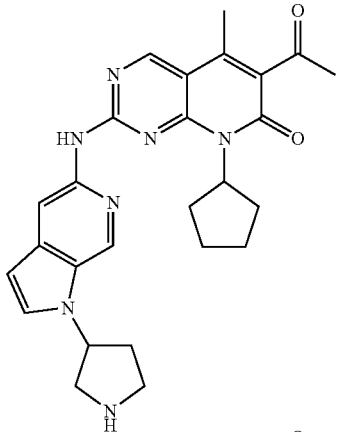
,
47
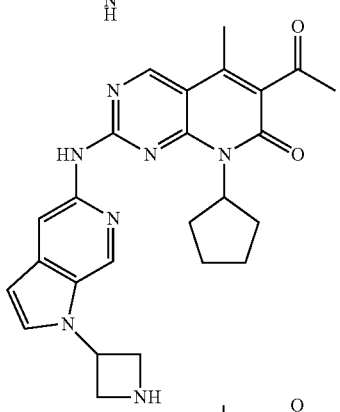
,
48
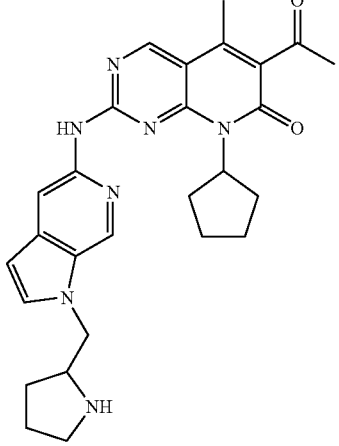
,

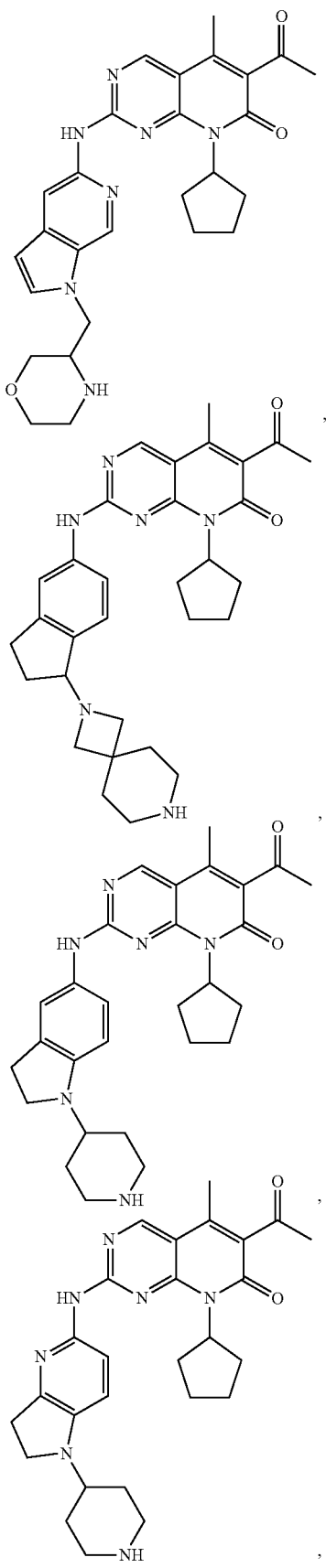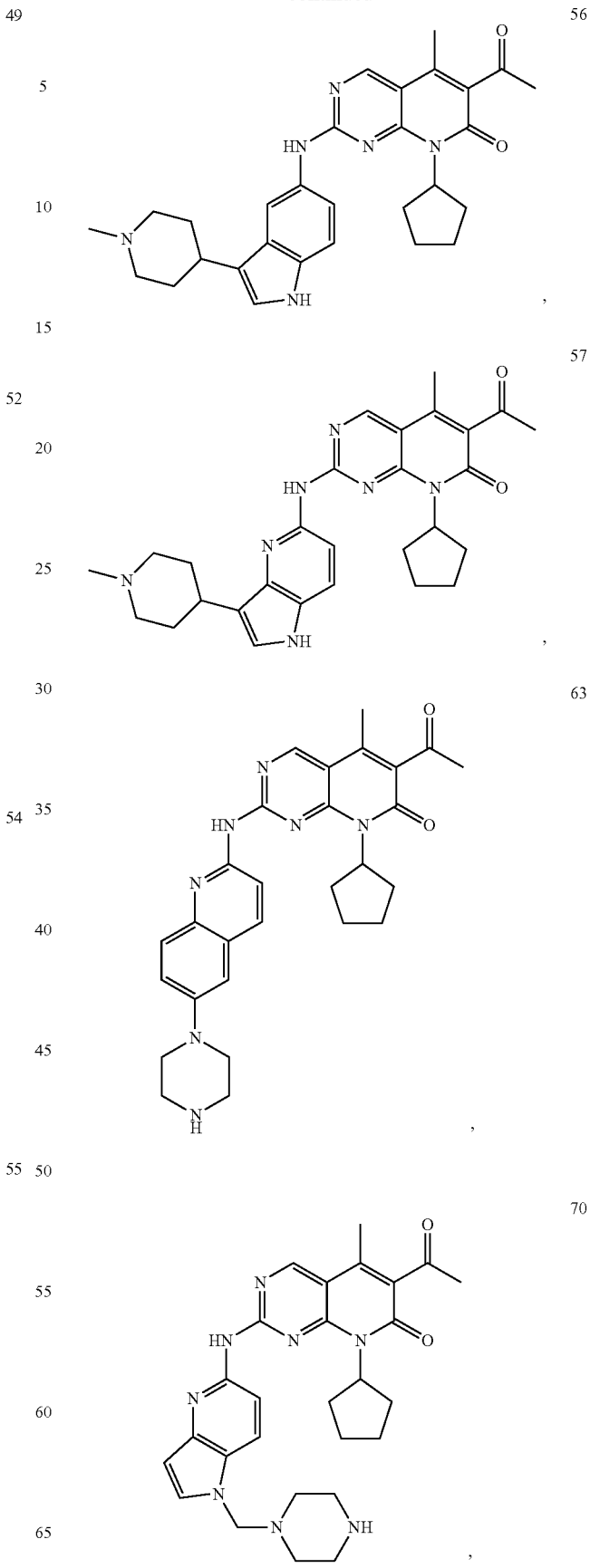

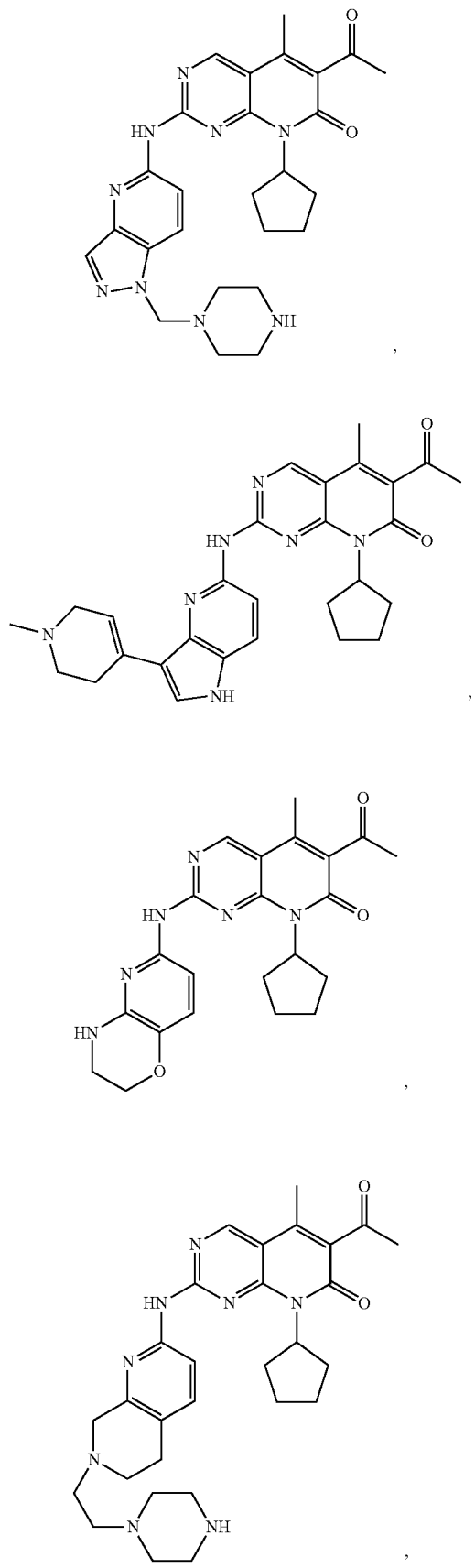
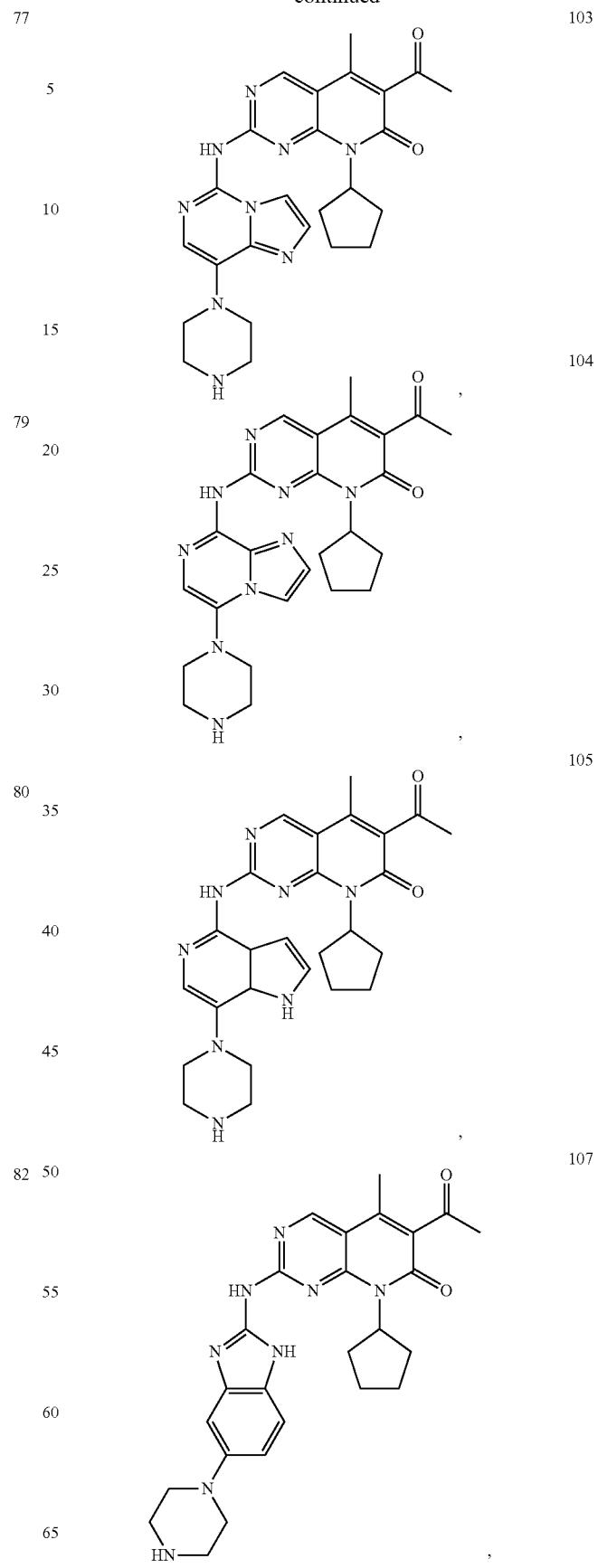

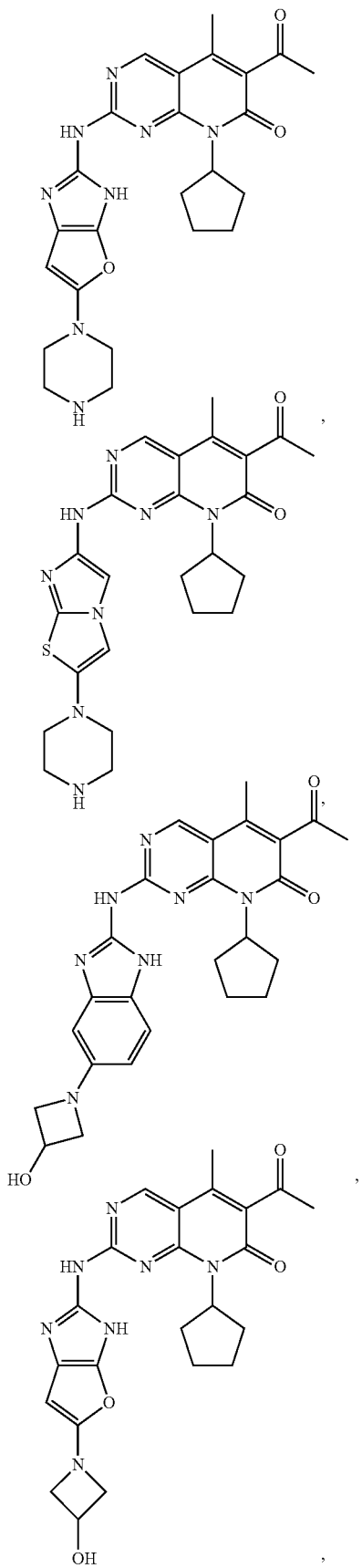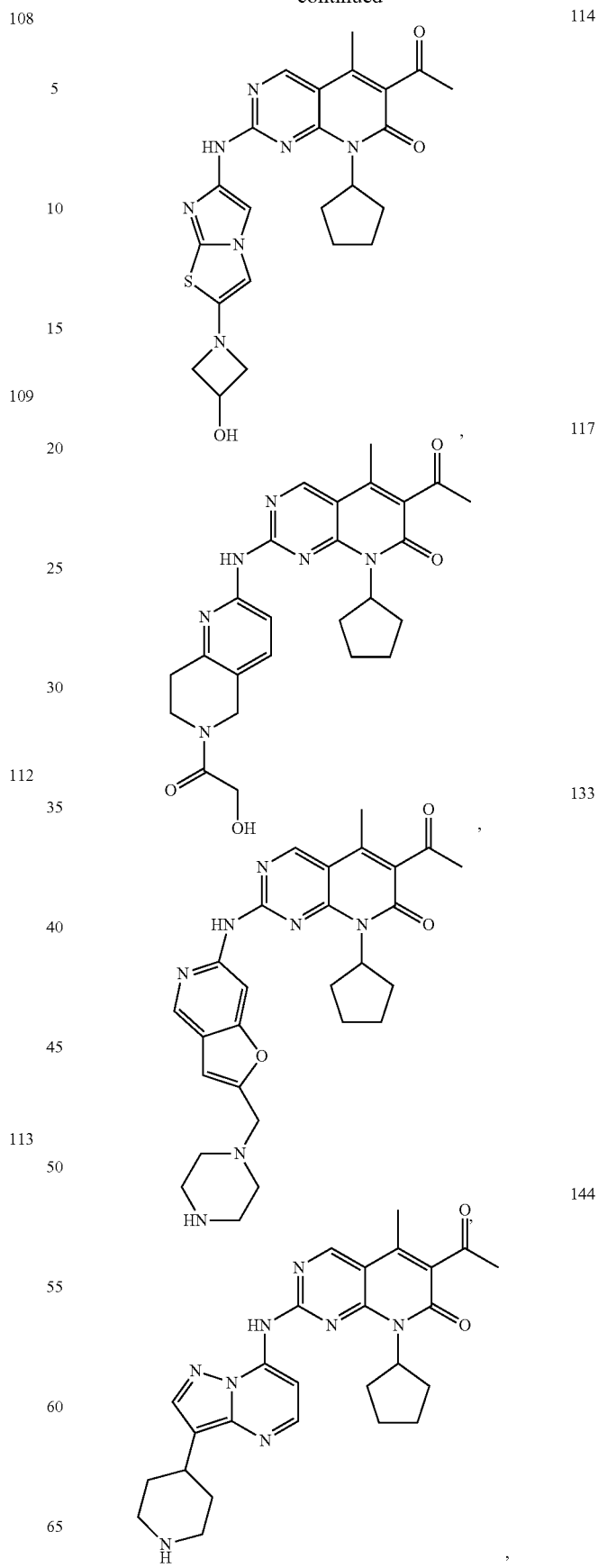

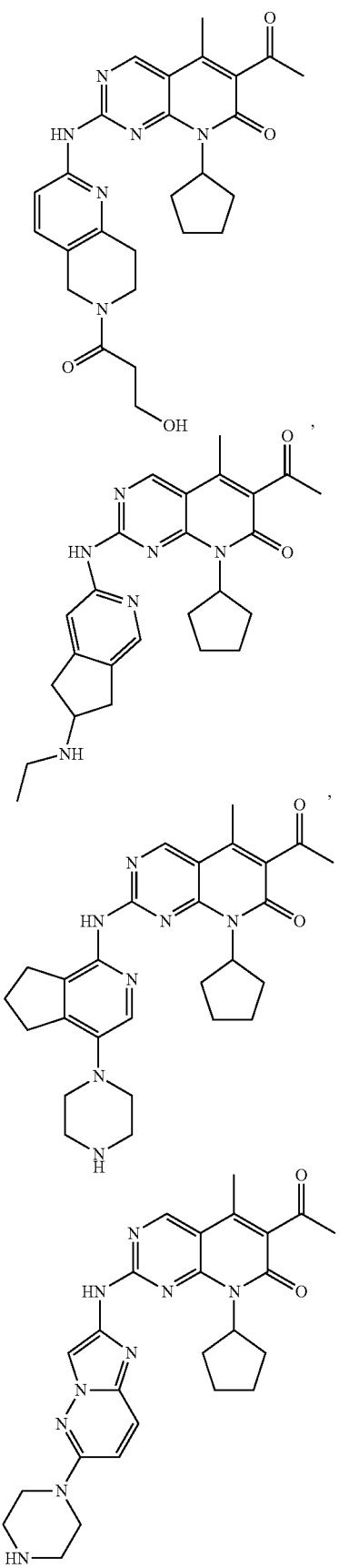
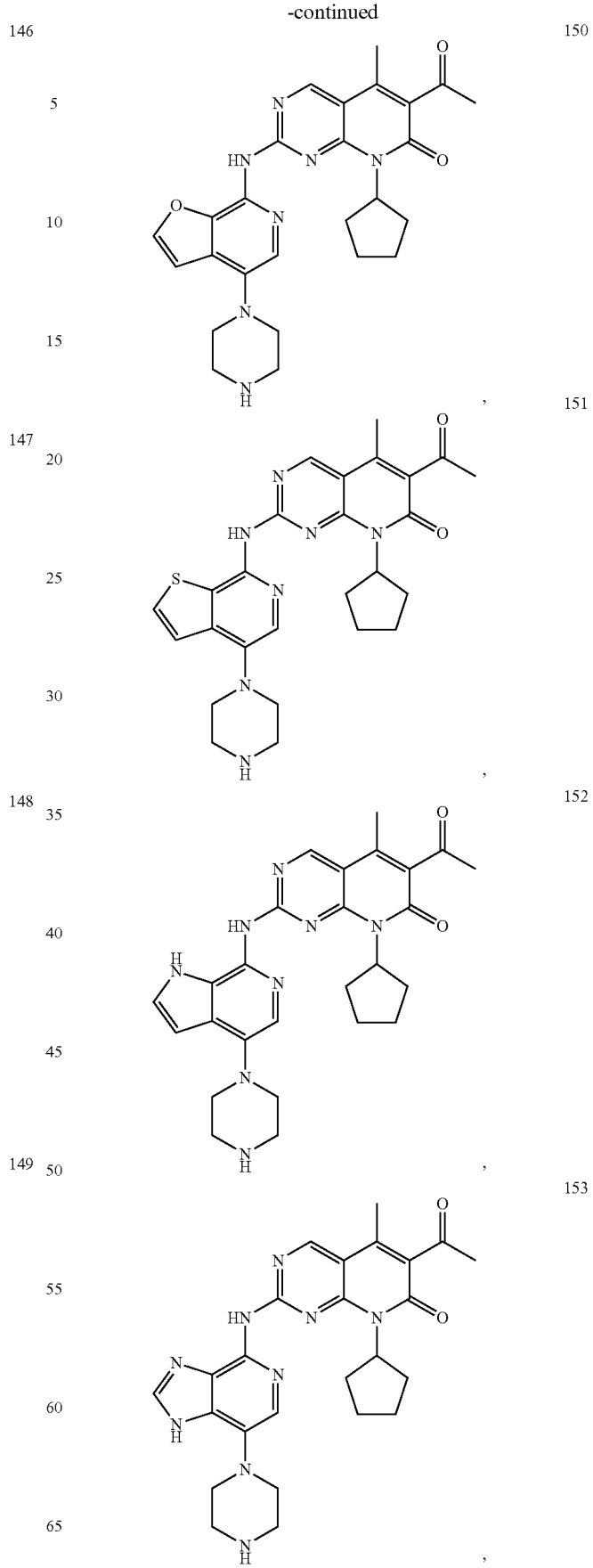

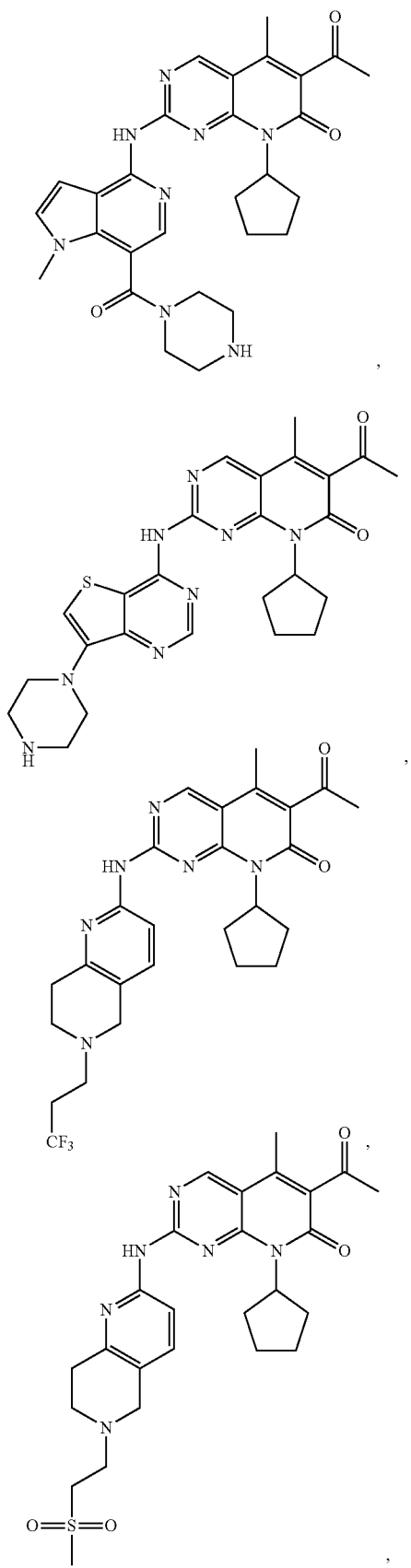
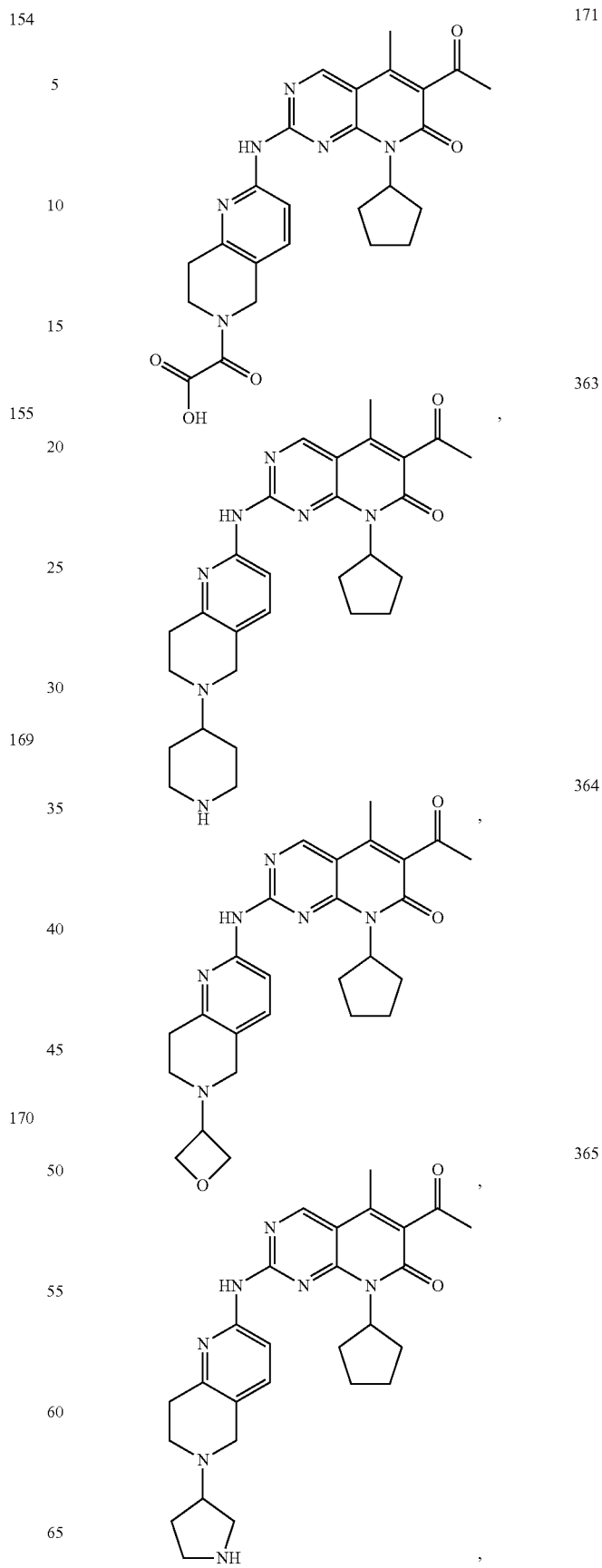

369
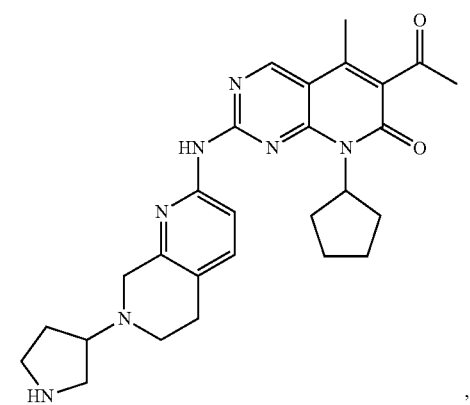
370
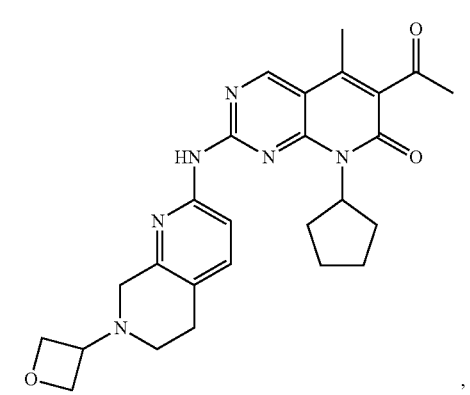
371
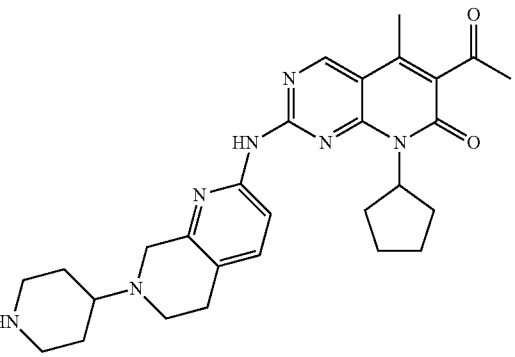
372
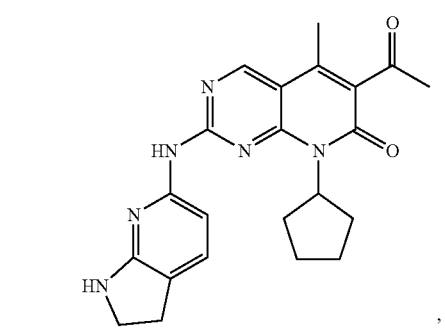
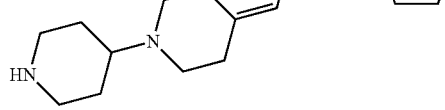
373
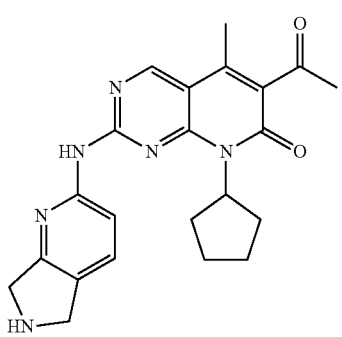
374
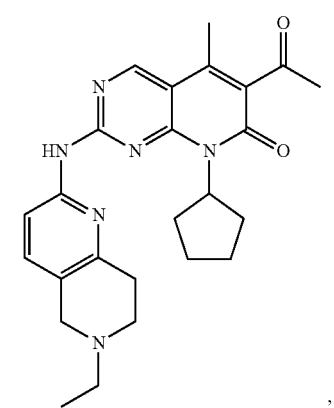
375
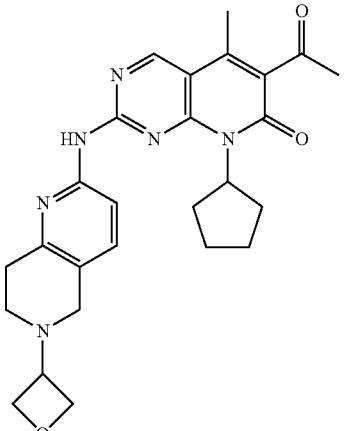
376
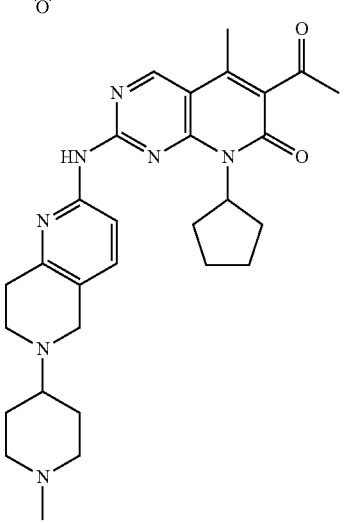

377 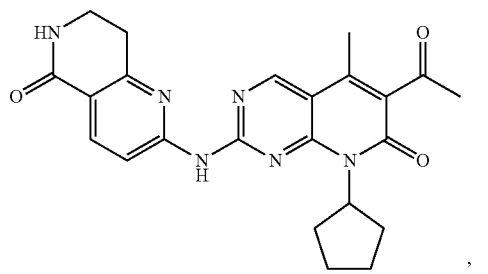

378 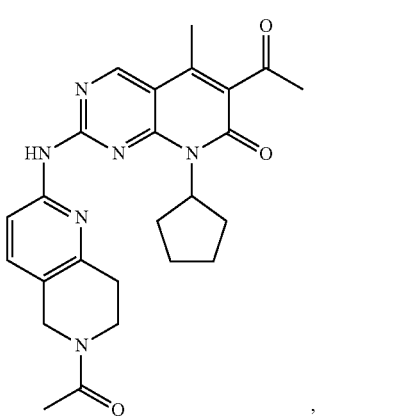

379 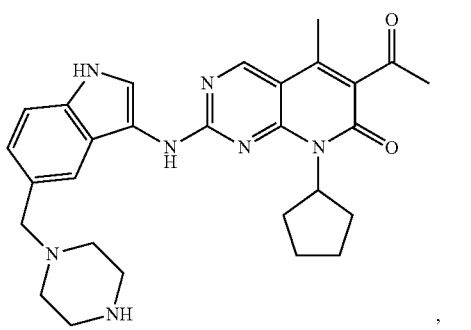

380 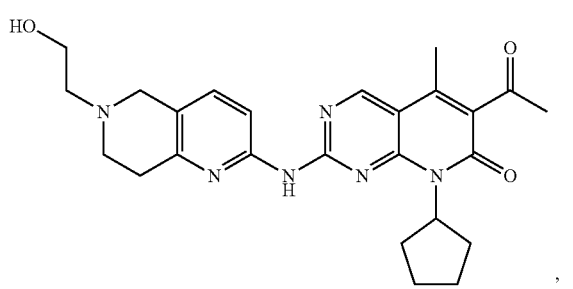

381 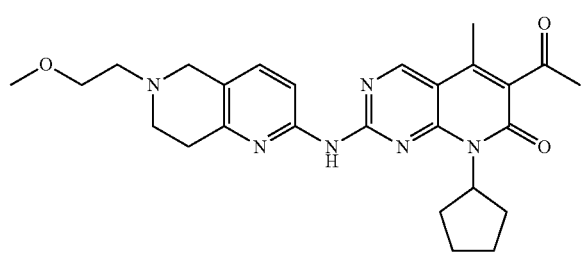

or a stereoisomer, a geometric isomer, a tautomer, an N-oxide, or a pharmaceutically acceptable salt thereof.

9. A pharmaceutical composition comprising the compound of claim 1, and at least one of pharmaceutically acceptable carriers, excipients, diluents, adjuvants, vehicles.

10. The pharmaceutical composition of claim 9 further comprising an additional therapeutic agent; wherein the additional therapeutic agent is a chemotherapeutic drug, an antiproliferative agent, an immunosuppressor, an immunologic stimulant, an anti-inflammatory reagent, an agent for treating atherosclerosis, an agent for treating pulmonary fibrosis, a CDK4/6 inhibitor, an ABL inhibitor, an ABL/Scrinhibitor, an aurora kinase inhibitor, a non-ATP competitive inhibitor of BCR-ABL, a c-KIT mutation inhibitor, an RET inhibitor, a PDGFR inhibitor, a VEGFR inhibitor, a CSF1R inhibitor, an FLT3 inhibitor, an FLT3-ITD inhibitor or a combination thereof.

11. The pharmaceutical composition of claim 10, wherein the additional therapeutic agent is chlorambucil, melphalan, cyclophosphamide, ifosfamide, busulfan, carmustine, lomustine, streptozotocin, cis-platinum, carboplatin, oxaliplatin, dacarbazine, temozolomide, procarbozine, methotrexate, fluorouracil, cytosine arabinoside, gemcitabine, purinethol, fludarabine, vinblastine, vincristine, vinorelbine, paclitaxel, docetaxel, topotecan, irinotecan, etoposide, trabectedin, dactinomycin, doxorubicin, pharmorubicin, daunomycin, mitoxantrone, bleomycin, mitomycin C, ixabepilone, tamoxifen, flutamide, gonadorelin analogue, megestrol acetate, prednisone, dexamethasone, methylprednisolone, thalidomide, interferon α, calcium folinate, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, zelboraf, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, cabozantinib, ponatinib, midostaurin, pacritinib, quizartinib, gilteritinib, AKN-028, AT-9283, crenolanib, ENMD-2076, famitinib, dovitinib, PLX-3397, palbociclib, abemaciclib, ribociclib, rigosertib sodium, selinexor, roniciclib, AT-7519, seliciclib, alvocidib or a combination thereof.

12. A method of treating a disorder or disease in a human comprising administering a therapeutically effective amount of the compound of claim 1 to the human, wherein the disorder or disease is breast cancer caused by a change in cyclin-dependent kinase, wherein the cyclin-dependent kinase is CDK4 or CDK6.

13. A drug combination comprising the compound of claim 1 and one or more other activity agents used for treating proliferative diseases, autoimmune diseases or inflammatory diseases; wherein the other activity agent is a chemotherapeutic drug, an antiproliferative agent, an immunosuppressor, an immunologic stimulant, an anti-inflammatory agent, an agent for treating atherosclerosis, an agent for treating pulmonary fibrosis, a CDK 4/6 kinase inhibitor, an ABL inhibitor, an ABL/Scr inhibitor, an aurora kinase inhibitor, a non-ATP competitive inhibitor of BCR-ABL, a c-KIT mutation inhibitor, an RET inhibitor, a PDGFR inhibitor, a VEGFR inhibitor, a CSF1R inhibitor, a FLT3 inhibitor, a FLT3-ITD inhibitor or a combination thereof.

14. A method of treating a disorder or disease in a human comprising administering a therapeutically effective amount of the pharmaceutical composition of claim 9 to the human, wherein the disorder or disease is breast cancer caused by a change in cyclin-dependent kinase, wherein the cyclin-dependent kinase is CDK4 or CDK6.

15. A drug combination comprising the pharmaceutical composition of claim 9 and one or more other activity agents used for treating proliferative diseases, autoimmune diseases or inflammatory diseases; wherein the other activity agent is a chemotherapeutic drug, an antiproliferative agent, an immunosuppressor, an immunologic stimulant, an anti-inflammatory agent, an agent for treating atherosclerosis, an agent for treating pulmonary fibrosis, a CDK 4/6 kinase inhibitor, an ABL inhibitor, an ABL/Scr inhibitor, an aurora kinase inhibitor, a non-ATP competitive inhibitor of BCR-ABL, a c-KIT mutation inhibitor, an RET inhibitor, a PDGFR inhibitor, a VEGFR inhibitor, a CSF1R inhibitor, a FLT3 inhibitor, a FLT3-ITD inhibitor or a combination thereof.

* * * * *